United States Patent

Hamajima et al.

[11] Patent Number: 6,068,619
[45] Date of Patent: May 30, 2000

[54] CROSSLINKED CELLULOSE FIBERS, ABSORBENT PAPERS AND ABSORBENT MEMBERS USING THE SAME, TOPSHEETS USING THE SAME, AND ABSORBENT ARTICLES USING THE SAME

[75] Inventors: Mitsugu Hamajima; Yasuhiro Yamamoto; Hironori Kawasaki; Minoru Nakanishi, all of Tochigi-ken, Japan

[73] Assignee: Kao Corporation, Tokyo, Japan

[21] Appl. No.: 08/910,105

[22] Filed: Aug. 13, 1997

Related U.S. Application Data

[63] Continuation of application No. 08/365,298, Dec. 28, 1994, Pat. No. 5,865,822.

[30] Foreign Application Priority Data

Dec. 28, 1993 [JP] Japan ................................. 5-336874
Mar. 25, 1994 [JP] Japan ................................. 6-056349

[51] Int. Cl.$^7$ ....................................................... A61F 13/15
[52] U.S. Cl. ........................ 604/378; 604/366; 604/368; 604/372; 604/374
[58] Field of Search ............................. 604/366, 368, 604/372, 374, 378, 358, 365

[56] References Cited

U.S. PATENT DOCUMENTS

| | | |
|---|---|---|
| 3,017,304 | 1/1962 | Burgeni . |
| 3,932,209 | 1/1976 | Chatterjee ............................ 162/157 |
| 4,035,147 | 7/1977 | Sangenis . |
| 4,090,515 | 5/1978 | Karami . |
| 4,195,634 | 4/1980 | DiSalvo . |
| 4,324,246 | 4/1982 | Mullane et al. . |
| 4,324,247 | 4/1982 | Aziz . |
| 4,333,463 | 6/1982 | Holtman . |
| 4,500,315 | 2/1985 | Pieniak et al. . |
| 4,631,227 | 12/1986 | Nakamura . |
| 4,699,823 | 10/1987 | Kellenberger . |
| 4,834,735 | 5/1989 | Alemany et al. . |
| 4,935,022 | 6/1990 | Lash ....................................... 604/368 |
| 5,002,986 | 3/1991 | Fujiura et al. . |
| 5,009,653 | 4/1991 | Osborn, III . |
| 5,015,245 | 5/1991 | Noda . |
| 5,061,259 | 10/1991 | Goldman et al. . |
| 5,147,505 | 9/1992 | Altman . |
| 5,160,582 | 11/1992 | Takahashi ............................. 162/117 |
| 5,262,218 | 11/1993 | Putzier . |
| 5,391,161 | 2/1995 | Hellgren . |
| 5,720,737 | 2/1998 | Hamajima et al. ..................... 604/378 |

FOREIGN PATENT DOCUMENTS

| | | |
|---|---|---|
| 0606336 A1 | 9/1992 | European Pat. Off. . |
| 49-143589 | 12/1974 | Japan . |
| 54-36793 | 11/1979 | Japan . |
| 59-204956 | 11/1984 | Japan . |
| 62-32950 | 2/1987 | Japan . |
| 63-264971 | 11/1988 | Japan . |
| 133176 | 7/1989 | Japan . |
| 489053 | 3/1992 | Japan . |
| 568693 | 3/1993 | Japan . |
| 670953 | 3/1994 | Japan . |
| 2252047A | 7/1992 | United Kingdom . |

*Primary Examiner*—Michael J. Milano
*Attorney, Agent, or Firm*—Birch, Stewart, Kolasch & Birch, LLP

[57] ABSTRACT

An absorbent member in an absorbent article comprises a absorbent polymer and cellulose fibers. The absorbent polymer has a centrifugal retentive capacity for physiological saline of 30 g/g or more and a permeation rate of physiological saline of 10 ml/minute or more. The cellulose fibers are crosslinked cellulose fibers obtainable by an intramolecular and/or intermolecular crosslinking of the cellulose fibers. Particularly, an absorbent member in a sanitary napkin has a centrifugal retentive capacity of pseudo-blood of 30 g or more and a permeation rate of pseudo-blood of 50 ml/minute or more. Also, a topsheet in the absorbent article comprises a liquid-permeable sheet, which comprises at least a layer in contact with a user's skin and a layer not in contact with the user's skin, the layers being overlaid and combined with each other into a unitary body. The layer in contact with the user's skin comprises a porous film of a thermoplastic resin or a nonwoven fabric of synthetic fibers. The layer not in contact with the user's skin comprises an absorbent sheet, which comprises at least bulky cellulose fibers. The absorbent member and the topsheet should preferably comprise crosslinked cellulose fibers.

35 Claims, 8 Drawing Sheets

CROSSLINKED CELLULOSE FIBERS, ABSORBENT PAPERS AND ABSORBENT MEMBERS USING THE SAME, TOPSHEETS USING THE SAME, AND ABSORBENT ARTICLES USING THE SAME

This application is a continuation of application Ser. No. 08/365,298, filed on Dec. 28, 1994, now U.S. Pat. No. 5,865,822 the entire contents of which are hereby incorporated by reference.

BACKGROUND OF THE INVENTION

This invention relates to bulky cellulose fibers having a high liquid absorbency, an absorbent paper and an absorbent member each using said cellulose fibers, a topsheet using said cellulose fibers, and an absorbent article using said cellulose fibers.

Various absorbent articles, such as sanitary napkins, having an improved absorption of body fluids, have heretofore been proposed, and various improvements have also been made. Most of the studies for making the improvements have heretofore been directed to the improvement in the absorption rate, inhibition of reflow of the body fluid from the absorbent member to the surface, prevention of leakage, and reduction of stickiness to the user's body.

For example, as for the material for an absorbent member to be used in a sanitary napkin, it has been proposed to absorb and retain body fluids by using an absorbent polymer, which utilizes physicochemical effects, i.e. ionic osmotic pressures, in lieu of hydrophilic absorbent paper or pulp, which absorbs and retains the body fluids by the utilization of physically fine spaces. It has been reported that, with the proposed technique, the absorption capacity can be enhanced, and the reflow of the body fluids after being absorbed can be prevented from occurring. Actually, the proposed technique provides an improved absorbency of the sanitary napkin. Therefore, at present, absorbent members utilizing a combination of pulp and an absorbent polymer are used for most of sanitary napkins.

However, as is manifested by the fact that the main reason for dissatisfaction of the sanitary napkins resides in the leakage, even with the sanitary napkins utilizing the absorbent polymers, the requirement for the prevention of the leakage cannot be satisfied sufficiently.

Specifically, with the absorbent polymers which absorb and retain body fluids by utilizing the ionic osmotic pressures, a limitation is imposed on the body fluids absorption rate. Also, the absorbent polymers can absorb the body fluids only when they are wetted with the body fluids. Therefore, in cases where the highly absorbent polymers are used, it is necessary for pulp, or the like, having a high water absorption rate to be used in combination with the absorbent polymers. However, when the pulp is formed into a soft fluff absorbent layer as an absorbent member, the pulp absorbs blood spot-wise, and therefore the problems occur in that the diffusing capacity for the efficient utilization of the entire area of the absorbent member cannot be kept high.

Also, the pulp exhibits certain levels of compression and bending recoveries when it is in the dry state. However, when the pulp is in the wet state, the strength of the pulp decreases markedly, and the pulp exhibits little compression and bending recoveries. Therefore, when stress is applied to the wet pulp, compression deformation (hereinafter referred to as the "twist") occurs with the pulp, and the absorption spaces in the pulp reduce markedly. As a result, the body fluids, which have once been absorbed by the pulp, returns to the body side due to the twist, and the problems with regard to stickiness and leakage occur.

In addition, the reduction in the pulp fiber spaces due to the twist causes the resistance to transfer of the body fluids to the polymer to increase, and therefore the absorption efficiency of the polymer decreases. Moreover, synergistic effects occur from the reduction in the pulp fiber spaces due to reexcretion of the body fluids and from the reduction in the absorption spaces due to the swelling of the polymer. Due to such synergistic effects, the reabsorption rate of the entire absorbent member decreases markedly after the twist has occurred, and the leakage problems are often caused to occur.

Therefore, in order that the diffusing capacity of the pulp may be enhanced and the reduction in the absorption spaces due to the twist can be kept small, techniques for improving the diffusing capacity and the inhibition of reflow of the body fluids from the absorbent member to the surface by compressing the pulp and increasing the density of the pulp have been proposed in, for example, Japanese Utility Model Laid-open Application 49-143589, U.S. Pat. No. 3,017,304, and Japanese Patent Publication 54-36793 and 1-33176. However, none of these proposed techniques can solve the essential problems in that the strength of the pulp decreases markedly when the pulp is wetted. Conversely, these proposed techniques have the problems in that the resistance to transfer of blood to the polymer becomes very high due to the markedly reduced distance between pulp fibers, and as a result the absorption efficiency of the polymer used in combination with the pulp becomes low.

A sanitary napkin, which is very thin and has a high comfortableness and a high absorbency, is disclosed in, for example, Japanese Patent Laid-open Application 4-89053. The disclosed sanitary napkin aims at improving the absorption efficiency of a polymer and meeting both of the requirements for a small thickness and a high absorbency by combining a highly diffusing absorbent sheet and a specific polymer sheet with each other.

With the disclosed technique, a sanitary napkin, which has an improved absorption efficiency of the polymer, an absorbency is enhanced to some extent, and a small thickness can certainly be obtained. However, there are user's expectation and a need for sanitary napkins having a higher comfortableness and a higher absorbency. In particular, at present, there is a need for a very thin sanitary napkin, which has an excellent absorption performance and is free of the problems with regard to reflow of body fluids from an absorbent member to the surface, stickiness to the body, and leakage even during a long period of use under conditions of large excretion amounts.

Heretofore, in cases where the amount of a absorbent polymer used in an absorbent member is increased so that the absorption performance may be enhanced, the absorption performance can be enhanced as the amount of the absorbent polymer used in the absorbent member becomes large to a certain extent. However, if the amount of the absorbent polymer used in the absorbent member becomes very large, the spaces among the polymer particles after absorbing body fluids will become markedly small. As a result, the reabsorption rate becomes low, and therefore the absorption performance becomes bad.

Specifically, due to a gel blocking phenomenon of a polymer, a limitation has heretofore been imposed on the amount of the polymer used. Therefore, at present, an absorbent article cannot be obtained which perfectly satisfies the requirements for the absorption performance, such as inhibition of reflow of body fluids from the absorbent member to the surface, and inhibition of leakage, during the use under the conditions of a long period of use and a large excretion amount.

For the purpose of preventing the twist of wet pulp, various techniques have heretofore been proposed wherein the pulp cellulose is crosslinked by using an appropriate crosslinking agent, a decrease in the modulus of elasticity in the wet state is thereby restricted, and the twist and permanent set in fatigue are thereby reduced. For example, a crosslinked pulp having a bulky structure (i.e., a torsion structure) is proposed in Japanese Patent Laid-open Application 63-264971. Certainly, the absorbent member utilizing such a crosslinked pulp maintains the bulky structure not only in the dry state but also after absorbing body fluids and exhibits good spot absorbency and a high absorption rate.

However, it has been found that, with the absorbent member utilizing the crosslinked pulp, if it is used in an erroneous manner, the capacity of the entire absorbent member for retaining body fluids will decrease, reflow of the body fluids from the absorbent member to the surface will increase, and the body fluids will become apt to leak from the absorbent member. Specifically, in cases where the pulp is crosslinked, though its modulus of elasticity in the wet state can be improved, the capacity of the fibers themselves for absorbing body fluids is restricted due to the crosslinking. As a result, the capacity of the pulp itself for retaining the body fluids becomes low. Therefore, unless the capacity of the polymer for absorbing and retaining the body fluids is increased, the capacity of the entire absorbent member, which utilizes the crosslinked pulp, for absorbing and retaining the body fluids becomes low, reflow of the body fluids from the absorbent member to the surface increases, and the leakage inhibiting performance of absorbent member becomes bad.

For the purpose of preventing the gel blocking phenomenon of a polymer may be prevented and the absorption efficiency of the polymer may be enhanced, a technique for utilizing an absorbent member, which comprises a mixture of hydrophilic fibers, such as pulp, and a polymer, is proposed in, for example, Japanese Patent Laid-open Application 59(1984)-204956, and techniques for using a homogeneous layer, which is composed of a polymer and pulp, only at the bottom surface of an absorbent member are proposed in, for example, Japanese Patent Laid-open Applications 59-135149 and 63-109859. Also, for the purpose of preventing the gel blocking phenomenon of a polymer after absorbing body fluids more efficiently, techniques for constituting an absorbent member, in which the polymer concentration is reduced from the bottom surface towards the top surface of the absorbent member, i.e. a polymer concentration gradient is provided, are proposed in, for example, Japanese Patent Laid-open Applications 62-32950 and 62-45703.

The above-enumerated techniques relate to the constitution techniques for pulp and a polymer and have certain levels of effects of restricting the gel blocking phenomenon of a polymer and enhancing the absorption efficiency of the polymer. However, none of these proposed techniques can solve the essential problems in that, when the pulp is wetted, it becomes twisted, the fiber spaces become small, and the reabsorption rate becomes low.

U.S. Pat. No. 5,061,259 indicates that fine powder of a polymer constitutes a cause for the gel blocking phenomenon and discloses an absorbent member comprising a mixture of a polymer, the particle diameter distribution of which is defined so as to have a central particle diameter falling within the range of 400 $\mu$m to 700 $\mu$m, and hydrophilic fibers.

The aforesaid U.S. Patent specification exemplifies that a crosslinked pulp may be used as the hydrophilic fibers. However, the aforesaid U.S. Patent specification does not indicate anything about the effects obtained from the use of the crosslinked pulp, nor does it describe anything about the limitation of the crosslinked pulp as the hydrophilic fibers. Specifically, the technique disclosed in the aforesaid U.S. Patent specification cannot solve the essential problems in that, when the hydrophilic fibers are wetted, the spaces among the fibers become small, and the reabsorption rate becomes low.

Also, by the removal of fine powder of the polymer, the gel blocking phenomenon can be restricted to some extent. However, the gel blocking phenomenon of the polymer has the nature such that it cannot be eliminated only with the adjustment of the particle diameter distribution, and therefore the aforesaid problems of the polymer cannot be eliminated by the technique disclosed in the aforesaid U.S. Patent specification.

As for a topsheet for an absorbent article, the topsheet is required to have the liquid absorbing and permeating functions such that body fluids such as blood or urine can be quickly transferred to and absorbed by the absorbent member.

The transfer of the liquid from the topsheet to the absorbent member is achieved only when the topsheet and the absorbent member are in close contact with each other. If the topsheet and the absorbent member are located at a spacing from each other, the transfer of the liquid from the topsheet to the absorbent member will reduce markedly, and the amount of the liquid remaining on the topsheet will become large. As a result, a sticky feeling will be given to the user. Also, liquid diffusion and liquid flow will occur, and liquid leakage will be thereby caused to occur.

The problems with regard to the insufficient absorption due to separation of the topsheet and the absorbent member from each other occur particularly markedly in cases where the topsheet comprises a fiber aggregate, such as a nonwoven fabric, which has the absorbency by itself.

For example, in cases where the topsheet comprises a nonwoven fabric, if separation of the topsheet and the absorbent member from each other occurs, the liquid will remain stagnant in the topsheet and cannot be transferred to the absorbent member. Therefore, a sticky feeling will continue to be given to the user, and the absorbent article cannot be used comfortably.

In cases where the topsheet comprises a film type of material, such as a porous film or a porous net, which does not have the absorbency by itself, if the topsheet and the absorbent member are in close contact with each other, the liquid will not be apt to remain in the topsheet, a sticky feeling will not be given to the user, and the absorbent article can be used comfortably. However, if the topsheet and the absorbent member separate from each other, because the topsheet by itself has no absorbency, the liquid will not be absorbed by the topsheet and will flow along the surface of the topsheet. As a result, the liquid will leak from the absorbent article. This is a very serious drawback for the absorbent article.

SUMMARY OF THE INVENTION

Accordingly, the primary object of the present invention is to provide cellulose fibers for use in an absorbent article, which do not undergo the twist and permanent set in fatigue even when they are wetted with liquid.

Another object of the present invention is to provide an absorbent paper for use in an absorbent article, which absorbent paper has a high permeability to liquid.

A further object of the present invention is to provide an absorbent paper for use in an absorbent article, which absorbent paper has a high liquid diffusing capacity.

A still further object of the present invention is to provide an absorbent paper for use in an absorbent article, which absorbent paper has a high permeability to a liquid and a high liquid diffusing capacity.

Another object of the present invention is to provide an absorbent article, which exhibits little retention of liquid on the surface, a high liquid absorbency, and little stickiness.

A further object of the present invention is to provide an absorbent member for use in an absorbent article, which absorbent member very quickly absorbs and diffuses liquid and which is free of reflow of the liquid to the surface and liquid leakage.

A still further object of the present invention is to provide an absorbent article, which restricts reflow of the liquid from an absorbent member to the surface and liquid leakage even when it is put on and used for a long period of time or even when it is used under violent motion, and which has a high absorbency and a high comfortableness.

Other objects and aspects of the invention will become apparent from the following description of embodiments with reference to the accompanying drawings.

The present invention provides an absorbent article comprising a liquid permeable topsheet, a liquid impermeable back sheet and a liquid retentive absorbent member interposed between the topsheet and the back sheet, the absorbent article being characterized in that:

the absorbent member comprises an absorbent polymer and cellulose fibers;

the absorbent polymer has a centrifugal retentive capacity for physiological saline, which is measured after equilibrium absorption swelling with the physiological saline, of 30 g/g or more, and a permeation rate of physiological saline of 10 ml/minute or more, the permeation rate being measured by introducing 0.05 g of the absorbent polymer into a cylinder having a cross-sectional area of 0.785 cm$^2$ (inner diameter: 10 mm), allowing the absorbent polymer to absorb and swell with physiological saline until the swelling reaches equilibrium, and thereafter causing physiological saline to permeate through the absorbent polymer; and the cellulose fibers are crosslinked cellulose fibers obtainable by an intramolecular and/or intermolecular crosslinking of the cellulose fibers.

The present invention also provides a sanitary napkin comprising a liquid permeable topsheet, a liquid impermeable back sheet, and a liquid retentive absorbent member interposed between the topsheet and the back sheet, the sanitary napkin being characterized in that:

the absorbent member has a centrifugal retentive capacity for pseudo-blood, which is measured after equilibrium absorption swelling with the pseudo-blood, of 30 g/g or more, and a permeation rate of pseudo-blood of 50 ml/minute or more, the permeation rate being measured by securing the absorbent member having a thickness of 0.5 to 5 mm to an end of a cylinder having a cross-sectional area of 10 cm$^2$ (inner diameter: 35.8 mm), allowing the absorbent member to absorb and swell with pseudo-blood until the swelling reaches equilibrium, and thereafter causing pseudo-blood to permeate through the absorbent member.

The present invention further provides a composite absorbent paper comprising a permeable absorbent paper and a diffusing absorbent paper, wherein the permeable absorbent paper comprises 50 to 98 parts by weight of bulky crosslinked cellulose fibers obtainable by an intramolecular and/or intermolecular crosslinking of cellulose fibers having a degree of fiber roughness of 0.3 mg/m or more, and 2 to 50 parts by weight of thermally fusible bonding fibers, the permeable absorbent paper having a basis weight of 20 to 60 g/m$^2$;

the diffusing absorbent paper comprises 20 to 80 parts by weight of bulky crosslinked cellulose fibers obtainable by an intramolecular and/or intermolecular crosslinking of cellulose fibers having a degree of fiber roughness of 0.3 mg/m or more, 80 to 20 parts by weight of hydrophilic fine fibers, and 0 to 30 parts by weight of thermally fusible bonding fibers, the diffusing absorbent paper having a basis weight of 20 to 60 g/m$^2$; and the permeable absorbent paper and the diffusing absorbent paper are combined with each other into a unitary body.

The present invention still further provides a diffusing absorbent paper comprising 20 to 80 parts by weight of bully crosslinked cellulose fibers obtainable by an intramolecular and/or intermolecular crosslinking of cellulose fibers having a degree of fiber roughness of 0.3 mg/m or more, 80 to 20 parts by weight of hydrophilic fine fibers, and 0 to 30 parts by weight of thermally fusible bonding fibers, wherein the diffusing absorbent paper has a basis weight of 20 to 60 g/m$^2$, a thickness under a load of 2.5 g/m$^2$ of 0.2 to 0.8 mm, an absorption height after 1 minute absorption of physiological saline by Klemm's Method of 50 mm or more, and an absorption height after 10 minutes absorption of physiological saline by Klemm's Method of 100 mm or more.

The present invention also provides a permeable absorbent paper comprising 50 to 98 parts by weight of bulky crosslinked cellulose fibers obtainable by an intramolecular and/or intermolecular crosslinking of cellulose fibers having a degree of fiber roughness of 0.3 mg/m or more, and 2 to 50 parts by weight of thermally fusible bonding fibers, wherein the permeable absorbent paper has a basis weight of 20 to 60 g/m$^2$.

The present invention further provides bulky crosslinked cellulose fibers obtainable by an intramolecular and/or intermolecular crosslinking of cellulose fibers having a degree of fiber roughness of 0.3 mg/m or more.

The present invention still further provides an absorbent article comprising a liquid permeable topsheet, a liquid impermeable back sheet, and a liquid retentive absorbent member interposed between the topsheet and the back sheet, the absorbent article being characterized in that:

the topsheet comprises at least a first layer in contact with a user's skin and a second layer not in contact with the user's skin, the layers being overlaid and combined with each other into a unitary body, the first layer comprises a perforated film made of a thermoplastic resin or a nonwoven fabric made of synthetic fibers, and the second layer comprises an absorbent sheet made of at least bulky cellulose fibers.

With the absorbent article in accordance with the present invention, the absorbent member is constituted by combining the absorbent polymer, which has a high centrifugal retentive capacity and a high permeation rate after liquid absorption (i.e., a good liquid passing performance), and the crosslinked cellulose fibers, which undergo little twist and little permanent set in fatigue even when they absorb a body fluid, i.e. even when they are wetted. Therefore, by virtue of synergetic effects better than effects obtained when the absorbent polymer or the crosslinked cellulose fibers are used alone, the absorbent article in accordance with the present invention has a high absorption rate, particularly a high reabsorption rate, a high body fluid immobilizing capacity, enhanced inhabitation of reflow of the body fluid from the absorbent member to the surface, and enhanced inhibition of liquid leakage.

Specifically, the excreted body fluid is first absorbed into fiber spaces (absorption spaces), which are formed by the crosslinked cellulose fibers. The crosslinked cellulose fibers undergo little twist and little permanent set in fatigue even when they are wetted. Therefore, the absorption spaces, into which the body fluid is to be absorbed temporarily, can be kept stable. Also, the absorbent polymer has a high centrifugal retentive capacity and a good body fluid passing performance. Accordingly, the body fluid, which has been absorbed into the absorption spaces, can then be smoothly guided to and retained by the absorbent polymer such that no gel blocking phenomenon may occur. Both of the absorption spaces, into which the body fluid is to be absorbed temporarily, and the absorbent polymer, which retains the body fluid, have a good body fluid passing performance. Therefore, even when the absorbent article is used under the conditions of repeated excretion of body fluids, the absorption performance does not become bad, and the body fluids can be guide to the absorbent polymer very reliably and efficiently and can thus be immobilized by the absorbent polymer.

As a result, the absorbent article in accordance with the present invention exhibits little amount of reflow of the liquid from the absorbent member to the surface, little liquid leakage, and little stickiness and can be used with a high comfortableness even when it is used under the conditions of small excretion amounts of body fluids, and even when it is used for a long period of time under the conditions of large excretion amounts of body fluids.

BRIEF DESCRIPTION OF THE DRAWINGS

The invention will be more particularly described with reference to the accompanying drawings, in which.

DESCRIPTION OF THE PREFERRED EMBODIMENTS

Figure 1:
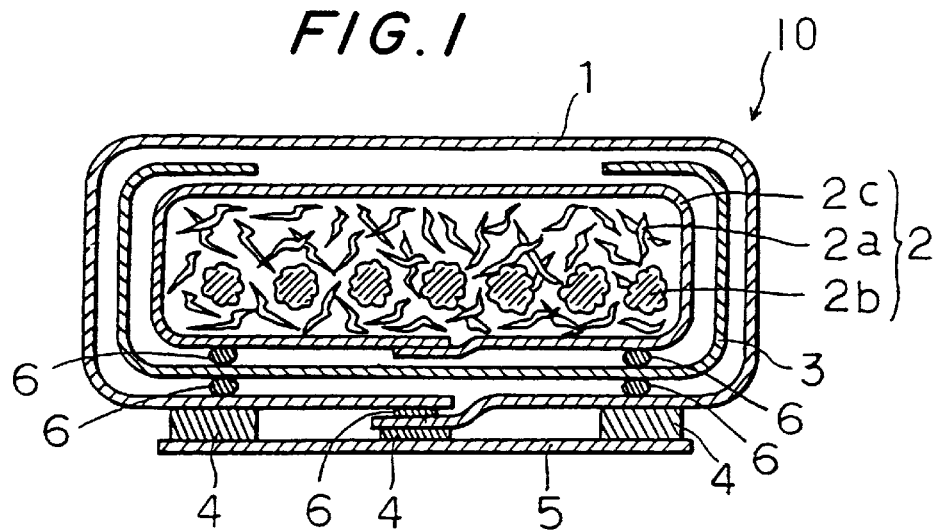
FIG. 1 is a sectional view showing a first embodiment of the absorbent article in accordance with the present invention, which is constituted as a sanitary napkin, the sectional view being taken along the transverse direction of the sanitary napkin.

FIG. 1 shows a first embodiment of the absorbent article in accordance with the present invention, which is constituted as a sanitary napkin 10. The sanitary napkin 10 comprises a liquid permeable topsheet 1, a liquid impermeable back sheet 3, and a liquid retentive absorbent member 2 interposed between the topsheet 1 and the back sheet 3.

The absorbent member 2 comprises an absorbent polymer 2b and cellulose fibers 2a.

The absorbent polymer 2b has a centrifugal retentive capacity for physiological saline, which is measured after equilibrium absorption swelling with the physiological saline, of 30 g/g or more. Also, the absorbent polymer 2b has a permeation rate of physiological saline of 10 ml/minute or more. The permeation rate is measured by introducing 0.05 g of the absorbent polymer 2b into a cylinder having a cross-sectional area of 0.785 cm$^2$ (inner diameter: 10 mm), allowing the introduced absorbent polymer 2b to absorb and swell with physiological saline until the swelling reaches equilibrium, and thereafter causing the physiological saline to permeate through the absorbent polymer 2b.

The cellulose fibers 2a are the crosslinked cellulose fibers obtainable from an intramolecular and/or intermolecular crosslinking of cellulose fibers.

Specifically, the sanitary napkin 10 is formed in a substantially longitudinally elongated shape. When the sanitary napkin 10 is used, the topsheet 1 is located on the front surface side that comes into contact with the skin, and the back sheet 3 is located on the back surface side that comes into contact with the underwear. Also, the absorbent member 2 intervenes between the topsheet 1 and the back sheet 3.

As illustrated in FIG. 1, the back surface, the entire side surfaces, and the peripheral portions of the front surface of the absorbent member 2 are covered with the back sheet 3. Also, the entire surfaces of the absorbent member 2 and the back sheet 3 are covered with the topsheet 1. The center portion of the front surface of the absorbent member 2 is covered directly with the topsheet 1 such that a body fluid can directly permeate through the topsheet 1 into the absorbent member 2.

Three strip-like adhesive parts 4, 4, 4 extend longitudinally on the back surface side of the topsheet 1. The adhesive parts 4, 4, 4 are protected by a release paper 5. In FIG. 1, reference numeral 6 represents a joint.

Features of the sanitary napkin 10, which is a first embodiment of the absorbent article in accordance with the present invention, will be described hereinbelow. The absorbent member 2 comprises the cellulose fibers 2a and the absorbent polymer 2b, which are dispersed and mixed with each other, and an absorbent paper 2c covers the entire surfaces of the mixture of the cellulose fibers 2a and the absorbent polymer 2b. The outermost part of the absorbent member 2 is formed by using the absorbent paper 2c.

The absorbent polymer 2b has a centrifugal retentive capacity for physiological saline of 30 g/g or more, and should preferably have a centrifugal retentive capacity for physiological saline falling within the range of 30 g/g to 60 g/g. The centrifugal retentive capacity for physiological saline is measured after the absorbent polymer 2b has been immersed in the physiological saline and has then been caused to undergo equilibrium absorption swelling with the physiological saline. Also, the absorbent polymer 2b has a permeation rate of physiological saline of 10 ml/minute or more, preferably 15 ml/minute or more. The permeation rate is measured by introducing 0.05 g of the absorbent polymer 2b into a cylinder having a cross-sectional area of 0.785 cm$^2$ (inner diameter: 10 mm), allowing the absorbent polymer 2b to absorb and swell with physiological saline until the swelling reaches equilibrium, allowing the swollen absorbent polymer 2b to precipitate, and thereafter causing the physiological saline to permeate through the precipitated absorbent polymer 2b. How the centrifugal retentive capacity and the permeation rate are measured will be described later.

If the centrifugal retentive capacity of the absorbent polymer 2b with respect to physiological saline is lower than 30 g/g, a high capacity for absorbing and retaining a liquid cannot be obtained. If the centrifugal retentive capacity of the absorbent polymer 2b with respect to physiological saline is higher than 60 g/g, though the capacity for retaining the absorbed body fluid can be kept high, the gel strength after the swelling will become low, and the permeation rate of the absorbent polymer 2b after being swollen will become low. Therefore, the centrifugal retentive capacity of the absorbent polymer 2b with respect to physiological saline should preferably be not higher than 60 g/g.

Also, if the permeation rate described above is lower than 10 ml/minute, the body fluid passing performance of the absorbent polymer 2b after being swollen will become bad, and the reabsorption rate of the absorbent polymer 2b after being subjected to repeated excretion of body fluids will become low. Thus the high absorbency of the absorbent polymer 2b cannot be utilized efficiently.

Insofar as the aforesaid requirements for the centrifugal retentive capacity and the permeation rate are satisfied, no limitation is imposed on the composition of and the producing process for the absorbent polymer 2b. However, the absorbent polymer 2b should preferably be constituted of water-insoluble, hydrophilic, crosslinked polymer particles, which are obtained by polymerizing acrylic acid, an alkali metal salt of acrylic acid (e.g. sodium salt or potassium salt), or the like, and crosslinking and insolubilizing the resulting polymer. Such water-insoluble, hydrophilic, crosslinked polymer particles can absorb and retain a large amount of liquid by means of the ionic osmotic pressure such that the absorbed liquid may not leak out even under pressurized conditions.

In particular, the absorbent polymer 2b should preferably be constituted of the water-insoluble, hydrophilic, crosslinked polymer particles having the absorbing functions such that the polymer particles can quickly absorb the body fluid from the absorption spaces in the absorbent member, which temporarily store the body fluid, such that the surfaces of the polymer particles can be kept in a dry state after the polymer particles have absorbed the body fluid and have been swollen, and such that the polymer particles may not obstruct the transfer of a body fluid which is excreted later.

Also, if the absorbent polymer has a uniform crosslinked structure, the absorbing functions described above cannot easily be obtained. Therefore, the absorbent polymer should preferably be provided with a crosslinking density gradient.

In order to impart a crosslinking density gradient to the absorbent polymer, one of various processes may be employed. For example, in cases where a polyacrylate is employed as the absorbent polymer, the polyacrylate may further be reacted with a crosslinking agent (hereinafter referred to as the "crosslinking agent for the absorbent polymer"), which is capable of reacting with the functional group of the polyacrylate, and the surface of the polymer may thus be subjected to the crosslinking. In particular, the crosslinking density gradient can be adjusted by adjusting the amount of the crosslinking agent for the absorbent polymer used.

As the polymer crosslinking agent, a water-soluble compound having at least two functional groups, which are capable of reacting with the carboxyl group, should preferably be used. Examples of such compounds include polyglycidyl ethers, such as ethylene glycol diglycidyl ether, polyethylene glycol diglycidyl ether, and glycerin triglycidyl ether; haloepoxy compounds, such as epichlorohydrin, and $\alpha$-methylchlorohydrin; polyaldehydes, such as glutaraldehyde, and glyoxal; polyols, such as glycerin; and polyamines, such as ethylenediamine. In order that an optimum crosslinking density gradient may be obtained, the amount of the polymer crosslinking agent used should preferably fall within the range of 0.1 to 1 part by weight per 100 parts by weight of the polymer, such as the polyacrylate described above.

The particles of the absorbent polymer should preferably have an aspherical shape, and the degree of shape irregularity P of the particles of the absorbent polymer should preferably be 1.2 or more, and should more preferably fall within the range of 1.2 to 3.

In cases where the particles of the absorbent polymer have an aspherical shape, the spaces among the particles can be prevented from decreasing due to rearrangement of the particles and close contact of the particles with one another when the absorbent polymer absorbs the body fluid and is thereby swollen. Also, if the degree of shape irregularity P of the particles of the absorbent polymer is lower than 1.2, the irregularity value of the unevenness of the surfaces of the particles of the absorbent polymer, which has been swollen, will become insufficient. As a result, the spaces cannot be kept among the particles of the absorbent polymer, which has been swollen, and the problems will often occur in that the liquid passing performance between the particles becomes bad. Therefore, the degree of shape irregularity P of the particles of the absorbent polymer should preferably be 1.2 or more.

The degree of shape irregularity P represents the degree of roughness of the particles of the absorbent polymer and can be calculated with Formula (1) shown below.

$$P=1/L \tag{1}$$

wherein P represents the degree of shape irregularity, l represents the circumferential length of the polymer particle, and L represents the circumferential length of the circle corresponding to the projected particle, which is calculated with Formula (2).

$$L=2\pi r=2\pi(S/\pi)^{1/2} \tag{2}$$

wherein S represents the true area of the protected particle, and r represents the radius of the circle corresponding to the projected circle.

The true area S and the circumferential length l of the projected particle used in the calculation of the degree of shape irregularity P can be measured by, for example, viewing the particle of the absorbent polymer as a projected particle by using the image processor available under the trade name "IV Image Processor EXCEL" (supplied by Nippon Avionics Co., Ltd.).

As described above, the absorbent polymer used in the present invention can be imparted with the absorption physical properties described above by controlling the crosslinking density, preferably by the adjustment of the amount of the crosslinking agent for the absorbent polymer. The absorption physical properties can thus be improved by the chemical structure control. Also, the absorption physical properties can be improved even further by the physical structure control with respect to the shape and the degree of shape irregularity of the particles of the absorbent polymer.

Specifically, after the absorbent polymer absorbs the body fluid until the swelling reaches equilibrium, the physical structure of the swollen absorbent polymer largely participates in the liquid passing performance. In particular, if a large amount of spherical particles of the absorbent polymer are used, the particles of the absorbent polymer will be apt to become packed very densely. As a result, the spaces among the particles will decrease markedly, and the liquid passing performance will become bad. Therefore, in order for the spaces to be kept among the particles of the absorbent polymer even when the particles are swollen, the shape of the particles of the absorbent polymer should preferably be designed such that the particles of the absorbent polymer may have the degree of shape irregularity P described above.

The absorbent polymer having the degree of shape irregularity P described above can be obtained by dividing the absorbent polymer, which has been obtained from bulk polymerization. The absorbent polymer having the degree of shape irregularity P described above can also be obtained by carrying out a catalytic reaction between the particles of the absorbent polymer, which are obtained during the production of the absorbent polymer, by using the crosslinking agent described above. Also, as the absorbent polymer, particles of the absorbent polymer, which have irregular shapes and are obtained by granulating the primary particles of the absorbent polymer obtained with the processes described above, can preferably be used.

The amount of the absorbent polymer used should preferably fall within the range of 20 to 80% by weight, based on the total weight of the absorbent member, and should more preferably fall within the range of 30 to 60% by weight, based on the total weight of the absorbent member. Also, the absorbent polymer should be preferably spread at an amount falling within the range of 20 to 500 g per 1 m$^2$ absorbent member, and more preferably falling within the range of 30 to 300 g per 1 m$^2$ absorbent member. The amount of the absorbent polymer used and the amount of the absorbent polymer spread over 1 m$^2$ absorbent member should be preferably selected in accordance with the kind and the purpose of the absorbent article used.

For example, in the field of the sanitary napkins for absorbing catamenial blood, as for articles having a small absorption amount, such as panty liners, the amount of the absorbent polymer used may be small. Conversely, as for articles having a large absorption amount, such as the articles to be used for a long period of time or for night, the amount of the absorbent polymer used and its proportion should preferably be set to be large.

The absorbent article in accordance with the present invention is particularly suitable as the absorbent article capable of exhibiting a high absorbency even when it is used for a long period of time under the conditions of large amounts of excreted body fluids. Therefore, in order that the effects of the absorbent article in accordance with the present invention can be obtained most markedly, the absorbent polymer should be most preferably spread over the absorbent member at an amount falling within the range of 100 to 300 g per 1 m² absorbent member.

Also, the amount of the absorbent polymer used per absorbent article can be selected appropriately in accordance with the kind and the size of the absorbent article.

For example, as for the sanitary napkins, the amount of the absorbent polymer used per sanitary napkin should preferably fall within the range of 0.3 to 5 g, and should more preferably fall within the range of 1 to 3 g. As for the paper diapers for children the amount of the absorbent polymer used per paper diaper should preferably fall within the range of 5 to 30 g, and should more preferably fall within the range of 10 to 25 g.

If the amount of the absorbent polymer used in a sanitary napkin is smaller than 0.3 g, if the amount of the absorbent polymer used in paper diaper is smaller than 5 g, or if the absorbent polymer is spread at an amount of less than 20 g per 1 m², the capacity for immobilizing the liquid will become insufficient.

Also, if the amount of the absorbent polymer used in a sanitary napkin is larger than 5 g, if the amount of the absorbent polymer used in a paper diaper is more than 30 g, if the absorbent polymer is spread at an amount of more than 500 g per 1 m², or if the weight proportion of the absorbent polymer is higher than 80% by weight, based on the total weight of the absorbent member, the absorbent polymer cannot be perfectly secured in the absorbent member.

As illustrated in FIG. 1, the absorbent polymer 2b is dispersed and mixed with the cellulose fibers 2a. Alternatively, the absorbent polymer 2b may be sandwiched between sheets of absorbent paper. No limitation is imposed on how the absorbent polymer is located in the absorbent member. In the present invention, in addition to the design of the absorbent polymer, it is important to design the absorption spaces, in which the body fluid is to be temporarily stored in the absorbent member and which are constituted by paper, pulp fibers, or the like.

Specifically, with an absorbent member, which mainly comprises a fluff sheet constituted of ordinary softwood pulp, as in the conventional absorbent article, even if the absorbent polymer described above is used, the absorption rate becomes low and liquid leakage is caused to occur due to the twist and permanent set in fatigue, which occur with the pulp, before the absorbency function of the absorbent polymer works to the highest extent.

In the absorbent article in accordance with the present invention, the crosslinked cellulose fibers 2a should preferably be used which have been obtained from an intramolecular and/or intermolecular crosslinking of the cellulose fibers such that the cellulose fibers may undergo little twist and little permanent set in fatigue even when they are wetted and such that the absorption spaces, in which the body fluid is to be stored temporarily, can be kept stable. By the combination of the absorbent polymer 2b, which has a high retentive capacity and good permeability after swelling and which satisfies the absorption physical properties described above, and the cellulose fibers 2a, it becomes possible to obtain effects better than effects obtained when the absorbent polymer 2b or the crosslinked cellulose fibers 2a are used alone.

The cellulose fibers 2a will be described hereinbelow.

As illustrated in FIG. 1, the cellulose fibers 2a may be directly mixed with the absorbent polymer 2b in order to constitute the absorbent member. Alternatively, as in the second, third, fourth, and fifth embodiments illustrated in FIGS. 2, 3, 4, and 6, an absorbent paper comprising the cellulose fibers 2a may be prepared and used in order to constitute the absorbent member.

The crosslinked cellulose fibers used in the present invention are obtained from the intramolecular and/or intermolecular crosslinking of cellulose fibers having a degree of fiber roughness of 0.3 mg/m or more.

As the cellulose fibers, it is possible to use any of natural cellulose fibers, such as wood pulp or cotton, and regenerated cellulose fibers, such as rayon and cupra. From the viewpoint of cost, the wood pulp should preferably be used, and particularly soft-wood pulp (e.g., NBKP) can be used favorably. These cellulose fibers may be used alone or as a mixture of two or more of them.

Examples of the crosslinking agents used in order to crosslink the cellulose fibers include N-methylol compounds, such as dimethylolethyleneurea and dimethyloldihydroxyethyleneurea; polycarboxylic acids, such as citric acid, tricarballylic acid, and butanetetracarboxylic acid; polyols, such as dimethylhydroxyethyleneurea; and polyglycidyl ethers. The above-enumerated crosslinking agents may be used alone or as a mixture of two or more of them.

The amount of the crosslinking agent used should preferably fall within the range of 0.2 to 20 parts by weight per 100 parts by weight of the cellulose fibers. If the amount of the crosslinking agent used is smaller than 0.2 part by weight per 100 parts by weight of the cellulose fibers, the crosslinking density will become very low. Therefore, the modulus of elasticity in a wet state will become low, and the twist and permanent set in fatigue will occur with the crosslinked cellulose fibers. If the amount of the crosslinking agent used is larger than 20 parts by weight per 100 parts by weight of the cellulose fibers, the cellulose fibers will become very rigid and will become brittle when being subjected to stress.

Crosslinking of the cellulose fibers with the crosslinking agent may be carried out by, for example, adding a catalyst, if necessary, to an aqueous solution of the crosslinking agent, impregnating the cellulose fibers with the aqueous solution of the crosslinking agent, and heating the cellulose fibers to a crosslinking temperature.

The crosslinked cellulose fibers used in the present invention are obtained from the intramolecular and/or intermolecular crosslinking of the cellulose fibers. By virtue of the crosslinked structure, the twist and permanent set in fatigue do not occur with the cellulose fibers even when they are wetted. Also, the crosslinked cellulose fibers by themselves do not absorb liquid, and therefore do not swell. In the present invention, by virtue of the synergistic effects obtained from these two features, even if the crosslinked cellulose fibers are wetted with liquid, the distance between the fibers can be reliably kept stable. Therefore, in the present invention, the crosslinked cellulose fibers should preferably be obtained by carrying out both the crosslinking in the cellulose molecule and the crosslinking between the cellulose molecules.

Most of the conventional wood pulp fibers have a degree of fiber roughness of lower than 0.3 mg/m. Even if the conventional wood pulp fibers are crosslinked, sufficient effects of the crosslinking cannot be obtained. However, the study carried out by the inventors revealed that the effects described above can be enhanced even further by carrying out the crosslinking of pulp fibers having a degree of fiber roughness of 0.3 mg/m or more.

Therefore, in the present invention, the cellulose fibers having a degree of fiber roughness of 0.3 mg/m or more should preferably be subjected to the crosslinking. The degree of fiber roughness of the cellulose fibers subjected to the crosslinking should more preferably fall within the range of 0.3 to 2 mg/m, and should most preferably fall within the range of 0.33 to 1 mg/m. If the degree of fiber roughness of the cellulose fibers subjected to the crosslinking is lower than 0.3 mg/m, the cellulose fibers will be very thin and flexible, and therefore the effects of the crosslinking cannot be obtained easily. If the degree of fiber roughness of the cellulose fibers subjected to the crosslinking is higher than 2 mg/m, the cellulose fibers will often become very rigid.

In the present invention, the degree of fiber roughness is used as a measure for indicating the fiber thickness in the fibers, such as wood pulp, which have nonuniform fiber thickness. By way of example, the degree of fiber roughness can be measured by using a fiber roughness meter available under the trade name "FS-200" (supplied by KAJAANI ELECTRONICS LTD.).

Examples of the cellulose fibers having a degree of fiber roughness of 0.3 mg/m or more include softwood kraft pulp available under the trade name "ALBACEL" (supplied by Federal Paper Board Co.), and under the trade name "INDORAYON" (supplied by PT Inti Indorayon Utama).

In general, in an absorbent paper, the resistance to transfer of liquid through the absorbent paper becomes lower as the cross-sectional shape of the fiber is closer to the true circle. Therefore, in the present invention, the cross-sectional shape of the cellulose fibers, which are subjected to the crosslinking, should preferably be as close to the true circle as possible. Specifically, a degree of fiber roundness (a roundness of the fiber cross section) of the cellulose fibers should preferably be 0.5 or more, and should more preferably fall within the range of 0.55 to 1. In the present invention, more advantageous effects can be obtained, in particular, in cases where the cellulose fibers, which are subjected to the crosslinking, have the degree of fiber roughness of 0.3 mg/m or more and, at the same time, have the degree of fiber roundness of 0.5 or more.

As described above, in the present invention, as the cellulose fibers, wood pulp fibers should preferably be used. In general, the wood pulp fibers have a flat cross-sectional shape due to delignification and a degree of fiber roundness of lower than 0.5. In order for the wood pulp fibers to have the degree of fiber roundness of 0.5 or more, for example, the wood pulp fibers may be subjected to mercerization, and the cross section of the wood pulp fibers may thereby be swollen.

As described above, as the crosslinked cellulose fibers employed in the present invention, mercerized crosslinked pulp fibers, which are obtained by crosslinking the mercerized pulp fibers obtained from mercerization of ordinary wood pulp fibers and having a degree of fiber roundness of 0.5 or more.

By way of example, the mercerized crosslinked pulp fibers can be obtained by mercerizing the wood pulp fibers, which have a degree of fiber roughness of 0.3 mg/m or more, thereby enhancing the degree of fiber roundness of the wood pulp fibers, and thereafter crosslinking the mercerized wood pulp fibers. Alternatively, the mercerized crosslinked pulp fibers may be obtained by crosslinking the commercially available mercerized pulp fibers.

Examples of the commercially available mercerized pulp fibers, which may be employed in the present invention, include the trade name "FILTRANIER" (supplied by ITT Rayonier Inc.) and the trade name "POROSANIER" (supplied by ITT Rayonier Inc.).

The crosslinked cellulose fibers used in the present invention should preferably undergo little twist and little permanent set in fatigue even when being wetted with liquid. Specifically, the residual strain after compression of the bulky crosslinked cellulose fibers in a wet state should preferably be low. The residual strain after compression should preferably be as low as possible. Specifically, the residual strain after compression of the bulky crosslinked cellulose fibers in a wet state should preferably be lower than 40%, and should more preferably be lower than 35%. If the residual strain after compression of the crosslinked cellulose fibers in a wet state is 40% or higher, the liquid absorption rate and the liquid absorption capacity will decrease, and the twist and permanent set in fatigue will become large when the fibers are wetted. As a result, the liquid absorption spaces will decrease, the distance between the fibers will become short, and it will become difficult to keep the crosslinked cellulose fibers stable.

In order that the residual strain after compression of the cellulose fibers in a wet state may be reliably kept to be lower than 40%, and in order that the distance between the cellulose fibers may be kept stable, the thickness of the crosslinked cellulose fibers should preferably be adjusted in addition to the crosslinking of the cellulose fibers. This is because it becomes easier to stabilize the residual strain after compression of the crosslinked cellulose fibers in a wet state at a low value and the distance between fibers can be more reliably prevented from decreasing as the thickness of the crosslinked cellulose fibers becomes larger. The thickness of the crosslinked cellulose fibers depends on the thickness of the cellulose fibers, which are subjected to the crosslinking. Therefore, in order for the thickness of the crosslinked cellulose fibers to be adjusted, the thickness of the cellulose fibers, which are subjected to the crosslinking, may be adjusted appropriately. As described above, the degree of fiber roughness serves as a measure for the thickness of the fiber. Therefore, in the present invention, it is preferable to use the crosslinked cellulose fibers obtainable from the intramolecular and/or intermolecular crosslinking of cellulose fibers having a degree of fiber roughness of 0.3 mg/m or more, and which have a residual strain after compression in a wet state of lower than 40%. It is particularly preferable to use the crosslinked cellulose fibers obtainable from the intramolecular and/or intermolecular crosslinking of cellulose fibers having a degree of fiber roughness of 0.3 mg/m or more and having a degree of fiber roundness of 0.5 or more, and which have a residual strain after compression in a wet state of lower than 40%.

In the foregoing explanation, the thickness of the cellulose fibers is expressed by the degree of fiber roughness. In cases where the fiber cross-sectional area of the cellulose fibers can be measured, the fiber cross-sectional area may be employed in order to express the thickness of the cellulose fibers in lieu of the degree of fiber roughness. In cases where the thickness of the cellulose fibers is expressed by the fiber cross-sectional area, the fiber cross-sectional area of the cellulose fibers employed in the present invention should preferably be $3\times10^{-6}$ cm$^2$ or more, and should more preferably be $5\times10^{-6}$ cm$^2$ or more.

The fiber cross-sectional area of the cellulose fibers can be measured in the manner described below. Specifically, the cellulose fiber is sliced along a plane perpendicular to the longitudinal direction of the fiber such that the area of the cross section of the fiber may not change. A photograph of the cross section of the cellulose fiber is then taken by using an electron microscope. Thereafter, the photograph of the cross section of the cellulose fiber is set in an image analyzer "Avio EXCEL" (supplied by Nippon Avionics Co., Ltd.), and the cross-sectional area of the cellulose fiber is thereby measured. One hundred fiber cross sections are taken arbitrarily, their cross-sectional areas are measured, and the mean value of the values of the measured cross-sectional areas is taken as the fiber cross-sectional area of the cellulose fibers.

In the sanitary napkin 10 shown in FIG. 1, the absorbent member 2 further comprises an absorbent paper 2c comprising the crosslinked cellulose fibers. The absorbent paper 2c is preferably located at the outermost part of the absorbent member 2 and is preferably constituted of a permeable absorbent paper, which has a high body fluid absorption and permeation rate.

The permeable absorbent paper, which is employed in the present invention, comprises 50 to 98 parts by weight, preferably 70 to 98 parts by weight, of the crosslinked cellulose fibers described above and 2 to 50 parts by weight, preferably 2 to 30 parts by weight, of thermally fusible bonding fibers, and has a basis weight of 20 to 60 g/m$^2$, preferably 20 to 50 g/m$^2$. In the permeable absorbent paper, if the proportion of the crosslinked cellulose fibers is lower than 50 parts by weight, the permeation rate of the obtained permeable absorbent paper will become insufficient. If the proportion of the crosslinked cellulose fibers in the permeable absorbent paper is larger than 98 parts by weight, it will become difficult to form a sheet of the permeable absorbent paper. Also, in the permeable absorbent paper, if the proportion of the thermally fusible bonding fibers is lower than 2 parts by weight, the strength of the permeable absorbent paper will become insufficient, and it will become difficult to form a sheet of the permeable absorbent paper. If the proportion of the thermally fusible bonding fibers in the permeable absorbent paper is larger than 30 parts by weight, the permeability of the permeable absorbent paper will often become low.

As the thermally fusible bonding fibers, it is possible to employ the fibers, which melt with heat and adhere to one another. Examples of the thermally fusible bonding fibers include polyolefin fibers, such as polyethylene fibers, polypropylene fibers, and polyvinyl alcohol fibers; polyester fibers, polyethylene-polypropylene composite fibers, polyethylene-polyester composite fibers, low melting point polyester-polyester composite fibers, polyvinyl alcohol-polypropylene composite fibers, which have hydrophilic fiber surfaces, and polyvinyl alcohol-polyester composite fibers. In cases where the composite fibers are used, they may be of the core-sheath type or of the side-by-side type. The above-enumerated thermally fusible bonding fibers may be used along or as a mixture of two or more of them. In the present invention, polyvinyl alcohol fibers, polyester fibers, and the like, are preferably used as the thermally fusible bonding fibers.

In general, the thermally fusible bonding fibers have a fiber length falling within the range of 2 to 60 mm and a fiber fineness falling within the range of 0.5 to 3 denier.

No limitation is imposed on how the permeable absorbent paper is produced. For example, the wet type of or dry type of paper preparing process, which is ordinary carried out, may be employed. In cases where the wet type of paper preparing process is employed, the crosslinked cellulose fibers and the thermally fusible bonding fibers are dispersed in water, other constituents are added if necessary, a slurry is thus prepared, and a paper is prepared from the slurry by using a paper machine. Thereafter, if necessary, the paper may be subjected to a calendering process or a crepe process.

Examples of the other constituents, which may be added to the dispersion of the crosslinked cellulose fibers and the thermally fusible bonding fibers in water, include other pulp, such as softwood pulp, hardwood pulp, and straw pulp; and tenacity assisting agents, such as dialdehyde starch, sponge and carboxymethylcellulose sodium. The other constituents may be added in a proportion falling within the range of 0 to 20 parts by weight.

The permeable absorbent paper, which has been prepared in the manner described above, should preferably have a thickness under a load of 2.5 g/m$^2$ falling within the range of 0.2 to 2.0 mm. If the thickness under a load of 2.5 g/m$^2$ of the permeable absorbent paper is smaller than 0.2 mm, the absorption and permeation spaces for temporarily absorbing the body fluid will be small and insufficient. If the thickness under a load of 2.5 g/m$^2$ of the permeable absorbent paper is larger than 2.0 mm, it will become difficult to achieve smooth transfer of the body fluid to the lower layer side of the permeable absorbent paper. The thickness under a load of 2.5 g/m$^2$ of the permeable absorbent paper should more preferably fall within the range of 0.3 to 1.5 mm.

Also, in the present invention, the permeable absorbent paper should preferably have a short liquid permeation time. In particular, the permeable absorbent paper should preferably have a permeation time for 10 g of an 85% by weight aqueous glycerol solution of 50 seconds or less, and should more preferably have a permeation time for 10 g of an 85% by weight aqueous glycerol solution falling within the range of 5 to 40 seconds. If the permeation time is longer than 50 seconds, it will become difficult for the liquid to be transferred quickly through the permeable absorbent paper, and the liquid will often remain stagnant for a long time on the surface of the permeable absorbent paper without being absorbed into the permeable absorbent paper. From the viewpoint of quick liquid permeation, in addition to the permeation time of the level described above, the permeable absorbent paper should more preferably have the thickness falling within the range described above. How the permeation time is measured will be described later.

Particularly, the permeable absorbent paper is preferably provided at the uppermost layer of the liquid retentive absorbent member which is in contact with the permeable topsheet in an absorbent article so that the permeable absorbent paper may exhibit its performance. In this constitution, the permeable absorbent paper is preferred to have a function of transferring the body fluid, such as absorbing the body fluid from the topsheet and permeating it to the liquid retentive absorbent member as well as permeation of the body fluid. That is, the paper is preferred not only to allow the body fluid to pass in a short time but to first absorb the body fluid from the topsheet. Accordingly, the permeable absorbent paper according to the present invention has an absorption height after 1 minute absorption of physiological saline by Klemm's Method is preferably 20 to 80 mm, and more preferably 30 to 70 mm, and absorption height after 10 minutes absorption of physiological saline by Klemm's Method is preferably 30 to 120 mm, and still preferably 40 to 100 mm. If the absorption height is less than 20 mm, the paper unpreferably exhibits poor capability of absorbing the body fluid from the topsheet, causes the body fluid to remain stagnant in the topsheet to make the user to feel stickiness, or causes the body fluid to flow on the topsheet to leak. If the absorption height is more than 80 mm, the paper unpreferably exhibits insufficiency in permeability of the permeable absorbent paper, or causes the body fluid to disperse excessively in the uppermost layer of the liquid retentive absorbent member to otherwise leak. How the absorbent height by Klemm's Method is measured will be described later.

Most of the conventional absorbent paper sheets, which are used in absorbent articles, are prepared with a wet process from natural pulp such as ordinary softwood pulp. In cases where the absorbent paper is prepared with the wet process from natural pulp, when water is removed from the paper layer and the paper layer is dried during the dehydration, wet pressurization, and drying steps, very strong tightening force acts between the pulp fibers due to water interfacial tension and hydrogen bonding, which act between the pulp fibers. The distance between the pulp fibers becomes short due to the tightening force. Therefore, with the conventional absorbent paper, the liquid absorption and permeation become very slow. Also, with the conventional absorbent paper, the liquid absorption spaces reduce, and therefore the liquid permeability becomes low.

On the other hand, with the permeable absorbent paper used in the present invention, because the crosslinked cellulose fibers are blended, the hydrogen bonding, which acts between the fibers during the wet type of paper preparation, can be restricted, and the tightening force acting between the fibers can thereby be weakened. As a result, the liquid absorption spaces can be kept large, and the liquid flow for liquid absorption, permeation, and diffusion can be controlled.

A second embodiment of the absorbent article in accordance with the present invention, which is constituted as a sanitary napkin, will be described hereinbelow with reference to FIG. 2.

The same features as those in the first embodiment described above will not be described in detail hereinbelow, and the explanation with respect to the aforesaid embodiment is also applied to the second embodiment. In FIG. 2, similar elements are numbered with the same reference numerals with respect to FIG. 1.

Figure 2:
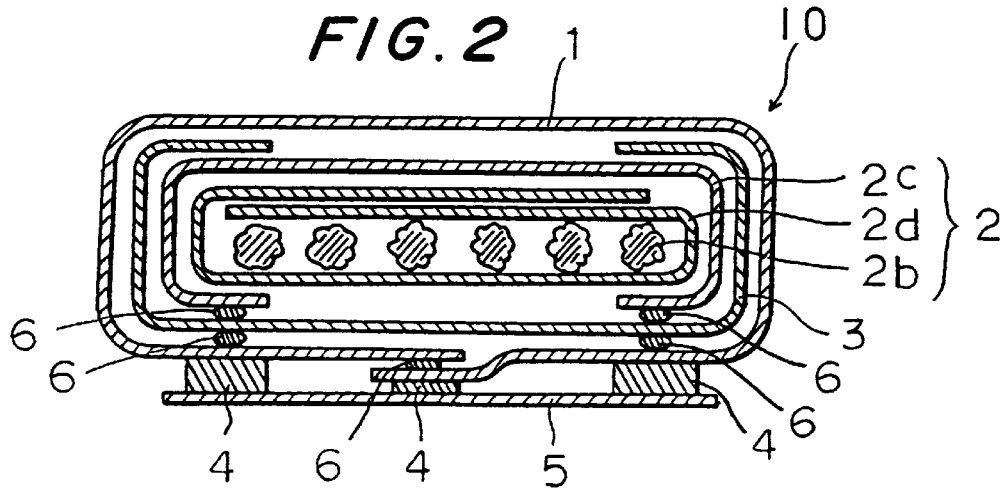
FIG. 2 is a sectional view showing a second embodiment of the absorbent article in accordance with the present invention, which is constituted as a sanitary napkin, the sectional view being taken along the transverse direction of the sanitary napkin.

In a sanitary napkin 10 shown in FIG. 2, an absorbent member 2 comprises the absorbent polymer 2b described above, a diffusing absorbent paper 2d, which covers the absorbent polymer 2b, and the permeable absorbent paper 2c, which covers the front surface (i.e., the surface on the side in contact with the user's skin), the side surfaces, and the peripheral portions of the back surface of the diffusing absorbent paper 2d, and which constitutes the top layer of the absorbent member 2.

The diffusing absorbent paper 2d is located in order to quickly diffuse the body fluid, which has permeated through the permeable absorbent paper 2c, to the entire absorbent polymer 2b and thereby to smoothly transfer the body fluid to the absorbent polymer 2b. Specifically, as the diffusing absorbent paper 2d, the absorbent paper having the composition and the physical properties described below can be utilized favorably.

The diffusing absorbent paper, which is used in the present invention, comprises 20 to 80 parts by weight, preferably 30 to 70 parts by weight, of the crosslinked cellulose fibers described above, 80 to 20 parts by weight, preferably 70 to 30 parts by weight, of hydrophilic fine fibers, and 0 to 30 parts by weight, preferably 0 to 20 parts by weight, of thermally fusible bonding fibers, and has a basis weight of 20 to 60 g/m$^2$, preferably 20 to 50 g/m$^2$. In the diffusing absorbent paper, if the proportion of the crosslinked cellulose fibers is lower than 20 parts by weight, or if the proportion of the hydrophilic fine fibers is higher than 80 parts by weight, strong tightening force will act between the fibers during the paper preparation, and the liquid absorption spaces become small. Therefore, the permeation rate will become low, and the spaces capable of substantially diffusing the liquid will become small. Also, in the diffusing absorbent paper, if the proportion of the crosslinked cellulose fibers is higher than 80 parts by weight, or if the proportion of the hydrophilic fine fibers is lower than 20 parts by weight, the distance between the fibers will become long, and therefore the capacity for diffusing the body fluid will become insufficient. In addition, because the diffusing capacity becomes low, the body fluid cannot be smoothly transferred from the permeable absorbent paper to the diffusing absorbent paper.

As the crosslinked cellulose fibers contained in the diffusing absorbent paper, the same crosslinked cellulose fibers as those used in the aforesaid permeable absorbent paper may be used. Alternatively, crosslinked cellulose fibers different from those used in the aforesaid permeable absorbent paper may be used in the diffusing absorbent paper. In the present invention, the crosslinked cellulose fibers used in the permeable absorbent paper and the crosslinked cellulose fibers used in the diffusing absorbent paper should preferably be of the same kind.

As the hydrophilic fine fibers, fibers having hydrophilic fiber surfaces and large fiber surface areas can be used. The hydrophilic fine fibers should preferably have a degree of fiber roughness of lower than 0.2 mg/m, and should more preferably have a degree of fiber roughness falling within the range of 0.01 to 0.2 mg/m. Also, the hydrophilic fine fibers should preferably have a degree of fiber roundness of lower than 0.5, and should more preferably have a degree of fiber roundness falling within the-range of 0.1 to 0.4. Or, the hydrophilic fine fibers should preferably have a fiber surface area of 1.0 m$^2$/g or more, and should more preferably have a fiber surface area falling within the range of 1 to 20 m$^2$/g. The hydrophilic fine fibers ordinarily have a fiber length falling within the range of 0.5 to 15 mm.

As the hydrophilic fine fibers used in the present invention, any of fibers having the physical properties described above can be used. Examples of the hydrophilic fine fibers include cellulose fibers, such as wood pulp fibers, cotton fibers, and rayon fibers; and synthetic fibers having hydrophilic groups, such as acrylonitrile fibers, and polyvinyl alcohol fibers. Among these fibers, the wood pulp fibers are advantageous in that they are available at a low cost, and in that the fiber surface area can be controlled by the control of beating conditions and by carrying out mercerization. Examples of such wood pulp fibers include NBKP (e.g., trade name "SKEENA PRIME" supplied by Skeena Cellulose Co.), which has been finely beaten, LBKP (trade name "PRIME ALBERT ASPEN HARDWOOD" supplied by Weyerhauser Paper), and straw pulp fibers. The above-enumerated hydrophilic fine fibers may be used alone or as a mixture of two ore more of them.

Also, the diffusing absorbent paper should preferably contain up to 30 parts by weight of the thermally fusible bonding fibers. If the proportion of the thermally fusible bonding fibers is larger than 30 parts by weight, the hydrophilicity of the diffusing absorbent paper will become low, and the liquid diffusing capacity and the liquid permeability will often become low. Addition of the thermally fusible bonding fibers to the diffusing absorbent paper further enhances the effects of stabilizing the fiber spaces in a wet state. The diffusing absorbent paper should more preferably contain up to 20 parts by weight of the thermally fusible bonding fibers, and should most preferably contain 2 to 20 parts by weight of the thermally fusible bonding fibers. As the thermally fusible bonding fibers, the same thermally fusible bonding fibers as those described above with respect to the permeable absorbent paper can be used. In such cases, the thermally fusible bonding fibers used in the permeable absorbent paper and the thermally fusible bonding fibers used in the diffusing absorbent paper may be of the same kind or may be of different kinds. In the present invention, the thermally fusible bonding fibers used in the permeable absorbent paper and the thermally fusible bonding fibers used in the diffusing absorbent paper should preferably be of the same kind.

No limitation is imposed on how the diffusing absorbent paper is produced. For example, the wet type of or dry type of paper preparing process, which is ordinary carried out, may be employed. In cases where the wet type of paper preparing process is employed, the crosslinked cellulose fibers, hydrophilic fine fibers, and the thermally fusible bonding fibers are dispersed in water, other constituents are added if necessary, a slurry is thus prepared, and a paper is prepared from the slurry by using a paper machine. Thereafter, if necessary, the paper may be subjected to a calendering process or a crepe process.

Examples of the other constituents, which may be added to the dispersion of the crosslinked cellulose fibers, include other pulps such as softwood kraft pulp, hardwood kraft pulp and straw pulp, and strong assistant agents such as dialdehyde starch, sponge and carboxymethyl cellulose sodium salt. The other constituents may be added in a proportion falling within the range of 0 to 20 parts by weight.

The diffusing absorbent paper, which has been prepared in the manner described above, should preferably have a thickness under a load of 2.5 g/m² falling within the range of 0.2 to 0.8 mm. If the thickness under a load of 2.5 g/m² of the diffusing absorbent paper is smaller than 0.2 mm, the spaces for diffusing the body fluid will be small and the diffusing capacity will become insufficient. If the thickness under a load of 2.5 g/m² of the diffusing absorbent paper is larger than 0.8 mm, it will become difficult to achieve transfer of the body fluid to the absorbent polymer due to the excessive thickness. The thickness under a load of 2.5 g/m² of the diffusing absorbent paper should more preferably fall within the range of 0.3 to 0.6 mm.

In the present invention, the diffusing absorbent paper is required to have the functions for quickly diffusing the liquid over a wide area. Therefore, the diffusing absorbent paper should preferably have an absorption height after 1 minute absorption of physiological saline by Klemm's Method of 50 mm or more, and an absorption height after 10 minutes absorption of physiological saline by Klemm's Method of 100 mm or more. If these absorption heights by Klemm's Method are lower than the defined values, the liquid diffusing capacity will become low. The diffusing absorbent paper should more preferably have an absorption height after 1 minute absorption of physiological saline by Klemm's Method falling within the range of 60 to 120 mm. Also, the diffusing absorbent paper should more preferably have an absorption height after 10 minutes absorption of physiological saline by Klemm's Method falling within the range of 120 to 300 mm. How the absorption height by Klemm's Method is measured will be described later.

As described above, the it is necessary for the diffusing absorbent paper to have the function for quickly diffusing the liquid. In addition, the diffusing absorbent paper should exhibit a high liquid absorption rate. Specifically, the diffusing absorbent paper should preferably have a permeation time for 10 g of an 85% by weight aqueous glycerol solution of 100 seconds or less, and should more preferably have a permeation time for 10 g of an 85% by weight aqueous glycerol solution falling within the range of 10 to 80 seconds. The diffusing absorbent paper having such characteristics can exhibit particularly excellent performance with respect to the liquid diffusion and absorption.

A third embodiment of the absorbent article in accordance with the present invention, which is constituted as a sanitary napkin, will be described hereinbelow with reference to FIG. 3.

The same features as those in the first embodiment described above will not be described in detail hereinbelow, and the explanation with respect to the aforesaid embodiment is also applied to the third embodiment. In FIG. 3, similar elements are numbered with the same reference numerals with respect to FIG. 1.

Figure 3:
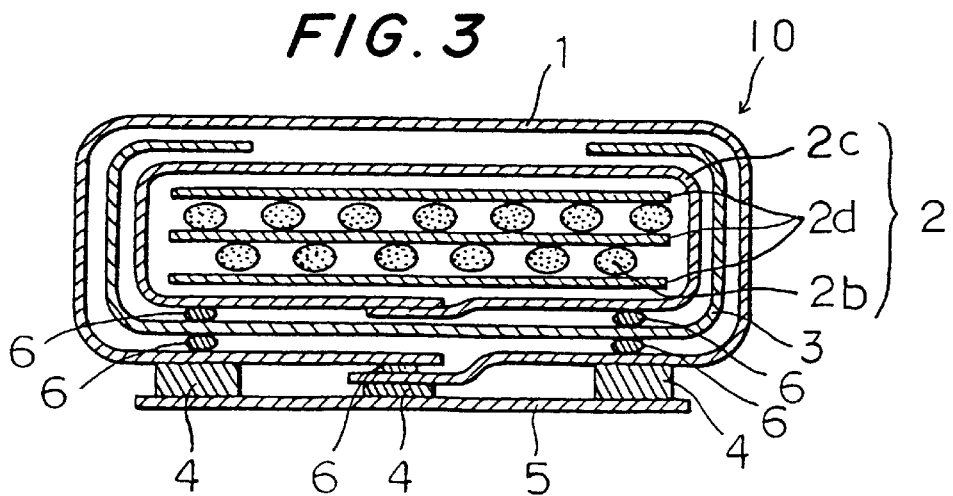
FIG. 3 is a sectional view showing a third embodiment of the absorbent article in accordance with the present invention, which is constituted as a sanitary napkin, the sectional view being taken along the transverse direction of the sanitary napkin.

In a sanitary napkin 10 shown in FIG. 3, an absorbent member 2 comprises a plurality of (in this case, three) sheets of the diffusing absorbent paper 2d, which sandwich the absorbent polymer 2b therebetween. Thus particles of the absorbent polymer 2b are spread between the diffusing absorbent papers. The entire surfaces of the combination of the absorbent polymer 2b and the sheets of the diffusing absorbent paper 2d are covered with the permeable absorbent paper 2c. In this manner, the absorbent polymer 2b, the sheets of the diffusing absorbent paper 2d, and the permeable absorbent paper 2c are combined with one another into a unitary body.

As described above with reference to the second and third embodiments, no limitation is imposed on how the absorbent polymer 2b and the diffusing absorbent paper 2d, which has a high diffusing capacity and a high permeability, are combined with each other.

A fourth embodiment of the absorbent article in accordance with the present invention, which is constituted as a sanitary napkin, will be described hereinbelow with reference to FIGS. 4 and 5.

The same features as those in the first embodiment described above will not be described in detail hereinbelow, and the explanation with respect to the aforesaid embodiment is also applied to the fourth embodiment. In FIGS. 4 and 5, similar elements are numbered with the same reference numerals with respect to FIG. 1.

Figure 4:
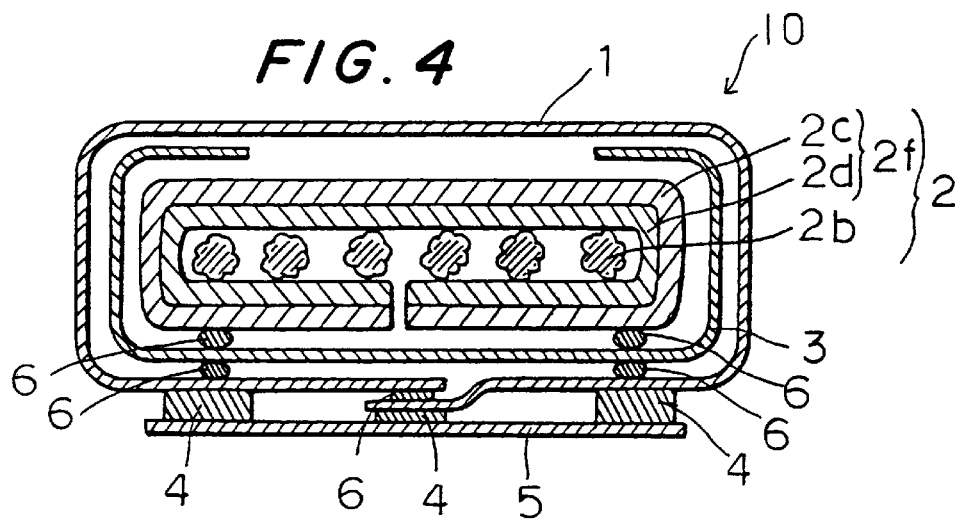
FIG. 4 is a sectional view showing a fourth embodiment of the absorbent article in accordance with the present invention, which is constituted as a sanitary napkin, the sectional view being taken along the transverse direction of the sanitary napkin.

In a sanitary napkin 10 shown in FIG. 4, an absorbent member 2 comprises the absorbent polymer 2b and a composite absorbent paper 2f, which includes and covers the absorbent polymer 2b.

Figure 5:
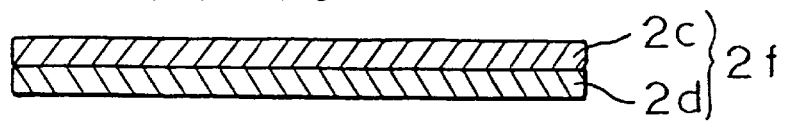
FIG. 5 is an enlarged view showing a composite absorbent paper, which is employed in the embodiment of FIG. 4.

As illustrated in FIG. 5, the composite absorbent paper 2f comprises the permeable absorbent paper 2c described above and the diffusing absorbent paper 2d described above, which are combined with each other into a unitary body. The composite absorbent paper 2f includes and covers the absorbent polymer 2b such that the side of the diffusing absorbent paper 2d may come into contact with the absorbent polymer 2b.

No limitation is imposed on how the permeable absorbent paper and the diffusing absorbent paper are combined with each other into a unitary body.

For example, the permeable absorbent paper and the diffusing absorbent paper may be overlaid one upon the other, may then be passed between a pair of embossing rolls, and may thereby be combined with each other into a unitary body. Alternatively, the permeable absorbent paper and the diffusing absorbent paper may be combined together by using an adhesive agent or a pressure sensitive adhesive, typically a hot melt, or the like. In the present invention, a method should preferably be employed wherein the permeable absorbent paper and the diffusing absorbent paper are prepared with a wet type of paper preparing process and successively combined together in the paper preparing step.

With such a method, the fibers of the permeable absorbent paper and the fibers of the diffusing absorbent paper interlock with each other more tightly such that the liquid can be transferred smoothly therebetween.

As an example of the method for combining the permeable absorbent paper and the diffusing absorbent paper in the paper preparing step, a slurry for the formation of the permeable absorbent paper is fed to a paper machine, and a paper layer is formed on a wire. Also, a slurry for the formation of the diffusing absorbent paper is independently fed to a different paper machine, and a paper layer is formed on wires.

The two paper layers are then taken up from the wires, overlaid one upon the other, pressed, dehydrated, and dried. In this manner, the composite absorbent paper comprising the permeable absorbent paper and the diffusing absorbent paper, which have been combined with each other into a unitary body, can be obtained.

As a different example of the method for combining the permeable absorbent paper and the diffusing absorbent paper in the paper preparing step, a slurry for the formation of the permeable absorbent paper and a slurry for the formation of the diffusing absorbent paper are fed simultaneously from two rows of paper preparing nozzles onto a wire, and two paper layers overlaid one upon the other are thereby formed. The paper layers are then taken up from a wire, pressed, dehydrated, and dried. In this manner, the composite absorbent paper comprising the permeable absorbent paper and the diffusing absorbent paper, which have been combined with each other into a unitary body, can be obtained.

In the manner described above, the permeable absorbent paper and the diffusing absorbent paper are combined with each other into a unitary body. Therefore, the body fluid does not remain stagnant between the two absorbent paper sheets, can be smoothly guided to the absorbent polymer, and can thereby be immobilized reliably. Specifically, if the two absorbent paper sheets are separated from each other, the body fluid will remain stagnant between the two absorbent paper sheets and cannot be transferred to the absorbent polymer. However, as illustrated in FIG. 4, in cases where the composite absorbent paper, which comprises the permeable absorbent paper and the diffusing absorbent paper combined with each other into a unitary body, is combined with the absorbent polymer, the body fluid having been absorbed by the permeable absorbent paper and having permeated through it can be smoothly absorbed into the region inside of the absorbent member without remaining stagnant between the absorbent paper sheets. Also, the body fluid can be diffused by the diffusing absorbent paper over the entire absorbent member and can thus be perfectly immobilized by the absorbent polymer.

Also, in cases where the composite absorbent paper constituted in the manner described above is used, the absorbent member can be constituted of only the single sheet of absorbent paper and the absorbent polymer. Therefore, the absorbent member, which has a high absorbency and is very thin, can be obtained very easily.

A fifth embodiment of the absorbent article in accordance with the present invention, which is constituted as a sanitary napkin, will be described hereinbelow with reference to FIGS. 6 and 7.

The same features as those in the first embodiment described above will not be described in detail hereinbelow, and the explanation with respect to the aforesaid embodiment is also applied to the fifth embodiment. In FIGS. 6 and 7, similar elements are numbered with the same reference numerals with respect to FIG. 1.

Figure 6:
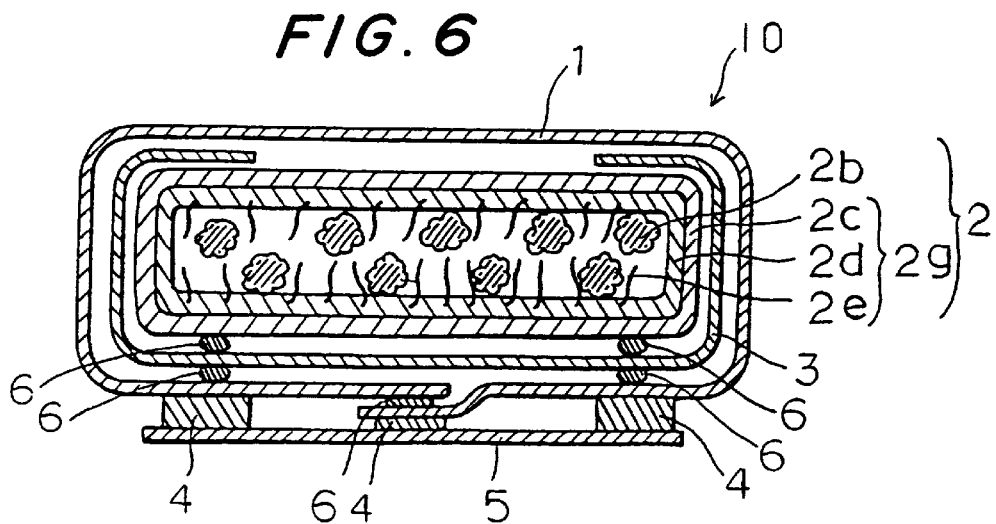
FIG. 6 is a sectional view showing a fifth embodiment of the absorbent article in accordance with the present invention, which is constituted as a sanitary napkin, the sectional view being taken along the transverse direction of the sanitary napkin.

In a sanitary napkin 10 shown in FIG. 6, an absorbent member 2 comprises the absorbent polymer 2b and a composite absorbent paper 2g, which includes the absorbent polymer 2b.

Figure 7:
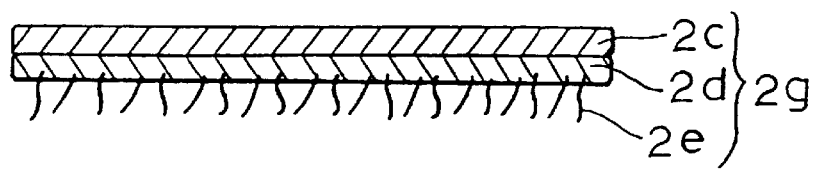
FIG. 7 is an enlarged view showing a composite absorbent paper, which is employed in the embodiment of FIG. 6.

As illustrated in FIG. 7, the composite absorbent paper 2g comprises the permeable absorbent paper 2c described above, the diffusing absorbent paper 2d described above, and a polymer dispersing paper 2e, which are combined with one another in this order into a unitary body. The composite absorbent paper 2g includes and covers the absorbent polymer 2b such that the side of the polymer dispersing paper 2e may come into contact with the absorbent polymer 2b.

The polymer dispersing paper 2e serves to prevent the particles of the absorbent polymer from agglomerating even when a large amount of the absorbent polymer is applied to the composite absorbent paper to form a unitary body as shown in FIG. 6. Therefore, with the polymer dispersing paper 2e, the gel blocking phenomenon of the absorbent polymer can be restricted more efficiently, and the liquid passing performance between the particles of the absorbent polymer can be improved even further.

The polymer dispersing paper should preferably be constituted primarily of the aforesaid crosslinked cellulose fibers, which do not undergo permanent set in fatigue even when being wetted, and should preferably has a low density and fuzz such that the absorbent polymer can be embedded. Specifically, the polymer dispersing paper should preferably contain 70 to 100 parts by weight, more preferably 80 to 100 parts by weight, of the aforesaid crosslinked cellulose fibers and 0 to 30 parts by weight, more preferably 0 to 20 parts by weight, of the thermally fusible bonding fibers. Also, the polymer dispersing paper should preferably has a basis weight falling within the range of 10 to 50 g/m$^2$, and should more preferably has a basis weight falling within the range of 10 to 30 g/m$^2$.

As the crosslinked cellulose fibers contained in the polymer dispersing paper, the same crosslinked cellulose fibers as those used in the aforesaid permeable absorbent paper and the aforesaid diffusing absorbent paper may be used. In such cases, the crosslinked cellulose fibers used in the polymer dispersing paper, the crosslinked cellulose fibers used in the permeable absorbent paper, and the crosslinked cellulose fibers used in the diffusing absorbent paper may be of the same kind or may be of different kinds. Also, the crosslinked cellulose fibers used in the two of these three components may be of the same kind, and a different kind of crosslinked cellulose fibers may be used in the remaining component. In the present invention, the crosslinked cellulose fibers used in the three components should preferably be of the same kind.

In addition to the aforesaid crosslinked cellulose fibers, the polymer dispersing paper should preferably also contain up to 30 parts by weight of thermally fusible bonding fibers. The use of the thermally fusible bonding fibers in the polymer dispersing paper has the effects of even further stabilizing the distance between fibers in a wet state. The polymer dispersing paper should more preferably contain up to 20 parts by weight of the thermally fusible bonding fibers, and should most preferably contain 2 to 20 parts by weight of the thermally fusible bonding fibers. As the thermally fusible bonding fibers, the same thermally fusible bonding fibers as those described above with respect to the permeable absorbent paper and the diffusing absorbent paper can be used. In such cases, the thermally fusible bonding fibers used in the polymer dispersing paper, the thermally fusible bonding fibers used in the permeable absorbent paper, and the thermally fusible bonding fibers used in the diffusing absorbent paper may be of the same kind or may be of different kinds. Also, the thermally fusible bonding fibers used in the two of these three components may be of the same kind, and a different kind of thermally fusible bonding fibers may be used in the remaining component. In the present invention, the thermally fusible bonding fibers used in the three components should preferably be of the same kind.

No limitation is imposed on how the polymer dispersing paper is produced. For example, the wet type of or dry type of paper preparing process, which is ordinary carried out, may be employed. In cases where the wet type of paper preparing process is employed, the crosslinked cellulose fibers and, if necessary, the thermally fusible bonding fibers are dispersed in water, other constituents are added if necessary, a slurry is thus prepared, and a paper is prepared from the slurry by using a paper machine. Thereafter, if necessary, the paper may be subjected to a calendering process or a crepe process.

Examples of the other constituents, which may be added to the dispersion of the crosslinked cellulose fibers and, if necessary, the thermally fusible bonding fibers in water, include other pulps such as softwood kraft pulp, hardwood kraft pulp and straw pulps, and strong assistant agent such as dialdehyde starch, sponge and carboxymethylcellulose sodium. The other constituents may be added in a proportion falling within the range of 0 to 20 parts by weight.

The polymer dispersing paper, which has been prepared in the manner described above, should preferably have a thickness under a load of 2.5 $g/m^2$ falling within the range of 0.2 to 1.0 mm. If the thickness under a load of 2.5 $g/m^2$ of the polymer dispersing paper is smaller than 0.2 mm, the effects of dispersing the polymer will become insufficient. If the thickness under a load of 2.5 $g/m^2$ of the polymer dispersing paper is larger than 1.0 mm, the absorbent article cannot be kept very thin due to the excessive thickness of the polymer dispersing paper. The thickness under a load of 2.5 $g/m^2$ of the polymer dispersing paper should more preferably fall within the range of 0.2 to 0.6 mm.

In order to produce the composite absorbent paper, which is provided with the permeable absorbent paper, the diffusing absorbent paper, and the polymer dispersing paper, the aforesaid method for producing the composite absorbent paper, which is provided with the permeable absorbent paper and the diffusing absorbent paper, may be used.

In the present invention, it is particularly advantageous to use the absorbent member 2 having the configuration shown in FIG. 6 because the absorbent article having good absorption performance even under the conditions of large excretion amounts can be obtained.

A sixth embodiment of the absorbent article in accordance with the present invention, which is constituted as a sanitary napkin, will be described hereinbelow with reference to FIG. 8.

The same features as those in the first embodiment described above will not be described in detail hereinbelow, and the explanation with respect to the aforesaid embodiment is also applied to the sixth embodiment. In FIG. 8, similar elements are numbered with the same reference numerals with respect to FIG. 1.

Figure 8:
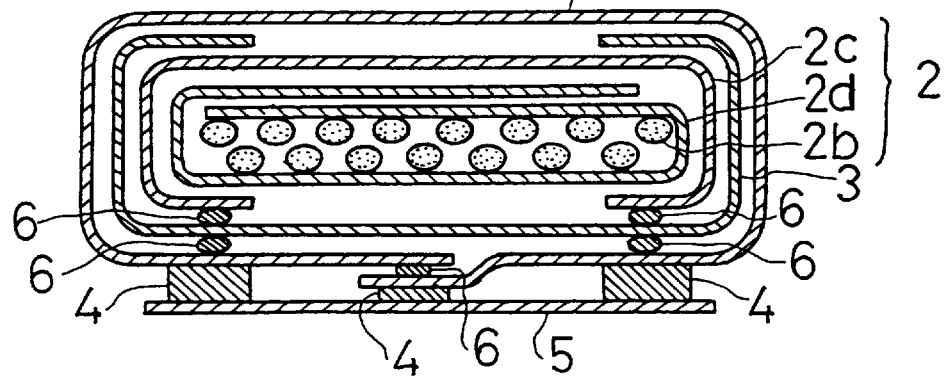
FIG. 8 is a sectional view showing a sixth embodiment of the absorbent article in accordance with the present invention, which is constituted as a sanitary napkin, the sectional view being taken along the transverse direction of the sanitary napkin.

With reference to FIG. 8, a sanitary napkin 10 is provided with an absorbent member 2. The absorbent member 2 has a centrifugal retentive capacity with respect to pseudo-blood, which is measured after equilibrium absorption swelling with the pseudo-blood, of 30 g or more, preferably falling within the range of 40 to 150 g. Also, the absorbent member 2 has a permeation rate with respect to pseudo-blood of 50 ml/minute or more, preferably falling within the range of 60 to 300 ml/minute, the permeation rate being measured by securing an absorbent member, which has a thickness of 0.5 to 5 mm, to an end of a cylinder having a cross-sectional area of 10 $cm^2$ (inner diameter: 35.8 mm), allowing the absorbent member to swell with pseudo-blood until the swelling reaches equilibrium, and thereafter causing pseudo-blood to permeate through the absorbent member.

The thickness of the absorbent member when being secured to the end of the cylinder depends on the thickness and composition of the absorbent member to be measured. However, the absorbent member is secured to the end of the cylinder such that the pseudo-blood may not leak from the side surface of the absorbent member. At the time of measurement, the clearance at the circumference of the cylinder is reduced little by little until no pseudo-blood oozes out from the side surface of the absorbent member, the absorbent member is then secured such that it may have the aforesaid thickness, and thereafter the permeation rate is measured.

If the centrifugal retentive capacity of the absorbent member 2 with respect to pseudo-blood is lower than 30 g, inhibition of reflow of the liquid from the absorbent member 2 to the surface and inhibition of liquid leakage under the conditions of large absorption amounts will become insufficient. Also, if the permeation rate of the absorbent member 2 with respect to pseudo-blood is lower than 50 ml/minute, the blood passing performance will become bad and, in particular, the reabsorption characteristics under the conditions of repeated excretion will become very bad.

The centrifugal retentive capacity of the absorbent member 2 with respect to pseudo-blood represents the amount of blood perfectly immobilized in (or secured to) the absorbent member 2. In order for the centrifugal retentive capacity of the absorbent member 2 with respect to pseudo-blood to be measured, the absorbent member is impregnated with the pseudo-blood and caused to sufficiently absorb and swell with the pseudo-blood (by being left to stand for 30 minutes). Thereafter, the absorbent member is centrifuged in order to separate the pseudo-blood, which has not been secured to the absorbent member, (i.e. the pseudo-blood which returns to the surface due to pressurization, or the like) from the absorbent member. At this time, the amount of the pseudo-blood retained by the absorbent member is measured.

As described above, it is the essential requirement for the absorbent member 2 to have both the high centrifugal retentive capacity with respect to pseudo-blood and the high permeation rate with respect to pseudo-blood after absorption of the pseudo-blood. If the absorbent member 2 has only either one of the high centrifugal retentive capacity and the high permeation rate, the desired effects of the present invention cannot be obtained.

In order that the absorbent member 2 may reliably immobilize blood and may prevent it from leaking even under the conditions of long-time use and large absorption amounts, it is important how the absorbent polymer can perfectly absorb and retain blood, in addition to the absorption of blood into physical spaces of pulp, or the like. Therefore, as for the absorption capacity of the absorbent member for immobilizing blood, not the apparent amount absorption into the fiber spaces of pulp, paper, or the like, but the substantial absorption and retention amount of the absorbent polymer is an important parameter.

Accordingly, in the present invention, the absorption and retention amount of the absorbent polymer 2 is evaluated in terms of the centrifugal retentive capacity with respect to pseudo-blood, which represents the amount of blood capable of being perfectly secured to the absorbent member.

Enhancement of the centrifugal retentive capacity can be achieved by increasing the amount of the absorbent polymer used. However, heretofore, when the amount of the absorbent polymer used is increased until a desired level of the centrifugal retentive capacity is obtained, problems have occurred in that the density of the polymer particles becomes very high. As a result, the spaces among the polymer particles are lost due to swelling with blood, and the blood absorbency during reabsorption becomes markedly low.

Further, even if the centrifugal retentive capacity of the entire absorbent member is improved by increasing the amount of the absorbent polymer used, the effects of the high absorbency of the entire polymer cannot been utilized efficiently due to the decrease in the reabsorption performance (or the blood passing performance) after the blood absorption. Therefore, heretofore, the enhancement of the absorption performance under the conditions of high absorption amount has been limited.

Specifically, heretofore, it has been impossible to improve both the centrifugal retentive capacity with respect to blood and the blood permeation rate (or the blood passing performance) after absorption and swelling with blood. Even if the centrifugal retentive capacity with respect to blood was 30 g or higher, the blood permeation rate after absorption and swelling with blood could not heretofore been kept at 50 ml/minute or higher, and the blood passing performance after absorption of blood was thus insufficient. Accordingly, the reabsorption rate could not be kept high, and leakage occurred before the polymer reabsorbed blood.

In the present invention, as the absorbent member 2, the absorbent member having both a high centrifugal retentive capacity with respect to blood and a high blood permeation rate after absorption of blood is used. Therefore, the absorbent member 2 employed in the present invention has the effects of undergoing little leakage even under the conditions of high absorption amounts, which effects could not be obtained in the past.

As illustrated in FIG. 8, the absorbent member 2 comprises the permeable absorbent paper 2c, which is located at the outermost part, the absorbent polymer 2b, and the diffusing absorbent paper 2d, which is located more inward than the permeable absorbent paper 2c and includes and covers the absorbent polymer 2b.

Insofar as the absorbent member 2 has both the aforesaid high centrifugal retentive capacity with respect to blood and the aforesaid high blood permeation rate after absorption of blood, no limitation is imposed on the configuration of the absorbent member 2. However, in order to more reliably achieve such physical properties, the absorbent member 2 should preferably be provided with the absorbent polymer 2b. The absorbent polymer 2b should preferably have a centrifugal retentive capacity with respect to pseudo-blood, which is measured after equilibrium absorption swelling with the pseudo-blood, of 20 g/g or more. Also, the absorbent polymer 2b has a permeation rate with respect to pseudo-blood of 1 ml/minute or more. The permeation rate is measured by introducing 0.05 g of the absorbent polymer 2b into a cylinder having a cross-sectional area of 0.785 cm$^2$ (inner diameter: 10 mm), allowing the absorbent polymer 2b to swell with pseudo-blood, and thereafter causing the pseudo-blood to permeate through the absorbent polymer 2b.

If the centrifugal retentive capacity of the absorbent polymer 2b with respect to pseudo-blood is lower than 20 g/g, a high capacity for absorbing and retaining a fluid cannot be obtained. Also, if the permeation rate of the absorbent polymer 2b with respect to pseudo-blood is lower than 1.0 ml/minute, the body fluid passing performance of the absorbent polymer 2b after absorbing the liquid will become bad, and the high absorbency of the absorbent polymer 2b cannot be utilized efficiently.

Insofar as the aforesaid requirements for the physical properties are satisfied, no limitation is imposed on the composition of and the producing process for the absorbent polymer 2b. However, the absorbent polymer 2b should preferably be constituted of crosslinked polyacrylates having a high molecular weight, which can absorb and retain a large amount of liquid by means of the ionic osmotic pressure such that the absorbed fluid may not leak out even under pressurized conditions. In particular, the absorbent polymer 2b should preferably have the absorption functions such that the polymer can quickly absorb the body fluid from a sheet provided with fine spaces, such that the surface of the polymer can be kept in a dry state after the polymer has absorbed the body fluid and have been swollen, and such that the polymer may not obstruct the transfer of a body fluid which is excreted later.

Also, as described above with respect to the first embodiment, if the absorbent polymer has a uniform crosslinked structure, the absorbing functions described above cannot easily be obtained. Therefore, the absorbent polymer should preferably be provided with a crosslinking density gradient.

In order to impart a crosslinking density gradient to the absorbent polymer, one of various processes described above with respect to the first embodiment may be employed.

Figure 9:
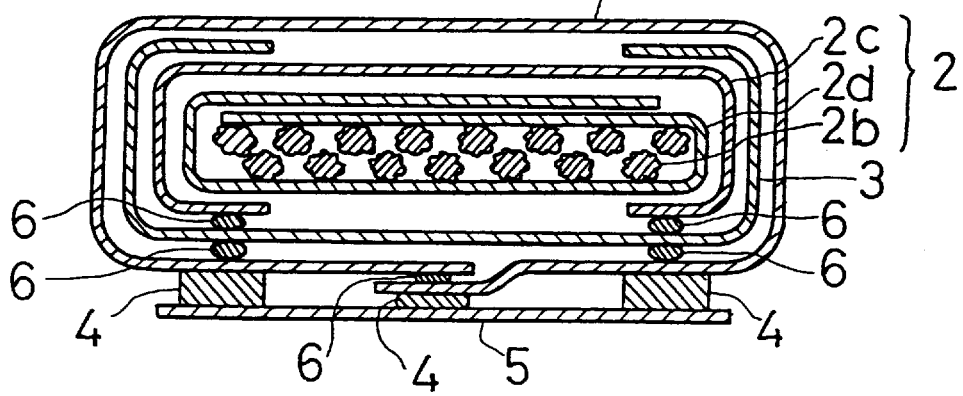
FIG. 9 is a sectional view showing a modification of the sanitary napkin shown in FIG. 8.

As described above with respect to the first embodiment, the particles of the absorbent polymer should preferably have an aspherical shape, and the degree of shape irregularity P of the particles of the absorbent polymer should preferably be 1.2 or more. Therefore, the sanitary napkin as the sixth embodiment of the absorbent article in accordance with the present invention should preferably be modified as shown in FIG. 9.

In cases where the particles of the absorbent polymer have an aspherical shape, the spaces among the particles can be prevented from decreasing due to rearrangement of the particles and close contact of the particles with one another when the absorbent polymer absorbs the body fluid and is thereby swollen. Also, if the degree of shape irregularity P of the particles of the absorbent polymer is lower than 1.2, the irregularity value of the unevenness of the surfaces of the particles of the absorbent polymer, which has been swollen, will become insufficient. As a result, the spaces cannot be kept among the particles of the absorbent polymer, which has been swollen, and the problems will occur in that the liquid passing performance between the particles becomes bad. Therefore, the degree of shape irregularity P of the particles of the absorbent polymer should preferably be 1.2 or more.

The amount of the absorbent polymer used should preferably fall within the range of 20 to 80% by weight, based on the total weight of the absorbent member, and should more preferably fall within the range of 30 to 60% by weight, based on the total weight of the absorbent member. Also, the absorbent polymer should be preferably spread at an amount of falling within the range of 100 to 500 g per 1 m$^2$, and more preferably falling within the range of 100 to 300 g per 1 m$^2$.

Specifically, the amount of the absorbent polymer used should preferably fall within the range of 1 to 5 g in an ordinary absorbent article, and should more preferably fall within the range of 1 to 3 g in an ordinary absorbent article.

If the amount of the absorbent polymer used per ordinary absorbent article is smaller than 1 g (or the weight proportion thereof is lower than 20% by weight, based on the total weight of the ordinary absorbent article), or if the absorbent polymer is spread at an amount of less than 100 g per 1 m$^2$ absorbent member, the capacity for immobilizing the body fluid under the conditions of large excretion amounts will become insufficient. Also, if the amount of the absorbent polymer used per ordinary absorbent article is larger than 5 g (or the weight proportion thereof is higher than 80% by weight, based on the total weight of the ordinary absorbent article), or if the absorbent polymer is spread at an amount of more than 500 g per 1 m$^2$ absorbent member, it will become difficult for the absorbent polymer to be perfectly secured in the absorbent member.

During the production of an absorbent member, particularly during the production of an absorbent member for absorbing a highly viscous body fluid such as blood, it is important to design the absorption spaces, in which the body fluid is to be temporarily stored in the absorbent member and which are constituted by paper, pulp fibers, or the like. Specifically, with an absorbent member, which mainly comprises a fluff pulp sheet constituted of ordinary softwood pulp, as in the conventional absorbent article, even if the absorbent polymer described above is used, the absorption rate becomes low and liquid leakage is caused to occur due to the twist and permanent set in fatigue, which occur with the pulp, before the absorbency function of the absorbent polymer works to the highest extent.

In particular, the absorbent member 2 should preferably contain bulky cellulose fibers and the absorbent polymer. In such cases, the absorbent member having a high absorbency can be obtained more reliably. The bulky cellulose fibers should preferably have the degree of fiber roughness of 0.3 mg/m or more (or a fiber cross-sectional area of 3.0×10$^{-6}$ cm$^2$ or more) and, at the same time, have the degree of fiber roundness of 0.5 or more. Alternatively, the bulky cellulose fibers should preferably have the degree of fiber roughness of 0.3 mg/m or more (or a fiber cross-sectional area of 5.0×10$^{-6}$ cm$^2$ or more), or have a three-dimensional fiber shape. The way how the degree of fiber roundness is measured, and the like, will be described later.

The three-dimensional fiber shape may be a torsion shape, a crimped shape, a bent shape, or the like.

The bulky cellulose fibers may be directly mixed with the absorbent polymer in order to constitute the absorbent member. Alternatively, an absorbent paper may be prepared with a wet type of paper preparing process from the bulky cellulose fibers and may then be used to constitute the absorbent member.

As the bulky cellulose fibers, the crosslinked cellulose fibers described above is preferably used which is obtainable from an intramolecular and/or intermolecular crosslinking of said cellulose fibers such that the bulky structure can be kept even in a set state, and which have an improved modulus of elasticity in the wet state.

As the cellulose fibers, it is possible to use any of natural cellulose fibers, such as wood pulp or cotton, and regenerated cellulose fibers, such as rayon and cupra, which satisfy the requirements described above. These kinds of cellulose fibers may be used alone or as a mixture of two or more of them. Among these kinds of cellulose fibers, it is advantageous to use the regenerated cellulose fibers, the fiber cross-sectional area and the fiber cross-sectional shape of which can be controlled freely, the mercerized pulp fibers, the fiber cross section of which has been swollen and enlarged, and the cellulose fibers, which are obtained by crosslinking these fibers.

As the crosslinking agents used in order to crosslink the cellulose fibers, the crosslinking agents described above with respect to the first embodiment can be employed.

As described above, the absorbent members 2 shown in FIGS. 8 and 9 are further provided with the permeable absorbent paper 2c, which has a high permeability and quickly absorbs and transmits blood to the side opposite to the side of the liquid permeable topsheet 1 in contact with the user's skin, i.e. to the outermost part of the absorbent member 2. The permeable absorbent paper 2c should preferably have the controlled spread characteristics (i.e., the controlled diffusing characteristics).

The permeable absorbent paper 2c, which is located at the outermost part of the absorbent member 2, should preferably contain 50 to 98 parts by weight of the aforesaid bulky cellulose fibers, and 2 to 30 parts by weight of the thermally fusible bonding fibers. Also, the permeable absorbent paper 2c should preferably have an absorption height after 1 minute absorption of physiological saline by Klemm's Method falling within the range of 20 to 80 mm, and an absorption height after 10 minutes absorption of physiological saline by Klemm's Method falling within the range of 30 to 100 mm. Further, the permeable absorbent paper 2c should preferably have a permeation time for 10 g of an 85% by weight aqueous glycerol solution of 50 seconds or less.

As the thermally fusible bonding fibers, the same thermally fusible bonding fibers as those described above with respect to the first embodiment may be used.

The proportion of the thermally fusible bonding fibers with respect to the total weight of the permeable absorbent paper 2c should preferably fall within the range of 2 to 30 parts by weight, and should more preferably fall within the range of 2 to 20 parts by weight. If the proportion of the thermally fusible bonding fibers with respect to the total weight of the permeable absorbent paper 2c is higher than 30 parts by weight, the permeability of the permeable absorbent paper 2c will often become low.

The absorbent member 2 is also provided with the diffusing absorbent paper 2d, which is located on the side more inward than the permeable absorbent paper 2c located at the outermost part of the absorbent member 2, and which includes and covers the absorbent polymer 2b. The diffusing absorbent paper 2d should preferably have a high diffusing capacity and a high permeability so that the body fluid having permeated through the absorbent paper 2c can be quickly diffused to the entire absorbent polymer 2b and can then be smoothly transferred to the polymer. Specifically, the diffusing absorbent paper 2d should preferably have the composition and the physical properties described below.

Specifically, the diffusing absorbent paper 2d should preferably comprises 20 to 80 parts by weight of the bulky cellulose fibers, 80 to 20 parts by weight of hydrophilic fine fibers, and 0 to 30 parts by weight of thermally fusible bonding fibers. Also, the diffusing absorbent paper 2d should preferably have an absorption height after 1 minute absorption of physiological saline by Klemm's Method of 50 mm or more, and an absorption height after 10 minutes absorption of physiological saline by Klemm's Method of 100 mm or more. Further, the diffusing absorbent paper 2d should preferably have a permeation time for 10 g of an 85% by weight aqueous glycerol solution of 100 seconds or less.

The bulky cellulose fibers contained in the diffusing absorbent paper 2d should preferably be the pulp fibers obtained by crosslinking the mercerized pulp fibers, which have the degree of fiber roughness of 0.3 mg/m or more (or a fiber cross-sectional area of $3.0 \times 10^{-6}$ cm$^2$ or more) and, at the same time, have the degree of fiber roundness of 0.5 or more.

As the hydrophilic fine fibers, the same hydrophilic fine fibers as those described above with respect to the first embodiment may be employed.

Figure 10:
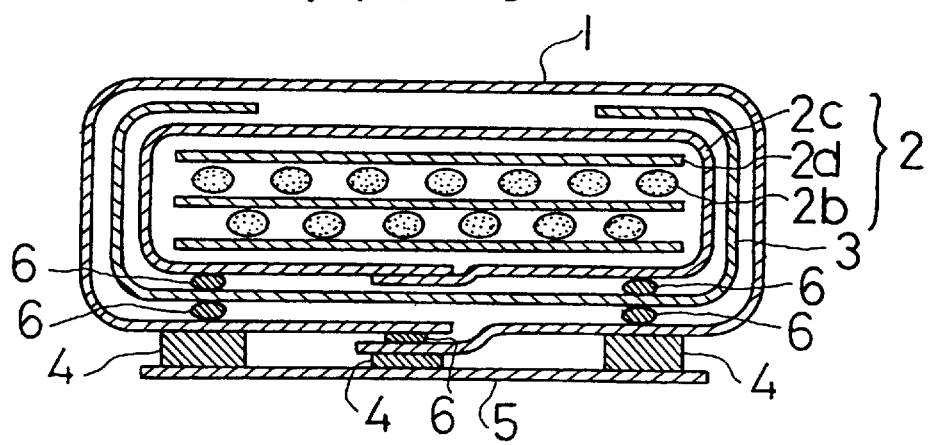
FIG. 10 is a sectional view showing a seventh embodiment of the absorbent article in accordance with the present invention, which is constituted as a sanitary napkin, the sectional view being taken along the transverse direction of the sanitary napkin.

A seventh embodiment of the absorbent article in accordance with the present invention, which is constituted as a sanitary napkin, will be described hereinbelow with reference to FIG. 10. The same features as those in the first embodiment described above will not be described in detail hereinbelow, and the explanation with respect to the aforesaid embodiment is also applied to the seventh embodiment. In FIG. 10, similar elements are numbered with the same reference numerals with respect to FIG. 1.

Figure 11:
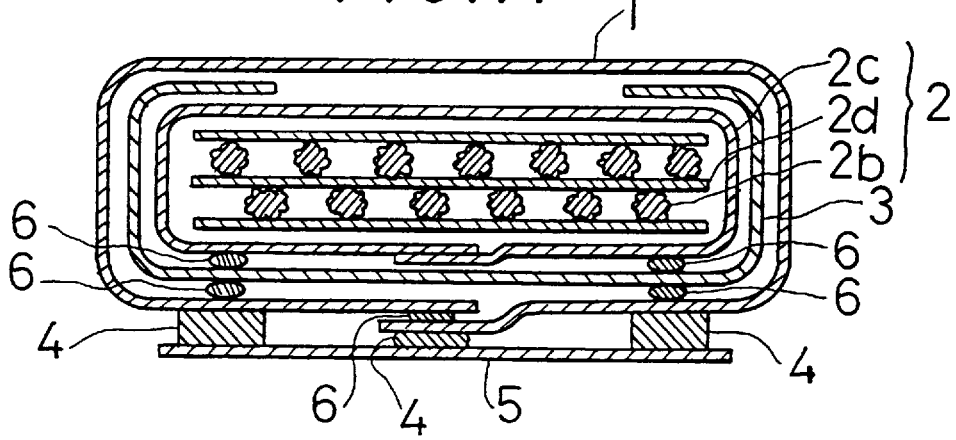
FIG. 11 is a sectional view showing a modification of the sanitary napkin shown in FIG. 10.

An absorbent member 2 shown in FIG. 10 comprises a plurality of (in this case, three) sheets of the diffusing absorbent paper 2d, which are overlaid one upon another, and the particles of the absorbent polymer 2b, which are spread between the sheets of the diffusing absorbent paper 2d. In this manner, the diffusing absorbent paper 2d and the absorbent polymer 2b are alternately overlaid one upon the other. The combination of the absorbent polymer 2b and the sheets of the diffusing absorbent paper 2d are included and covered with the permeable absorbent paper 2c. In this manner, the absorbent polymer 2b, the sheets of the diffusing absorbent paper 2d, and the permeable absorbent paper 2c are combined with one another into a unitary body. The particles of the absorbent polymer 2b should preferably have an irregular, aspherical shape as shown in FIG. 11.

Figure 12:
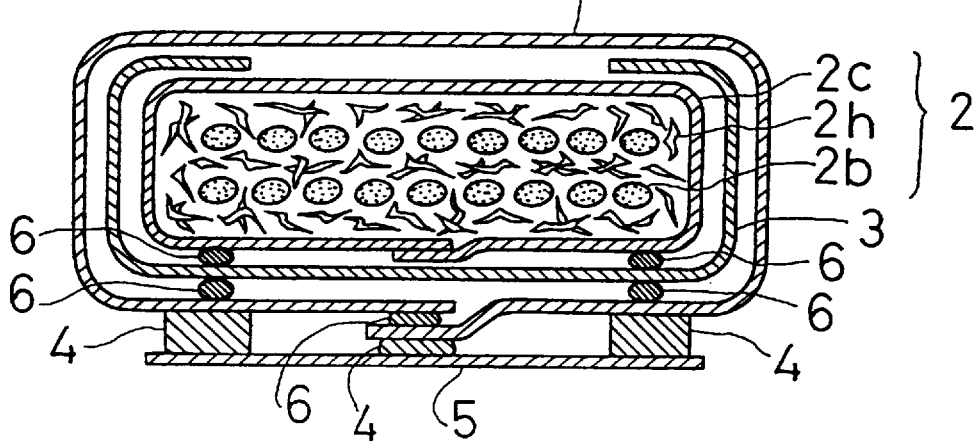
FIG. 12 is a sectional view showing an eighth embodiment of the absorbent article in accordance with the present invention, which is constituted as a sanitary napkin, the sectional view being taken along the transverse direction of the sanitary napkin.

An eighth embodiment of the absorbent article in accordance with the present invention, which is constituted as a sanitary napkin, will be described hereinbelow with reference to FIG. 12. The same features as those in the first embodiment described above will not be described in detail hereinbelow, and the explanation with respect to the aforesaid embodiment is also applied to the eighth embodiment. In FIG. 12, similar elements are numbered with the same reference numerals with respect to FIG. 1.

Figure 13:
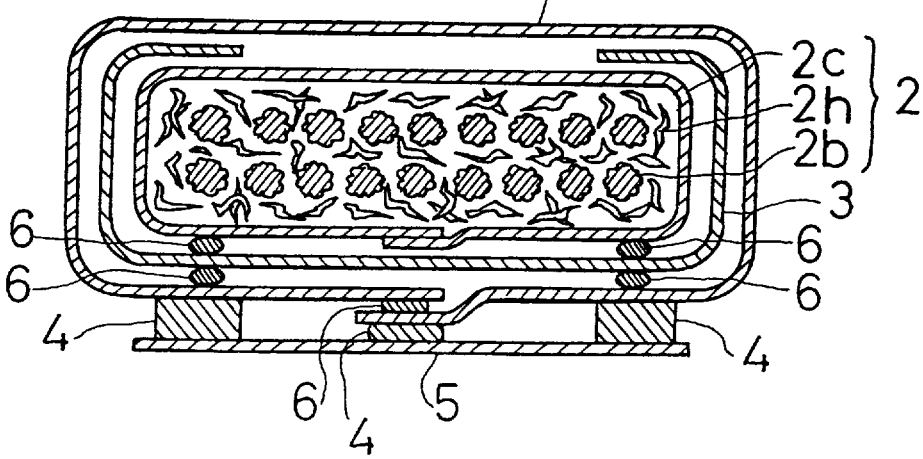
FIG. 13 is a sectional view showing a modification of the sanitary napkin shown in FIG. 12.

An absorbent member 2 shown in FIG. 12 comprises the absorbent polymer 2b and a fluff pulp 2h, which are mixed with each other. The fluff pulp 2h may be constituted of conventional softwood pulp. However, in order that the spaces among the polymer particles in a wet state can be kept stable, i.e. in order that the blood permeability may be kept good, the fluff pulp 2h should preferably be constituted of the pulp fibers obtained by crosslinking the bulky pulp fibers, particularly the mercerized pulp fibers, which have the degree of fiber roughness of 0.3 mg/m or more (or a fiber cross-sectional area of $3.0 \times 10^{-6}$ cm$^2$ or more) and, at the same time, have the degree of fiber roundness of 0.5 or more. The mercerized pulp fibers, which have thus been crosslinked, have an improved modulus of elasticity in the wet state. Also, the particles of the absorbent polymer 2b should preferably have an irregular, aspherical shape as shown in FIG. 13.

As described above, the absorbent article in accordance with the present invention restricts reflow of the liquid from the absorbent member to the surface and liquid leakage even when it is put on and used for a long period of time or even when it is used under the conditions of violent motion, and which has a high absorbency and a high comfortableness. Thus the absorbent article in accordance with the present invention is advantageous over the conventional absorbent article.

Specifically, the fibers constituting the absorbent member do not undergo the twist and permanent set in fatigue even when they absorb the body fluid, and the absorbent member can thus exhibit a high reabsorption rate. Also, the absorbent polymer exhibits its absorption performance to the highest possible extent without suffering from an absorption obstruction. Therefore, even under the conditions of long-time use and large amounts of excretion, most of the excreted body fluid can be immobilized by the polymer, and the absorbent article exhibits little reflow of the body fluid from the absorbent member to the surface of the absorbent article and little leakage.

More specifically, the absorbent article in accordance with the present invention is provided with the absorbent member comprising the crosslinked cellulose fibers, which do not undergo the twist and permanent set in fatigue even when absorbing the body fluid and which exhibit little swelling in a wet state, and the absorbent polymer, which has both the high body liquid retentive capacity and the high permeation rate. Therefore, even when the body fluid is excreted repeatedly, the absorption spaces of the crosslinked cellulose fibers for temporarily storing the body fluid are not lost and are kept stable, and the reabsorption rate can thereby be kept high. Also, the absorbent polymer for holding the body fluid does not undergo the gel blocking phenomenon and can smoothly transfer the body fluid to the other part of the absorbent polymer. A large amount of the body fluid can thus be reliably immobilized by the polymer, and little leakage from the absorbent article occurs even under the conditions of large amounts of excretion. Such features could not be obtained with the conventional absorbent article.

In cases where the absorbent member is constituted by combining the specific absorbent polymer, which has a high absorbency and a high permeability, and the absorbent paper comprising the crosslinked cellulose fibers, particularly the composite absorbent paper, which has both the permeability and the diffusing properties, the effects described above can be enhanced even further, and it becomes possible to obtain the absorbent article, which has a high absorbency and a very simple configuration, and which is markedly thinner than the conventional absorbent article.

The topsheet, which is employed in the absorbent article in accordance with the present invention, will be described hereinbelow.

The liquid permeable topsheet of the absorbent article in accordance with the present invention comprises at least a liquid permeable sheet, which comprises a layer in contact with the user's skin and a layer not in contact with the user's skin, the layers being overlaid and combined with each other into a unitary body. The layer in contact with the user's skin comprises a porous film of a thermoplastic resin or a nonwoven fabric of synthetic fibers. The layer not in contact with the user's skin comprises an absorbent sheet, which at least comprises bulky cellulose fibers having a high absorbency and a high liquid permeability. Therefore, under every use condition, when the excreted body fluid is absorbed by the porous film or the nonwoven fabric, which is located on the front surface side, the absorbent sheet of the layer not in contact with the user's skin can quickly absorb the body fluid and can smoothly transmit it to the absorbent member.

Therefore, under every use condition, the absorbent article in accordance with the present invention exhibits little flow and little retention of the body fluid on the topsheet and can smoothly guide the body fluid to the absorbent member. Therefore, the absorbent article in accordance with the present invention has a high absorption performance and exhibits little stickiness to the body.

A ninth embodiment of the absorbent article in accordance with the present invention, which is constituted as a sanitary napkin, will be described hereinbelow with reference to FIG. 14. A sanitary napkin 101 shown in FIG. 14 comprises a liquid permeable topsheet 102, a liquid retentive absorbent member 103, and liquid impermeable back sheet 104. The topsheet 102 comprises at least a liquid permeable sheet, which comprises a first layer 102a in contact with the user's skin and a second layer 102b not in contact with the user's skin. The layers 102a and 102b have different compositions and are overlaid and combined with each other into a unitary body. The layer 102a in contact with the user's skin comprises a porous film of a thermoplastic resin or a nonwoven fabric of synthetic fibers. The layer 102b not in contact with the user's skin comprises an absorbent sheet, which at least comprises bulky cellulose fibers. In the sanitary napkin 101 shown in FIG. 14, the aforesaid permeable absorbent paper, the aforesaid diffusing absorbent paper, and the aforesaid composite absorbent paper may be applied appropriately.

Specifically, the sanitary napkin 101 is formed in a substantially longitudinally elongated shape. The topsheet 102 directly covers the front surface side and the side surfaces of the absorbent member 103. Also, on the side not in contact with the user's skin, the topsheet 102 and the absorbent member 103 are secured to each other by fixing members 105. Further, the topsheet 102 and the back sheet 104 are secured to each other by fixing members 105. Furthermore, the surface of the back sheet 104 not in contact with the user's skin is provided with slipping-off preventing members 106 for securing the sanitary napkin 101 to shorts during the use of the sanitary napkin 101. The slipping-off preventing members 106 are protected by a release paper 107.

The absorbent member 103 comprises fluff pulp 103a, a absorbent polymer 103b, and a wet-process absorbent paper 103c. As the materials for the fluff pulp 103a, the absorbent polymer 103b, the wet-process absorbent paper 103c, the back sheet 104, the fixing members 105, the slipping-off preventing members 106, and the release paper 107, any of known materials, which have heretofore been employed for absorbent articles, may be used.

Figure 14:
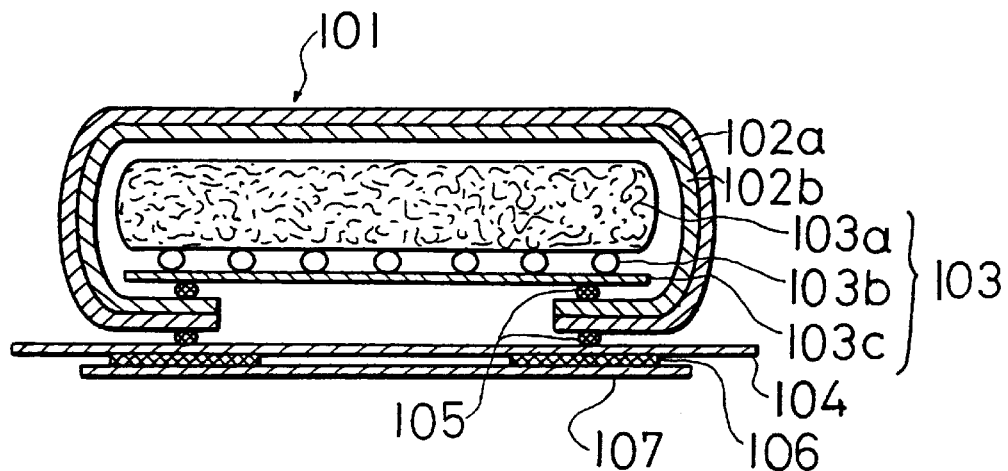
FIG. 14 is a sectional view showing a ninth embodiment of the absorbent article in accordance with the present invention, which is constituted as a sanitary napkin, the sectional view being taken along the transverse direction of the sanitary napkin.
Figure 15:
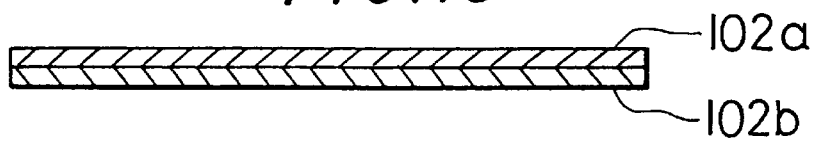
FIG. 15 is an enlarged view showing a topsheet, which is employed in the embodiment of FIG. 14.

As illustrated in FIGS. 14 and 15, in the sanitary napkin 101, the topsheet 102 comprises the liquid permeable sheet, which comprises the layer 102a in contact with the user's skin and the layer 102b not in contact with the user's skin. The layers 102a and 102b are overlaid and combined with each other into a unitary body.

The layer 102a in contact with the user's skin comprises a porous film of a thermoplastic resin or a nonwoven fabric of synthetic fibers.

As the porous film of a thermoplastic resin, it is possible to use film type of porous films or porous nets, which are conventionally used for topsheets of absorbent articles. For example, it is possible to use porous films obtainable by perforating the films of a thermoplastic resin, such as polyethylene or polypropylene.

As the nonwoven fabric of synthetic fibers, it is possible to use wet-process or dry-process nonwoven fabrics, which are conventionally used for the topsheets of absorbent articles. For example, it is possible to use wet-process fabrics or dry-process nonwoven fabrics of synthetic fibers, such as polyethylene fibers, polypropylene fibers, polyester fibers, polyethylene-polypropylene composite fibers, polyethylene-polyester composite fibers, and polyvinyl alcohol fibers; and regenerated fibers, such as rayon fibers.

The layer 102b not in contact with the user's skin comprises an absorbent sheet, which at least comprises bulky cellulose fibers.

It is important that the absorbent sheet has a high absorbency and a high permeability. In order for such an absorbent sheet to be obtained, it is important to blend the cellulose fibers, which has a high hydrophilicity and a bulky structure, in the absorbent sheet. It is also important to overlay the absorbent sheet and the layer 102a in contact with the user's skin one upon the other and to combine them into a unitary body.

The bulky cellulose fibers contained in the absorbent sheet have a high bulkiness, a high absorbency, and a high permeability. The bulky cellulose fibers are free of the problems in that strong tightening force acts due to hydrogen bonding between the fibers and the distance between the fibers becomes very short during the dehydrating and drying steps in the conventional wet process for sheet making from pulp. Specifically, during the wet type of sheet making process for the layer not in contact with the user's skin, the tightening force acting between the cellulose fibers is controlled, and the bulky absorption spaces are formed. Also, the two incompatible requirements, i.e. the high liquid absorbency and the high liquid permeability, are satisfied. In this manner, the fiber space structure in the entire absorbent sheet is designed and idealized.

By way of example, as the bulky cellulose fibers, the cellulose fibers described under (1) and (2) below may be mentioned.

(1) Cellulose fibers having a three-dimensional structure, such as a torsion structure, a crimped structure, or a bent and/or branched structure.

The term "torsion structure" as used herein means the structure, in which the fiber is twisted with respect to the longitudinal direction of the fiber. The number of twists should preferably be 2.0/mm or more. The term "crimped structure" as used herein means the structure, in which the fiber is spirally crimped with respect to the longitudinal direction of the fiber. Also, the term "bent structure" as used herein means the structure, in which the fiber is bent along the longitudinal direction of the fiber. Further, the term "branched structure" as used herein means the structure, in which the fiber is branched. (2) Cellulose fibers having a thick fiber cross section, which should preferably have a degree of fiber roughness falling within the range of 0.3 to 2 mg/m, and should more preferably have a degree of fiber roughness falling within the range of 0.33 to 1 mg/m.

If the degree of fiber roughness of the cellulose fibers is lower than 0.3 mg/m, the cellulose fibers will be excessively thin and flexible, and therefore cannot exhibit the bulkiness. Also, an absorbent sheet comprising such cellulose fibers has an insufficient permeability. Further, even if the crosslinking described below is carried out on such fibers, sufficient crosslinking effects cannot be obtained. If the degree of fiber roughness of the cellulose fibers is higher than 2 mg/m, the cellulose fibers will be excessively rigid, or the structure between the fibers will be disturbed markedly during the preparation of the absorbent sheet. Therefore, the capacity for absorbing the body fluid from the surface layer will become insufficient. Accordingly, the cellulose fibers should preferably have a degree of fiber roughness falling within the aforesaid range.

Specifically, in order that an absorbent sheet having a high absorbency and a high liquid permeability may be obtained, it is essential for the bulky cellulose fibers used in the ninth embodiment of FIG. 14 to have a three-dimensional shape with respect to the longitudinal direction of the fiber as in (1) above or to have a thick fiber cross section.

The material for the bulky cellulose fibers described above may be selected from any materials, which satisfy the requirements described in (1) or (2) above. Specifically, the bulky cellulose fibers may be constituted of natural cellulose fibers, such as pulp or cotton; or regenerated cellulose fibers, such as rayon or cupra. These fibers may be used alone or as a mixture of two or more of them.

Among these kinds of cellulose fibers, it is advantageous to use the regenerated cellulose fibers, the fiber cross-sectional area and the fiber cross-sectional shape of which can be controlled freely, the mercerized pulp fibers, the fiber cross section of which has been swollen and enlarged, and the crosslinked pulp fibers having a bulky structure. It is particularly advantageous to use the crosslinked pulp fibers, which exhibit the markedly bulky structure and are available at a low cost.

In cases where the regenerated cellulose fibers, such as rayon or cupra, are used as the cellulose fibers described in (2) above, the degree of fiber roughness should preferably be adjusted at a value falling within the range of 0.3 to 2 mg/m by the adjustment of the spinning nozzle diameter, the spinning rate, and the orienting rate.

In cases where the regenerated cellulose fibers are used, because they have uniform thickness in the longitudinal direction of the fibers, the degree of fiber roughness may be calculated from the value of denier.

As for the fibers, such as natural pulp fibers, which have nonuniform thickness in the longitudinal direction of the fibers, the degree of fiber roughness should preferably be measured with a fiber roughness meter, and the fibers having the degree of fiber roughness falling within the aforesaid range should preferably be used.

As for the cellulose fibers described in (1) and (2) above, particularly as for the cellulose fibers described in (2) above, the resistance to transfer of the body fluid to the absorbent member becomes lower as the cross-sectional shape of the cellulose fiber is closer to the true circle. Therefore, the cross-sectional shape of the cellulose fibers should preferably be adjusted. Specifically, the degree of fiber roundness of the cellulose fibers should preferably be 0.5 or more.

As the bulky cellulose fibers, it is also possible to use the cellulose fibers, which have been obtained by crosslinking the pulp fibers having a degree of fiber roughness of 0.3 mg/m or more.

Most of the conventional wood pulp fibers have a degree of fiber roughness of lower than 0.3 mg/m. Even if an absorbent sheet is made from such pulp fibers, an absorbent sheet having sufficient permeability cannot be obtained. Also, even if such pulp fibers are crosslinked, sufficient effects of the crosslinking cannot be obtained. However, the study carried out by the inventors revealed that the effects described above can be enhanced even further by carrying out the crosslinking of pulp fibers, which have a degree of fiber roughness of 0.3 mg/m or more, with a crosslinking agent.

Examples of the pulp fibers having a degree of fiber roughness of 0.3 mg/m or more include kraft pulp NBKP available under the trade name "ALBACEL" (supplied by Federal Paper Board Co.), and under the trade name "INDORAYON" (supplied by PT Inti Indorayon Utama).

The wood pulp fibers, such as the ordinarily used hardwood pulp and softwood pulp fibers, have a flat cross-sectional shape due to delignification and a degree of fiber roundness of lower than 0.5. In order for the wood pulp fibers to have the degree of fiber roundness of 0.5 or more, for example, the wood pulp fibers may be subjected to mercerization, and the cross section of the wood pulp fibers may thereby be swollen.

By way of example, the mercerized pulp fibers can be obtained by mercerizing the pulp fibers, which have a degree of fiber roughness of 0.3 mg/m or more, thereby enhancing the degree of fiber roundness of the pulp fibers, and thereafter crosslinking the mercerized pulp fibers with a crosslinking agent. Alternatively, the fibers obtained by crosslinking the commercially available mercerized pulp fibers with a crosslinking agent may be used.

Examples of the commercially available mercerized pulp fibers include the trade name "FILTRANIER" (supplied by ITT Rayonier Inc.) and the trade name "POROSANIER" (supplied by ITT Rayonier Inc.).

The degree of fiber roughness and the degree of fiber roundness can be measured with the methods described above.

As the cellulose fibers described in (1) and (2) above, the crosslinked cellulose fibers should preferably be used, which is obtainable from an intramolecular and/or intermolecular crosslinking of said cellulose fibers such that the bulky structure can be kept even in a wet state, and which have an improved modulus of elasticity in the wet state.

As the crosslinking agent, the same crosslinking agents as those described above may be used. In particular, polycarboxylic acids, polyglycidyl ethers, and the like, which do not generate formalin harmful to the human body during the crosslinking reaction, are preferable. The crosslinked pulp fibers having been obtained with such a crosslinking agent can be used preferably as the bulky cellulose fibers.

As in the cases described above, the amount of the crosslinking agent used should preferably fall within the range of 0.2 to 20 parts by weight per 100 parts by weight of the cellulose fibers to be crosslinked.

The absorbent sheet can be made easily with an ordinary absorbent sheet preparing process and by using the bulky cellulose fibers described above.

It is important for the absorbent sheet described above to have a high absorbency and a high permeability. Specifically, the absorbent sheet should preferably have an absorption height after 1 minute absorption of physiological saline by Klemm's Method falling within the range of 30 to 70 mm, and should more preferably have an absorption height after 1 minute absorption of physiological saline by Klemm's Method falling within the range of 30 to 60 mm. Also, the absorbent sheet should preferably have an absorption height after 10 minutes absorption of physiological saline by Klemm's Method falling within the range of 40 to 120 mm, and should more preferably have an absorption height after 10 minutes absorption of physiological saline by Klemm's Method of 50 to 100 mm.

If the absorption height by Klemm's Method after 1 minute with respect to physiological saline is lower than 30 mm, or if the absorption height by Klemm's Method after 10 minutes with respect to physiological saline is lower than 40 mm, the capacity for absorbing the body fluid from the surface side will become insufficient, and retention of the body fluid on the surface will increase. If the absorption height by Klemm's Method after 1 minute with respect to physiological saline is higher than 70 mm, or if the absorption height by Klemm's Method after 10 minutes with respect to physiological saline is higher than 120 mm, the body fluid diffusing capacity will become excessively high, the body fluid will be excessively spread in the topsheet, and leakage will occur. Therefore, these absorption heights by Klemm's Method should preferably fall within the aforesaid ranges.

Also, the absorbent sheet described above should preferably have a permeation time for 10 g of an 85% by weight aqueous glycerol solution of 50 seconds or less, and should more preferably have a permeation time for 10 g of an 85% by weight aqueous glycerol solution falling within the range of 5 to 40 seconds.

If the permeation time of the absorbent sheet for 10 g of an 85% by weight aqueous glycerol solution is longer than 50 seconds, the liquid permeability will become bad, the absorption rate will become low, and the characteristics with respect to the retention of the body fluid on the surface will become bad. Therefore, the permeation time of the absorbent sheet should preferably fall within the aforesaid range.

Examples of the preferable absorbent: sheet having a high absorbency and a high liquid permeability include a wet-process absorbent paper, which comprises 50 to 98 parts by weight, preferably 70 to 98 parts by weight, of the bulky cellulose fibers described above and 2 to 30 parts by weight, preferably 2 to 20 parts by weight, of thermally fusible bonding fibers, and has a basis weight of 20 to 60 g/m$^2$.

As the methods for mixing and paper preparation, any of known methods may be used.

In the absorbent paper, if the proportion of the bulky cellulose fibers is lower than 50 parts by weight, the permeation rate of the obtained absorbent paper will become insufficient. If the proportion of the bulky cellulose fibers in the absorbent paper is larger than 98 parts by weight, it will become difficult to form a sheet of the absorbent paper. Therefore, the proportion of the bulky cellulose fibers in the absorbent paper should preferably fall within the aforesaid range. Also, in the absorbent paper, if the proportion of the thermally fusible bonding fibers is lower than 2 parts by weight, the strength of the absorbent paper will become insufficient, and it will become difficult to form a sheet of the absorbent paper. If the proportion of the thermally fusible bonding fibers in the absorbent paper is larger than 30 parts by weight, the permeability of the absorbent paper will often become low. Therefore, the proportion of the thermally fusible bonding fibers in the absorbent paper should preferably fall within the aforesaid range.

As the thermally fusible bonding fibers, the same thermally fusible bonding fibers as those described above can be used.

The absorbent sheet described above may also contain constituents other than the bulky cellulose fibers and the thermally fusible bonding fibers. Examples of the other constituents include other pulp, such as softwood pulp, hardwood pulp, and straw pulp; and tenacity assisting agents, such as dialdehyde starch and sponge.

In order to overlay the layer, which is located in contact with the user's skin, and the layer, which is located on the side not in contact with the user's skin, one upon the other and to combine them with each other into a unitary body, any of methods for combining the porous film or the nonwoven fabric and the absorbent sheet with each other into a unitary body may be used. For example, such that the requirements of the present invention may be satisfied, one of the methods described below may be used.

(1) A method, wherein the porous film or the nonwoven fabric and the absorbent sheet are passed between a pair of embossing rolls and thereby combined with each other into a unitary body.

(2) A method, wherein the porous film or the nonwoven fabric and the absorbent sheet are combined together into a unitary body by using an adhesive agent or a pressure sensitive adhesive, typically a hot melt, or the like.

(3) A method, wherein the porous film or the nonwoven fabric and the absorbent sheet are subjected together to a sheet making operation for obtaining combined sheets during the step for making the absorbent sheet.

(4) A method, wherein a wet type of multi-layer paper preparing process is used, a first paper (nonwoven fabric) constituted of synthetic fibers is prepared, a second paper (absorbent sheet) constituted of the bulky cellulose fibers described above is prepared in the second paper preparing process, and thereafter the first paper and the second paper are subjected together to a paper preparing operation for obtaining a combined paper.

The methods (1), (2), (3), and (4) may be used alone or may be used in combination. For example, the methods (1) and (3) may be combined such that the combined sheet may be obtained with the wet process and may thereafter be subjected to a heat embossing operation.

As the method for superposing the two layers one upon the other and combining them with each other into a unitary body, a method should preferably be used, wherein the porous film or the nonwoven fabric and the absorbent sheet are together subjected to a sheet making operation for obtaining combined sheets, and the combined sheets are thereafter molten with heat in a heat embossing operation, or the like, during a drying step and thereby combined into a unitary body. Alternatively, a method should preferably be used, wherein a nonwoven fabric of synthetic fibers, which constitutes the layer in contact with the user's skin, is prepared as a first paper in a multi-layer paper preparing process, an absorbent sheet comprising the bulky cellulose fibers is then prepared as a second paper, and thereafter the first paper and the second paper are overlaid and combined with each other into a unitary body. With such methods, the bulky cellulose fibers contained in the absorbent sheet, which constitutes the layer not in contact with the user's skin, interlock more tightly with the layer in contact with the user's skin. Therefore, the topsheet thus obtained can more smoothly guide the body fluid to the absorbent member.

A tenth embodiment of the absorbent article in accordance with the present invention, which is constituted as a sanitary napkin, will be described hereinbelow with reference to FIGS. 16 and 17. The explanation with respect to the ninth embodiment described above with reference to FIGS. 14 and 15 is also applied to the tenth embodiment. In the tenth embodiment shown in FIGS. 16 and 17, the aforesaid permeable absorbent paper, the aforesaid diffusing absorbent paper, and the aforesaid composite absorbent paper may be applied appropriately.

Figure 16:
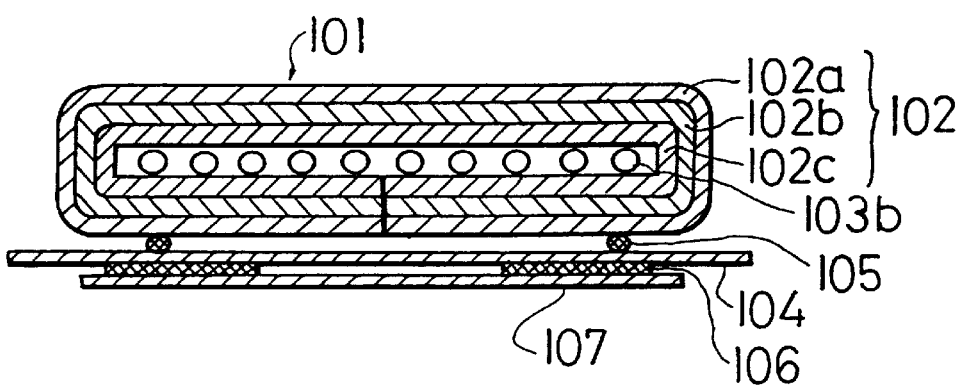
FIG. 16 is a sectional view showing a tenth embodiment of the absorbent article in accordance with the present invention, which is constituted as a sanitary napkin, the sectional view being taken along the transverse direction of the sanitary napkin.
Figure 17:
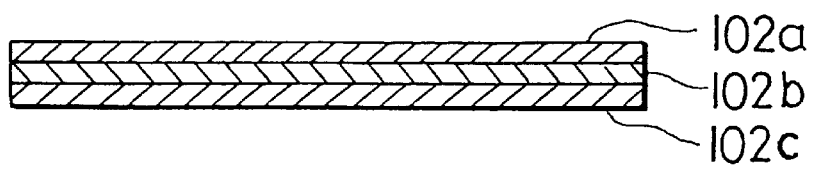
FIG. 17 is an enlarged view showing a topsheet, which is employed in the embodiment of FIG. 16.

A sanitary napkin 101 shown in FIG. 16 is provided with a topsheet 102. As illustrated in FIG. 17, the topsheet 102 comprises a liquid permeable sheet, which comprises a layer 102*a* in contact with the user's skin, a layer 102*b* not in contact with the user's skin, and a permeable absorbent paper 102*c*, which is a third layer overlaid on the layer 102*b* not in contact with the user's skin. (The permeable absorbent paper 102*c* is located on the side not in contact with the user's skin.) The layers 102*a*, 102*b*, and 102*c* are overlaid and combined with one another into a unitary body. The topsheet 102 completely covers the absorbent polymer 103*b* which serves as the absorbent member.

Specifically, in the sanitary napkin 101 shown in FIG. 16, the topsheet and the absorbent member are formed into a unitary body by the liquid permeable sheet and the absorbent polymer.

As illustrated in FIG. 16, as the absorbent article in accordance with the present invention, the topsheet should particularly preferably be constituted of the liquid permeable sheet, which comprises the aforesaid three layers overlaid and combined with one another into a unitary body. The topsheet and the absorbent member should most preferably be formed by combining the single liquid permeable sheet and the plurality of particles of the absorbent polymer with each other.

Specifically, by employing the configuration shown in FIG. 16, the topsheet and the absorbent polymer can be completely combined into a unitary body. Under every use condition, blood is not left on the surface and can be smoothly guided to the absorbent polymer and immobilized thereby. Also, the absorbent article having a simple configuration, a very thin thickness and a high absorbency can thus be obtained.

The permeable absorbent paper used as the third layer in the sanitary napkin 101 shown in FIG. 16 prevents the absorbent polymer from falling through the liquid permeable sheet. Specifically, the permeable absorbent paper at least comprises hydrophilic fine fibers such that the distance between the fibers in the liquid permeable sheet may be short and such that the absorbent polymer can be prevented from falling through the liquid permeable sheet.

More specifically, as the permeable absorbent paper, an absorbent paper is suitable, which should preferably contain 40 to 100 parts by weight of hydrophilic fine fibers and should more preferably contain 50 to 80 parts by weight of hydrophilic fine fibers, and which should preferably contain 60 to 0 parts by weight of bulky cellulose fibers and should more preferably contain 50 to 20 parts by weight of bulky cellulose fibers, and which should preferably have a basis weight falling within the range of 10 to 50 g/m$^2$, should more preferably have a basis weight falling within the range of 10 to 30 g/m$^2$.

The amount of the bulky cellulose fibers blended may be restricted such that the substantial space amount in the permeable absorbent paper can be kept large, and such that the transfer of blood to the polymer may not be obstructed due to closeness of the hydrophilic fine fibers.

Also, if the proportion of the bulky cellulose fibers in the permeable absorbent paper is larger than 60 parts by weight, the distance between the fibers will become excessively long, and polymer leakage will occur. Therefore, the proportion of the bulky cellulose fibers in the permeable absorbent paper should preferably fall within the aforesaid range.

Examples of the hydrophilic fine fibers suitable for use in the permeable absorbent paper include the fibers, which have hydrophilic fiber surfaces and have a larger surface area, preferably the hydrophilic fibers, which have a degree of fiber roughness of less than 0.2 mg/m and a degree of fiber roundness less than 0.5, or the hydrophilic fibers, which have a fiber surface area of 1.0 m$^2$/g or more. Specifically, as the hydrophilic fine fibers, any of fibers having the physical properties described above can be used. Examples of the hydrophilic fine fibers include cellulose fibers, such as pulp fibers, cotton fibers, and rayon fibers; and hydrophilic synthetic fibers, such as acrylonitrile fibers, and polyvinyl alcohol fibers. The above-enumerated hydrophilic fine fibers may be used alone or as a mixture of two ore more of them.

Among these fibers, the pulp fibers are advantageous in that they are available at a low cost, and in that the fiber surface area can be controlled by the control of beating conditions. Examples of such pulp fibers include kraft pulp NBKP (e.g., trade name "SKEENA PRIME" supplied by Skeena Cellulose Co.), which has been finely beaten, LBKP (trade name "PRIME ALBERT ASPEN HARDWOOD" supplied by Weyerhauser Paper), and straw pulp fibers.

In the embodiment of FIG. 16, as the absorbent polymer, any of known absorbent polymer can be used. The amount of the absorbent polymer blended, expressed in terms of the amount of the absorbent polymer spread per 1 m$^2$, should preferably fall within the range of 20 to 500 g, and should more preferably fall within the range of 30 to 300 g. It is also possible to use the crosslinked absorbent polymer.

In the embodiments described above, the absorbent article in accordance with the present invention is constituted as the sanitary napkin. However, the absorbent article in accordance with the present invention is not limited to the sanitary napkin and is also applicable to, for example, disposable diapers, pads for incontinent people, breast milk sheets, and the like.

As described above, the absorbent article in accordance with the present invention exhibits no separation of the topsheet and the absorbent sheet from each other, little retention of liquid on the surface, and a high liquid absorbency, and little stickiness to the body.

Specifically, in the absorbent article in accordance with the present invention, the liquid permeable sheet is used as the liquid permeable topsheet. The liquid permeable sheet comprises the layer in contact with the user's skin and the layer on the side not in contact with the user's skin, which layers are overlaid and combined with each other into a unitary body. The layer in contact with the user's skin comprises the porous film or the nonwoven fabric. The layer not in contact with the user's skin comprises the absorbent sheet, which comprises bulky cellulose fibers having a high absorbency and a high liquid permeability. Therefore, when the excreted body fluid permeates through the layer in contact with the user's skin, the layer not in contact with the user's skin quickly absorbs the body fluid and smoothly transfer the body fluid to the absorbent member.

Accordingly, with the absorbent article in accordance with the present invention, under every use condition, the body fluid can be smoothly guided to the absorbent member without flowing or remaining on the topsheet. As a result, the absorbent article in accordance with the present invention can has a high absorbing capacity, can provide a dry feeling, and is free of leakage.

Also, with the absorbent article in accordance with the present invention, wherein the topsheet and the absorbent member are constituted of the threelayer liquid permeable sheet, which comprises the layer in contact with the user's skin, the layer not in contact with the user's skin, and the permeable absorbent paper having a high absorbency, the three layers being overlaid and combined with one another into a unitary body, and the absorbent polymer, the topsheet and the absorbent polymer can be completely combined into a unitary body. Therefore, under every use condition, blood does not remain on the surface of the topsheet and can be smoothly immobilized by the absorbent polymer. Thus the absorbent article in accordance with the present invention has a simple configuration and exhibits little liquid leakage.

The invention will be understood more readily with reference to the following examples; however these examples are intended to illustrate the invention and are not to be construed to limit the scope of the invention.

In the descriptions below, "%" represents "% by weight" unless otherwise specified.

First, the absorbent polymer, cellulose fibers, and absorbent paper used in the examples and the comparative examples were prepared in the manner described below, and their functions were measured.

EXAMPLE 1

Preparation of Absorbent Polymer

Into a 500-ml four-necked round flask equipped with a stirrer, a reflux condenser, a dropping funnel, and a nitrogen gas feed pipe, 230 ml of cyclohexane and 1.4 g of sorbitan monostearate (supplied under the trade name "Rheodol SPS-12" by Kao Corp.) were introduced. The resulting mixture was stirred to obtain a homogeneous solution.

Also, in an Erlenmeyer flask, 30 g of an acrylic acid monomer was neutralized with an aqueous sodium hydroxide solution, which contained 13.4 g of sodium hydroxide in 39 g of water. The monomer concentration was thereby adjusted at 45% (water content: 55%). Thereafter, 0.1 g of potassium persulfate was added and dissolved, and an aqueous monomer solution was thereby obtained.

Thereafter, the obtained aqueous monomer solution was added dropwise to the aforesaid fournecked round flask, into which cyclohexane and sorbitan monostearate had been introduced, under a nitrogen atmosphere. The temperature of the resulting mixture was then raised to 70 to 75° C., and polymerization was thereby begun.

Thereafter, the water content in a polymer, which was suspended in cyclohexane, was controlled at 35% by azeotropic dehydration (reflux for cyclohexane). An aqueous solution comprising 0.03 g of ethylene glycol diglycidyl ether in 1 ml of water was then added at a temperature of 73° C., and the resulting mixture was kept at that temperature for 2 hours. Cyclohexane was then removed, the product was dried at temperatures of 80 to 100° C. under reduced pressure, and an absorbent polymer (A) was thereby obtained.

EXAMPLE 2

Preparation of Absorbent Polymer

Into a 500-ml four-necked round flask, 40 g of the absorbent polymer (A) described above and 230 ml of cyclohexane were introduced. Water was then added to control the water content at 35%, and the temperature of the resulting mixture was raised to 75° C. After the temperature became constant (at 75° C.), ethylene glycol diglycidyl ether was added in a proportion of 2,500 ppm, based on the absorbent polymer (A) described above. Thereafter, the resulting mixture was kept at a temperature of 75° C. for 3 hours. Cyclohexane was then removed, the product was dried at temperatures of 80 to 100° C. under reduced pressure, and an absorbent polymer (B) was thereby obtained.

EXAMPLE 3

Preparation of Absorbent Polymer

A commercially available absorbent polymer (supplied under the trade name "Aquaric CAW-4" by Nippon Shokubai Co., Ltd.) was used as an absorbent polymer (C).

COMPARATIVE EXAMPLE 1

Preparation of Absorbent Polymer

A absorbent polymer (D) was prepared in the same manner as that for the absorbent polymer (A) described above, except that the temperature of the mixture in a 500-ml four-necked round flask, into which cyclohexane and sorbitan monostearate had been introduced, was raised to 70 to 75° C., the aqueous monomer solution described above was then added dropwise over 1.5 hours under a nitrogen atmosphere, polymerization being thereby carried out, and the mixture was then kept at temperatures of 70 to 75° C. for 0.5 hour in order to terminate the polymerization.

COMPARATIVE EXAMPLE 2

Preparation of Absorbent Polymer

A absorbent polymer (E) was prepared in the same manner as that for the absorbent polymer (D) described above, except that 1.94 g of ethyl cellulose (supplied under the trade name "N-200" by Hercules Far East) was used as a dispersing medium in lieu of "Rheodol SPS-12."

As for the highly absorbent polymers (A), (B), (C), (D), and (E) obtained in the manner described above, the degree of shape irregularity, the centrifugal retentive capacity for physiological saline, which was measured after equilibrium absorption swelling with the physiological saline, the permeation rate with respect to physiological saline, the centrifugal retentive capacity with respect to pseudo-blood, which was measured after equilibrium absorption swelling with the pseudo-blood, and the permeation rate with respect to pseudo-blood were measured. The results shown in Table 1 were obtained. The degree of shape irregularity was measured with the method described above. The centrifugal retentive capacity for physiological saline, which was measured after equilibrium absorption swelling with the physiological saline, the permeation rate with respect to physiological saline, the centrifugal retentive capacity with respect to pseudo-blood, which was measured after equilibrium absorption swelling with the pseudo-blood, and the permeation rate with respect to pseudo-blood were measured with the methods described below.

<Measurement of Centrifugal Retentive Capacity of Physiological Saline After Equilibrium Absorption Swelling>

One gram of the absorbent polymer was introduced into a beaker comprising 500 ml of physiological saline, and the mixture was left to stand for 30 minutes. The absorbent polymer, which had sufficiently absorbed physiological saline and had sufficiently been swollen, was included in a bag formed with paper and nonwoven fabric such that they may not fall from the bag. The bag comprising the absorbent polymer was put in a centrifugal separator (Model H-130C supplied by Kokusan Enshinki K.K.) and subjected to rotation at a rotation speed of 2,000 rpm (at a centrifugal acceleration of 895 G) for 10 minutes in order to determine the amount of the physiological saline perfectly secured to the polymer. Thereafter, the weight of the absorbent polymer was measured, and the centrifugal retentive capacity was calculated with the formula shown below.

Centrifugal retentive capacity (g/g)=[(weight after centrifugal separation)−(amount of absorbent polymer, i.e. 1 g)]/[amount of absorbent polymer, i.e. 1 g]

<Measurement of the Permeation Rate of Physiological Saline>

Figure 18:
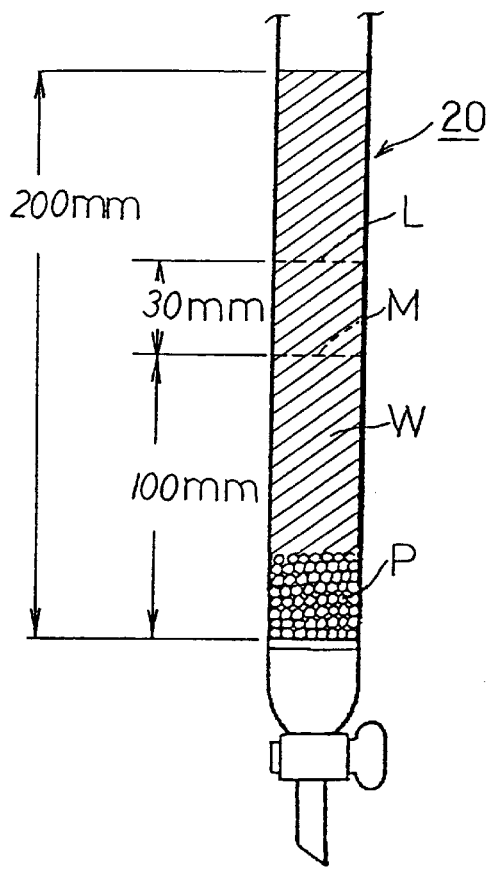
FIG. 18 is a schematic view showing an apparatus for measuring a permeation rate of physiological saline.

An apparatus 20 (a buret comprising a glass cylindrical tube having an inner diameter of 10 mm and a length of a cylindrical portion of approximately 250 mm) shown in FIG. 18 was packed with 0.05 g of the absorbent polymer P. The absorbent polymer P was swollen with an excess of physiological saline until the swelling reached equilibrium. The level of the physiological saline W was matched to the position of 200 mm, and the cock was closed. After the swollen polymer P was sufficiently settled as shown in FIG. 18, the cock was opened, and the time taken for the physiological saline W to pass between two gages L. and M (liquid amount: 5 ml) was measured. The permeation rate was then calculated with the formula shown below.

Permeation rate of absorbent polymer(ml liquid per minute)=[5 ml]/[time taken for the physiological saline to pass between gages L and M (minute)]

<Measurement of Centrifugal Retentive Capacity of Pseudo-blood After Equilibrium Absorption Swelling>

The centrifugal retentive capacity of pseudo-blood after equilibrium absorption swelling with the pseudo-blood was measured in the same manner as that for the centrifugal retentive capacity for physiological saline after equilibrium absorption swelling with the physiological saline, except that 500 ml of pseudo-blood prepared in the manner described below was used in lieu of the physiological saline.

<Measurement of the Permeation Rate of Pseudo-blood>

The permeation rate of pseudo-blood was measured in the same manner as that for the permeation rate with respect to physiological saline, except that pseudo-blood prepared in the manner described below was used in lieu of the physiological saline.

<Preparation of Pseudo-blood>

Into a beaker, 1,500 g of ion-exchanged water was introduced. Also, 5.3 g of carboxymethyl cellulose sodium salt was completely dissolved in the ion-ex-changed water. Thereafter, an additional 556-g portion of ion-exchanged water was prepared independently, and 27.0 g of NaCl and 12 g of $NaHCO_3$ were dissolved therein. The two solutions prepared in this manner and 900 g of glycerol were mixed together, and 15 ml of a solution comprising 1 g of a surface-active agent (supplied under the trade name "Emulgen 935" by Kao Corp.) per liter was added to the resulting mixture. Also, 0.3 g of Red No. 1 for food colorant was added to the resulting mixture and mixed until it was dissolved perfectly. The solution prepared in this manner was used as the pseudo-blood.

TABLE 1

| Absorbent polymer | Degree of shape irregularity (P) | Centrifugal retentive capacity of physiological saline (g/g) | Permeation rate of physiological saline (ml/min) | Centrifugal retentive capacity of pseudo-blood (g/g) | Permeation rate of pseudo-blood (ml/min) |
|---|---|---|---|---|---|
| A | 1.32 | 43.1 | 16.7 | 33.1 | 4.1 |
| B | 1.33 | 35.5 | 25.0 | 29.5 | 7.3 |
| C | 1.26 | 32.0 | 23.0 | 23.1 | 3.5 |
| D | 1.11 | 38.1 | 1.7 | 31.8 | 0.20 |
| E | 1.01 | 40.5 | 1.5 | 28.7 | 0.13 |

EXAMPLE 4

Preparation of Cellulose Fibers

One-hundred grams of mercerized pulp (supplied under the trade name "POROSANIER-J" by ITT Rayonier Inc.), which had a degree of fiber roughness of 0.36 mg/m and a degree of fiber roundness of 0.80, was dispersed in 1,000 g of an aqueous crosslinking agent solution, which contained 5% of dimethyloldihydroxyethyleneurea (supplied under the trade name "Sumitex Resin NS-19" by Sumitomo Chemical Co., Ltd.) serving as a crosslinking agent and 3% of a metal salt catalyst (supplied under the trade name "Sumitex Accelerator X-110" by Sumitomo Chemical Co., Ltd.). In this manner, the mercerized pulp was impregnated with the aqueous crosslinking agent solution.

Thereafter, the excess aqueous crosslinking agent solution was removed from the mercerized pulp until the proportion of the aqueous crosslinking agent solution with respect to the mercerized pulp became 200%. The mercerized pulp was then heated in an electric dryer at 135° C. for 10 minutes. The crosslinking in the cellulose molecule in the pulp and the crosslinking between the cellulose molecules in the pulp were thus carried out, and mercerized crosslinked pulp fibers were thereby obtained. The mercerized crosslinked pulp fibers, which had thus been obtained, were taken as cellulose fibers (A).

EXAMPLE 5

Preparation of Cellulose Fibers

One-hundred grams of softwood kraft pulp (supplied under the trade name "INDORAYON" by PT Inti Indorayon Utama), which had a degree of fiber-roughness of 0.35 mg/m and a degree of fiber roundness of 0.28, was dispersed in an aqueous crosslinking agent solution, which contained 5% of dimethyloldihydroxyethyleneurea (supplied under the trade name "Sumitex Resin NS-19" by Sumitomo Chemical Co., Ltd.) serving as a crosslinking agent and 5% of a metal salt catalyst (supplied under the trade name "Sumitex Accelerator X-110" by Sumitomo Chemical Co., Ltd.). In this manner, the softwood kraft pulp was impregnated with the aqueous crosslinking agent solution.

Thereafter, the excess aqueous crosslinking agent solution was removed from the softwood kraft pulp until the proportion of the aqueous crosslinking agent solution with respect to the kraft pulp became 200%. The kraft pulp was then heated in an electric dryer at 135° C. for 10 minutes. The crosslinking in the cellulose molecule in the pulp fibers and the crosslinking between the cellulose molecules in the pulp fibers were thus carried out, and crosslinked pulp fibers were thereby obtained. The crosslinked pulp fibers, which had thus been obtained, were taken as cellulose fibers (B).

EXAMPLE 6

Preparation of Cellulose Fibers

Crosslinked pulp fibers were prepared by carrying out the crosslinking reaction in the same manner as that in Example 4, except that rayon (supplied under the trade name "Corona SB Rayon" by Daiwabo Rayon K.K.), which had a degree of fiber roughness of 0.78 mg/m, a degree of fiber roundness of 0.68, and a length of 8 mm, was used. The crosslinked pulp fibers, which had thus been obtained, were taken as cellulose fibers (C).

COMPARATIVE EXAMPLE 3

Preparation of Cellulose Fibers

Softwood kraft pulp NBKP (supplied under the trade name "SKEENA PRIME" by Skeena Cellulose Co.), which had a degree of fiber roughness of 0.18 mg/m and a degree of fiber roundness of 0.32, was prepared. The softwood kraft pulp NBKP, which had thus been prepared, was taken as cellulose fibers (D).

COMPARATIVE EXAMPLE 4

Preparation of Cellulose Fibers

Softwood kraft pulp NBKP (supplied under the trade name "HARMAC-R" by MacMillan Bloedel, Ltd.), which had a degree of fiber roughness of 0.24 mg/m and a degree of fiber roundness of 0.34, was prepared. The softwood kraft pulp NBKP, which had thus been prepared, was taken as cellulose fibers (E).

COMPARATIVE EXAMPLE 5

Preparation of Cellulose Fibers

Crosslinked pulp fibers were prepared by carrying out the crosslinking reaction in the same manner as that in Example 4, except that softwood kraft pulp NBKP (supplied under the trade name "SKEENA PRIME" by Skeena Cellulose Co.), which had a degree of fiber roughness of 0.18 mg/m and a degree of fiber roundness of 0.32, was used. The crosslinked pulp fibers, which had thus been obtained, was taken as cellulose fibers (F).

As for the cellulose fibers (A) through (F) described above, the degree of fiber roughness, the degree of fiber roundness, and the residual strain after compression in a wet state were measured with the methods describe below. The results shown in Table 2 were obtained.

<Measurement of the Degree of Fiber Roughness>

Measurements were carried out with a fiber roughness meter FS-200 (supplied by KAJAANI ELECTRONICS LTD.). First, in order for the true weight of the cellulose fibers to be found, the cellulose fibers were dried in a vacuum dryer at 100° C. for 1 hour, and moisture was thereby removed from the cellulose fibers.

Thereafter, approximately 1 g of the cellulose fibers were quickly weighed accurately to a precision of ±0.1 mg. The cellulose fibers were then disaggregated perfectly in 150 ml of water by using a mixer attached to the fiber roughness meter such that they might not be damaged. The cellulose fibers disaggregated in water were then diluted with water to a volume of 5,000 ml. A 50 ml portion was accurately measured from the diluted liquid and taken as the liquid for the measurement of the fiber roughness. The degree of fiber roughness was then measured in accordance with the operation procedure for the fiber roughness meter.

<Measurement of Degree of Fiber Roundness>

The degree of fiber roundness of the cellulose fibers was measured in the manner described below. First, the cellulose fiber was sliced perpendicularly along the cross-sectional direction of the fiber such that the area of the cross section of the fiber might not change. A photograph of the cross section of the cellulose fiber was then taken by using an electron microscope. Thereafter, the photograph of the cross section of the cellulose fiber was analyzed with an image analyzer "Avio EXCEL" (supplied by Nippon Avionics Co., Ltd.), and the degree of fiber roundness of the cellulose fiber was calculated with the formula shown below. One hundred fiber cross sections were taken arbitrarily, their roundness values were measured, and the mean value of the measured roundness values was taken as the degree of fiber roundness of the cellulose fibers.

Degree of fiber roundness=[4×π×(fiber cross-sectional area of the measured fiber)]/[(circumferential length of the fiber cross section of the measured fiber)$^2$]

<Measurement of Residual Strain After Compression in Wet State>

The cellulose fibers were cut into a sheet having a basis weight of 500 g/m$^2$ and a size of 50 mm×50 mm. The sheet was adjusted such that it might have a thickness $1_0$ of 5.0±0.1 mm under a load of 5 g/cm$^2$. Thereafter, on the assumption that the sheet might be wetted with the excreted body fluid, 12.5 g (approximately 10 times as heavy as the weight of the sheet) of physiological saline was approximately uniformly applied to the entire sheet, and the entire sheet was thereby wetted. Thereafter, with a Tensilon compression tester, the wetted sheet was compressed under the conditions of a compression area of 10 cm$^2$ (a disk having a radius of 1.78 cm) and a compression rate of 10 mm/minute up to a maximum load of 200 g/cm$^2$ (i.e., 2,000 g per sheet). Thereafter, the pressure was removed at the equal rate. At this time, the physiological saline forced out from the pulp during the compression was removed by absorption with tissue paper This operation was repeated a total of 10 times, and compression measurements were carried out. Thereafter, the thickness $1_1$ of the sheet under a load of 5 g/cm$^2$ was measured. The residual strain after compression in a wet state was calculated with the formula shown below.

Residual strain after compression in wet state (%)=$(1_0-1_1)\times 100/1_0$

TABLE 2

|  | Dgree of fiber roughness (mg/m) | Degree of fiber roundness of fibers in cross section | Residual strain after compression in wet state (%) |
|---|---|---|---|
| Examples |  |  |  |
| 4 | 0.36 | 0.80 | 25 |
| 5 | 0.35 | 0.28 | 28 |
| 6 | 0.78 | 0.68 | 33 |
| Comp. Examples |  |  |  |
| 3 | 0.18 | 0.32 | 58 |
| 4 | 0.24 | 0.34 | 52 |
| 5 | 0.18 | 0.32 | 45 |

As is clear from Table 2, it can be found that, by the crosslinking of the cellulose fibers having a degree of fiber roughness of not lower than 0.3 mg/m, it becomes possible to keep the residual strain after compression in a wet state at a level lower than 40%. However, as for the cellulose fibers having a degree of fiber roughness of lower than 0.3 mg/m and the crosslinked cellulose fibers, which are obtained by crosslinking the cellulose fibers having a degree of their roughness of lower than 0.3 mg/m, the residual strain after compression in a wet state cannot be kept at a level lower than 40%. This indicates that such cellulose fibers collapse very easily when they are subjected to compression in a wet state. Therefore, with such cellulose fibers, the fiber spaces formed by the cellulose fibers cannot be maintained during the absorption of the body fluid, and the distance between the fibers cannot be kept stable.

EXAMPLE 7

Preparation of Absorbent Paper

In water, 95 parts by weight of the cellulose fibers (A) and 5 parts by weight of polyvinyl alcohol fibers (supplied under the trade name "Fibri Bond" by Sansho K.K.), which had a diameter of 1 denier and a length of 3 mm and which served as the thermally fusible bonding fibers, were respectively dispersed and mixed together. A paper was then prepared from the resulting mixture by using a paper machine and dried. In this manner, a permeable absorbent paper having a basis weight of 40 g/m$^2$ was obtained.

EXAMPLE 8

Preparation of Absorbent Paper

In water, 90 parts by weight of the cellulose fibers (B) and 10 parts by weight of polyethylene terephthalate fibers (hereinbelow referred to as PET fibers) (supplied under the trade name "TMOTNSB" by Teijin Ltd.), which had a diameter of 1.1 denier and a length of 5 mm and which served as the thermally fusible bonding fibers, were respectively dispersed and mixed together. A paper was then prepared from the resulting mixture by using a paper machine and dried. In this manner, a permeable absorbent paper having a basis weight of 40 g/m$^2$ was obtained.

EXAMPLE 9

Preparation of Absorbent Paper

In water, 70 parts by weight of the mercerized pulp fibers (supplied under the trade name "POROSANIER-J" by ITT Rayonier Inc.), which had a degree of fiber roughness of 0.36 mg/m (a fiber cross-sectional area of $3.8 \times 10^{-6}$ cm$^2$) and a degree of fiber roundness of 0.80 and which served as the bulky cellulose fibers, 20 parts by weight of rayon fibers (supplied under the trade name "Corona SB Rayon" by Daiwabo Rayon K.K. which had a degree of fiber roughness of 0.78 mg/m (a fiber cross-sectional area of $5.9 \times 10^{-6}$ cm$^2$), a degree of fiber roundness of 0.68, and a length of 8 mm and which served as the bulky cellulose fibers, 5 parts by weight of polyvinyl alcohol fibers (supplied under the trade name "Fibri Bond" by Sansho K.K.), which had a diameter of 1 denier and a length of 3 mm and which served as the thermally fusible bonding fibers, and 10 parts by weight of kraft pulp NBKP (supplied under the trade name "SKEENA PRIME" by Skeena Cellulose Co.), which served as the other constituent, were respectively dispersed and mixed together. A paper was then prepared from the resulting mixture by using a paper machine and dried. In this manner, a permeable absorbent paper having a basis weight of 40 g/m$^2$ was obtained.

COMPARATIVE EXAMPLE 6

Preparation of Absorbent Paper

In water, 100 parts by weight of the cellulose fibers (D) were dispersed. A paper was then prepared from the resulting dispersion by using a paper machine and dried. In this manner, an absorbent paper having a basis weight of 40 g/m$^2$ was obtained. This absorbent paper did not contain crosslinked cellulose fibers.

COMPARATIVE EXAMPLE 7

Preparation of Absorbent Paper

In water, 100 parts by weight of the cellulose fibers (F) were dispersed. A paper was then prepared from the resulting dispersion by using a paper machine and dried. In this manner, an absorbent paper having a basis weight of 40 g/m$^2$ was obtained.

COMPARATIVE EXAMPLE 8

Preparation of Absorbent Paper

In water, 100 parts by weight of softwood kraft pulp NBKP (supplied under the trade name "INDORAYON" by PT Inti Indorayon Utama), which had a degree of fiber roughness of 0.35 mg/m and a degree of fiber roundness of 0.28, was dispersed. A paper was then prepared from the resulting dispersion by using a paper machine and dried. In this manner, an absorbent paper having a basis weight of 40 g/m$^2$ was obtained.

COMPARATIVE EXAMPLE 9

Preparation of Absorbent Paper

In water, 40 parts by weight of the cellulose fibers (B) and 60 parts by weight of PET fibers (supplied under the trade name "TMOTNSB" by Teijin Ltd.), which had a diameter of 1.1 denier and a length of 5 mm and which served as the thermally fusible bonding fibers, were respectively dispersed and mixed together. A paper was then prepared from the resulting mixture by using a paper machine and dried. In this manner, an absorbent paper having a basis weight of 40 g/m$^2$ was obtained.

COMPARATIVE EXAMPLE 10

Preparation of Absorbent Paper

Rayon staple fibers (supplied by Daiwabo Rayon K.K.) having a diameter of 0.7 denier and a length of 38 mm were caused to entangle with one another with a water jet, and a nonwoven fabric having a basis weight of 40 g/m$^2$ was thereby obtained. This nonwoven fabric did not contain crosslinked cellulose fibers.

As for the absorbent paper obtained in Examples 7, 8, and 9 and Comparative Examples 6 through 10, the thickness under a load of 2.5 g/m$^2$, the absorption heights by Klemm's Method (after 1 minute and after 10 minutes) with respect to physiological saline, and the permeation time with respect to an 85% by weight aqueous glycerol solution were measured with the methods described below. The results shown in Table 3 were obtained.

<Measurement of Absorption Heights by Klemm's Method (After 1 Minute and After 10 minutes>

Figure 19:
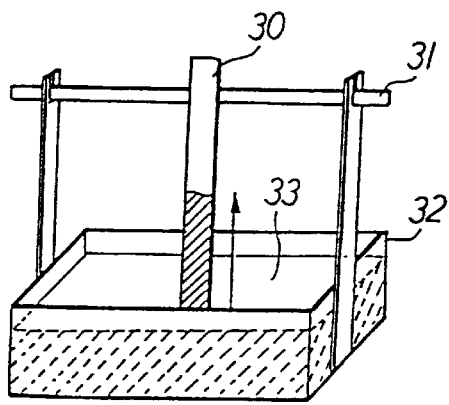
FIG. 19 is a schematic view showing an apparatus for measuring an absorption height of physiological saline by Klemm's Method.

The absorption height by Klemm's Method was measured by using a device shown in FIG. 19.

First, the absorbent paper was cut into test pieces 30 having a size of 300 mm×20 mm. Thereafter, as illustrated in FIG. 19, the test piece 30 was hung from a support 31, and the upper and lower ends of the test piece 30 were fixed such that it might not be slack. Also, a physiological saline 33 serving as a test liquid was introduced to a depth of 40 mm in a rectangular vessel 32 having a size of 300×100×50 mm (length×width×depth), and the test piece 30 was immersed in the physiological saline 33.

The height of the test liquid, which had been absorbed by the test piece 30, the height being taken from the surface of the test liquid, was measured 1 minute after the immersion of the test piece 30. Also, the height of the test liquid, which had been absorbed by the test piece 30, the height being taken from the surface of the test liquid, was measured 10 minutes after the immersion of the test piece 30.

For each of the absorption heights by Klemm's Method after 1 minute and after 10 minutes, the aforesaid test was repeated by using 10 test pieces, and a mean value of the 10 measured values was calculated. In this manner, the absorption height by Klemm's Method $h_1$ after 1 minute and the absorption height by Klemm's Method $h_{10}$ after 10 minutes were obtained.

<Measurement of Permeation Time for an 85% by Weight Aqueous Glycerol Solution>

Figure 20:
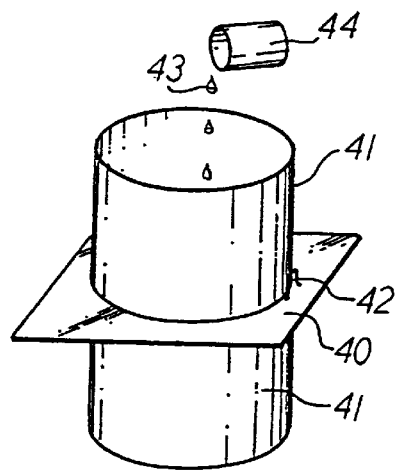
FIG. 20 is a schematic view showing an apparatus for measuring the permeation time of an aqueous glycerol solution.

The permeation time for an 85% by weight aqueous glycerol solution was measured by using an apparatus shown in FIG. 20.

First, the absorbent paper was cut into test pieces 40 having a size of 50 mm×50 mm as shown in FIG. 20. Thereafter, as illustrated in FIG. 20, the test piece 40 was sandwiched and fixed between the ends of upper and lower glass pipes 41, 41 having an inner diameter of 35 mm. At this time, the test piece 40 was fixed from both sides with clips (not shown) via a silicone rubber 42 such that no liquid would leak laterally during the measurement. As the test liquid, 10 g of an 85% by weight aqueous glycerol solution 43 was taken into a 10-ml beaker 44 and gently poured from the beaker 44 into the upper glass pipe 41. After the 85% by weight aqueous glycerol solution 43 had been poured into the upper glass pipe 41, the time taken for a portion of the surface of the test piece 40, which portion corresponded to at least 50% of the opening area of the glass pipe 41, to appear was measured. The time thus measured was taken as the liquid permeation time.

The test liquid (i.e., the 85% by weight aqueous glycerol solution) was prepared in the manner described below.

After mixing 85 g of glycerol (supplied by Wako Chemical Industries, Ltd.) with 15 g of ion-exchanged water, 0.01 g of Blue No. 1 for food (colorant supplied by Tokyo Kasei Kogyo K.K.) was added to the resulting mixture in order to color the test liquid in blue.

TABLE 3

|  | Absorption height by Klemm's Method (mm) | | Permeation time for an 85% by weight aqueous glycerol solution (seconds) | Thickness under a load of 2.5 g/m² (mm) |
| --- | --- | --- | --- | --- |
|  | After 1 minute ($h_1$) | After 10 minutes ($h_{10}$) | | |
| Examples | | | | |
| 7 | 35 | 60 | 8 | 0.76 |
| 8 | 42 | 75 | 12 | 0.55 |
| 9 | 55 | 90 | 29 | |
| Comp. Examples | | | | |
| 6 | 31 | 70 | 430 | 0.24 |
| 7 | 35 | 78 | 150 | 0.35 |
| 8 | 32 | 80 | 330 | 0.29 |
| 9 | 10 | 25 | 430 | 0.25 |
| 10 | 88 | 167 | 205 | 0.82 |

EXAMPLE 10

Preparation of Absorbent Paper

In water, 70 parts by weight of the cellulose fibers (A) and 30 parts by weight of kraft pulp NBKP (supplied under the trade name "SKEENA PRIME" by Skeena Cellulose Co.), which had a degree of fiber roughness of 0.18 mg/m and a degree of fiber roundness of 0.32 and which served as the hydrophilic fine fibers, were respectively dispersed and mixed together. A paper was then prepared from the resulting mixture by using a paper machine and dried. In this manner, a diffusing absorbent paper having a basis weight of 40 g/m² was obtained.

EXAMPLE 11

Preparation of Absorbent Paper

Thirty parts by weight of the cellulose fibers (C), 40 parts by weight of kraft pulp NBKP (supplied under the trade name "TYEE KRAFT" by Weyerhaeuser Canada, Ltd.), which had a degree of fiber roughness of 0.16 mg/m and a degree of fiber roundness of 0.31 and which served as the hydrophilic fine fibers, and 30 parts by weight of the mercerized pulp fibers (supplied under the trade name "POROSANIER-J" by ITT Rayonier Inc.), were mixed together. A paper was then prepared from the resulting mixture by using a paper machine and dried. In this manner, a diffusing absorbent paper having a basis weight of 40 g/m² was obtained.

EXAMPLE 12

Preparation of Absorbent Paper

In water, 75 parts by weight of the cellulose fibers (B) and 25 parts by weight of softwood kraft pulp NBKP (supplied under the trade name "SKEENA PRIME" by Skeena Cellulose Co.), which had a degree of fiber roughness of 0.18 mg/m and a degree of fiber roundness of 0.32 and which served as the hydrophilic fine fibers, were respectively dispersed and mixed together. A paper was then prepared from the resulting mixture by using a paper machine and dried. In this manner, a diffusing absorbent paper having a basis weight of 40 g/m² was obtained.

EXAMPLE 13

Preparation of Absorbent Paper

In water, 40 parts by weight of the cellulose fibers (A) and 60 parts by weight of softwood kraft pulp NBKP (supplied under the trade name "SKEENA. PRIME" by Skeena Cellulose Co.), which had a degree of fiber roughness of 0.18 mg/m and a degree of fiber roundness of 0.32 and which served as the hydrophilic fine fibers, were respectively dispersed and mixed together. A paper was then prepared from the resulting mixture by using a paper machine and dried. In this manner, a diffusing absorbent paper having a basis weight of 40 g/m² was obtained.

EXAMPLE 14

Preparation of Absorbent Paper

In water, 40 parts by weight of crosslinked pulp having a torsion structure [supplied under the trade name "High Bulk Additive" (hereinbelow referred to as "HBA") by Weyerhauser Paper], which served as the bulky cellulose fibers, 50 parts by weight of kraft pulp NBKP (supplied under the trade name "SKEENA PRIME" by Skeena Cellulose Co.), which had a degree of fiber roughness of 0.18 mg/m (a fiber cross-sectional area of $1.9 \times 10^{-6}$ cm²) and a degree of fiber roundness of 0.32 and which served as the hydrophilic fine fibers, and 10 parts by weight of PET fibers (supplied under the trade name "TMOTNSB" by Teijin Ltd.), which had a diameter of 1.1 denier and a length of 5 mm and which served as the thermally fusible bonding fibers, were respectively dispersed and mixed together. A paper was then prepared from the resulting mixture by using a paper machine and dried. In this manner, a diffusing absorbent paper having a basis weight of 40 g/m² was obtained.

EXAMPLE 15

Preparation of Absorbent Paper

In water, 60 parts by weight of the cellulose fibers (A) and 40 parts by weight of kraft pulp NBKP (supplied under the trade name "SKEENA PRIME" by Skeena Cellulose Co.), which had a degree of fiber roughness of 0.18 mg/m (a fiber cross-sectional area of $1.9 \times 10^{-6}$ cm²) and a degree of fiber roundness of 0.32 and which served as the hydrophilic fine fibers, were respectively dispersed and mixed together. A paper was then prepared from the resulting mixture by using a paper machine and dried. In this manner, a diffusing absorbent paper having a basis weight of 40 g/m² was obtained.

EXAMPLE 16

Preparation of Absorbent Paper

In water, 60 parts by weight of the cellulose fibers (A), 37 parts by weight of softwood kraft pulp NBKP (supplied under the trade name "SKEENA PRIME" by Skeena Cellulose Co.), which had a degree of fiber roughness of 0.18 mg/m and a degree of fiber roundness of 0.32 and which served as the hydrophilic fine fibers, and 3 parts by weight of polyvinyl alcohol fibers (supplied under the trade name "Fibri Bond" by Sansho K.K.), which had a diameter of 1 denier and a length of 3 mm and which served as the thermally fusible bonding fibers, were respectively dispersed and mixed together. A paper was then prepared from the resulting mixture by using a paper machine and dried. In this manner, a diffusing absorbent paper having a basis weight of 40 g/m² was obtained.

COMPARATIVE EXAMPLE 11

Preparation of Absorbent Paper

In water, kraft pulp NBKP (supplied under the trade name "SKEENA PRIME" by Skeena Cellulose Co.), which had a degree of fiber roughness of 0.18 mg/m (a fiber cross-sectional area of $1.9 \times 10^{-6}$ cm²) and a degree of fiber roundness of 0.32, was dispersed. A paper was then prepared from the resulting dispersion by using a paper machine and dried. In this manner, an absorbent paper having a basis weight of 40 g/m² was obtained.

COMPARATIVE EXAMPLE 12

Preparation of Absorbent Paper

In water, 60 parts by weight of softwood kraft pulp NBKP (supplied under the trade name "INDORAYON" by PT Inti Indorayon Utama), which had a degree of fiber roughness of 0.35 mg/m and a degree of fiber roundness of 0.28, and 40 parts by weight of softwood kraft pulp NBKP (supplied under the trade name "SKEENA PRIME" by Skeena Cellulose Co.), which had a degree of fiber roughness of 0.18 mg/m and a degree of fiber roundness of 0.32 and which served as the hydrophilic fine fibers, were respectively dispersed and mixed together. A paper was then prepared from the resulting mixture by using a paper machine and dried. In this manner, an absorbent paper having a basis weight of 40 g/m² was obtained. This absorbent paper did not contain crosslinked cellulose fibers.

COMPARATIVE EXAMPLE 13

Preparation of Absorbent Paper

In water, 60 parts by weight of the cellulose fibers (F) and 40 parts by weight of softwood kraft pulp NBKP (supplied under the trade name "SKEENA PRIME" by Skeena Cellulose Co.), which had a degree of fiber roughness of 0.18 mg/m and a degree of fiber roundness of 0.32 and which served as the hydrophilic fine fibers, were respectively dispersed and mixed together. A paper was then prepared from the resulting mixture by using a paper machine and dried. In this manner, an absorbent paper having a basis weight of 40 g/m² was obtained.

COMPARATIVE EXAMPLE 14

Preparation of Absorbent Paper

In water, 10 parts by weight of the cellulose fibers (B) and 90 parts by weight of softwood kraft pulp NBKP (supplied under the trade name "SKEENA PRIME" by Skeena Cellulose Co.), which had a degree of fiber roughness of 0.18 mg/m and a degree of fiber roundness of 0.32 and which served as the hydrophilic fine fibers, were respectively dispersed and mixed together. A paper was then prepared from the resulting mixture by using a paper machine and dried. In this manner, an absorbent paper having a basis weight of 40 g/m² was obtained.

COMPARATIVE EXAMPLE 15

Preparation of Absorbent Paper

In water, 30 parts by weight of the cellulose fibers (B), 30 parts by weight of softwood kraft pulp NBKP (supplied under the trade name "SKEENA PRIME" by Skeena Cellulose Co.), which had a degree of fiber roughness of 0.18 mg/m and a degree of fiber roundness of 0.32 and which served as the hydrophilic fine fibers, and 40 parts by weight of PET fibers (supplied under the trade name "TM0TNSB" by Teijin Ltd.), which had a diameter of 1.1 denier and a length of 5 mm and which served as the thermally fusible bonding fibers, were respectively dispersed and mixed together. A paper was then prepared from the resulting mixture by using a paper machine and dried. In this manner, an absorbent paper having a basis weight of 40 g/m² was obtained.

COMPARATIVE EXAMPLE 16

Preparation of Absorbent Paper

A dry-process pulp sheet (supplied under the trade name "Kinocloth" by Honshu Paper Co., Ltd.), which had a basis weight of 40 g/m², was prepared. This absorbent paper did not contain crosslinked cellulose fibers.

As for the absorbent paper obtained in Examples 10 through 16 and Comparative Examples 11 through 16, the thickness under a load of 2.5 g/m², the absorption heights by Klemm's Method (after 1 minute and after 10 minutes) with respect to physiological saline, and the permeation time with respect to an 85% by weight aqueous glycerol solution were measured. The results shown in Table 4 were obtained.

TABLE 4

| | Absorption height by Klemm's Method (mm) | | Permeation time for an 85% by weight aqueous glycerol solution (seconds) | Thickness under a load of 2.5 g/m² (mm) |
|---|---|---|---|---|
| | After 1 minute ($h_1$) | After 10 minutes ($h_{10}$) | | |
| Examples | | | | |
| 10 | 82 | 235 | 35 | 0.50 |
| 11 | 67 | 185 | 43 | |
| 12 | 66 | 134 | 22 | 0.43 |
| 13 | 90 | 160 | 68 | 0.34 |
| 14 | 71 | 141 | 68 | |
| 15 | 76 | 183 | 45 | |
| 16 | 78 | 230 | 43 | 0.42 |
| Comp. Examples | | | | |
| 11 | 31 | 70 | 430 | 0.24 |
| 12 | 31 | 75 | 350 | 0.26 |
| 13 | 32 | 74 | 290 | 0.30 |
| 14 | 30 | 67 | 390 | 0.25 |
| 15 | 45 | 82 | 245 | 0.28 |
| 16 | 3 | 4 | 130 | |

EXAMPLE 17

Preparation of Absorbent Paper

In water, 95 parts by weight of the cellulose fibers (A) and 5 parts by weight of polyvinyl alcohol fibers (supplied under the trade name "Fibri Bond" by Sansho K.K.), which had a diameter of 1 denier and a length of 3 mm and which served as the thermally fusible bonding fibers, were respectively dispersed and mixed together. A paper layer of a permeable absorbent paper was then formed from the resulting mixture on a wire by using a first paper machine.

Also, in an independent operation, 70 parts by weight of the cellulose fibers (A) and 30 parts by weight of softwood kraft pulp NBKP (supplied under the trade name "TYEE KRAFT" by Weyerhaeuser Canada, Ltd.), which had a degree of fiber roughness of 0.16 mg/m and a degree of fiber roundness of 0.31 and which served as the hydrophilic fine fibers, were dispersed and mixed together in water. A paper layer of a diffusing absorbent paper was then formed from the resulting mixture on a wire by using a second paper machine.

The two paper layers were taken up from the respective wires, overlaid one upon the other, pressed, dehydrated, and dried. In this manner, the composite absorbent paper having the structure shown in FIG. 5 was obtained. The total basis weight of the composite absorbent paper was 80 g/m$^2$. The basis weight of the permeable absorbent paper and the basis weight of the diffusing absorbent paper were respectively equal to 40 g/m$^2$.

EXAMPLE 18

Preparation of Absorbent Paper

As an absorbent sheet, a composite absorbent paper comprising a permeable absorbent paper, which had been obtained in the same manner as that in Example 7, and a diffusing absorbent paper, which had been obtained in the same manner as that in Example 10, was prepared.

Specifically, for the formation of the permeable absorbent paper, 95 parts by weight of the cellulose fibers (A) and 5 parts by weight of polyvinyl alcohol fibers (supplied under the trade name "Fibri Bond" by Sansho K.K.), which had a diameter of 1 denier and a length of 3 mm and which served as the thermally fusible bonding fibers, were respectively dispersed and mixed together in water. A paper layer of the permeable absorbent paper was then formed from the resulting mixture on a wire by using a first paper machine.

Also, in an independent operation, for the formation of the diffusing absorbent paper, 70 parts by weight of the cellulose fibers (A) and 30 parts by weight of softwood kraft pulp NBKP (supplied under the trade name "SKEENA PRIME" by Skeena Cellulose Co.), which had a degree of fiber roughness of 0.18 mg/m and a degree of fiber roundness of 0.32 and which served as the hydrophilic fine fibers, were respectively dispersed and mixed together in water. A paper layer of the diffusing absorbent paper was then formed from the resulting mixture on a wire by using a second paper machine.

The two paper layers were taken up from the respective wires, overlaid one upon the other, pressed, dehydrated, and dried. In this manner, the composite absorbent paper having the structure shown in FIG. 5 was obtained. The total basis weight of the composite absorbent paper was 80 g/m$^2$. The basis weight of the permeable absorbent paper and the basis weight of the diffusing absorbent paper were respectively equal to 40 g/m$^2$.

The permeable absorbent paper and the diffusing absorbent paper in this composite absorbent paper had the absorption heights by Klemm's Method and the permeation rates with respect to an aqueous glycerol solution respectively shown in Tables 3 and 4.

EXAMPLE 19

Preparation of Absorbent Paper

As an absorbent sheet, a composite absorbent paper comprising a permeable absorbent paper, which had been obtained in the same manner as that in Example 8, and a diffusing absorbent paper, which had been obtained in the same manner as that in Example 12, was prepared.

Specifically, for the formation of the permeable absorbent paper, 90 parts by weight of the cellulose fibers (B) and 10 parts by weight of PET fibers (supplied under the trade name "TMOTNSB" by Teijin Ltd.), which had a diameter of 1.1 denier and a length of 5 mm and which served as the thermally fusible bonding fibers, were respectively dispersed and mixed together in water. A paper layer of the permeable absorbent paper was then formed from the resulting mixture on a wire by using a first paper machine.

Also, in an independent operation, for the formation of the diffusing absorbent paper, 75 parts by weight of the cellulose fibers (B) and 25 parts by weight of softwood kraft pulp NBKP (supplied under the trade name "SKEENA PRIME" by Skeena Cellulose Co.), which had a degree of fiber roughness of 0.18 mg/m and a degree of fiber roundness of 0.32 and which served as the hydrophilic fine fibers, were respectively dispersed and mixed together in water. A paper layer of the diffusing absorbent paper was then formed from the resulting mixture on a wire by using a second paper machine.

The two paper layers were taken up from the respective wires, overlaid one upon the other, pressed, dehydrated, and dried. In this manner, the composite absorbent paper having the structure shown in FIG. 5 was obtained. The total basis weight of the composite absorbent paper was 80 g/m$^2$. The basis weight of the permeable absorbent paper and the basis weight of the diffusing absorbent paper were respectively equal to 40 g/m$^2$.

The permeable absorbent paper and the diffusing absorbent paper in this composite absorbent paper had the absorption heights by Klemm's Method and the permeation rates with respect to an aqueous glycerol solution respectively shown in Tables 3 and 4.

EXAMPLE 20

Preparation of Absorbent Paper

As an absorbent sheet, a composite absorbent paper comprising a permeable absorbent paper, which had been obtained in the same manner as that in Example 7, and a diffusing absorbent paper, which had been obtained in the same manner as that in Example 16, was prepared.

Specifically, for the formation of the permeable absorbent paper, 95 parts by weight of the cellulose fibers (A) and 5 parts by weight of polyvinyl alcohol fibers (supplied under the trade name "Fibri Bond" by Sansho K.K.), which had a diameter of 1 denier and a length of 3 mm and which served as the thermally fusible bonding fibers, were respectively dispersed and mixed together in water. A paper layer of the permeable absorbent paper was then formed from the resulting mixture on a wire by using a first paper machine.

Also, in an independent operation, for the formation of the diffusing absorbent paper, 60 parts by weight of the cellulose fibers (A), 37 parts by weight of softwood kraft pulp NBKP (supplied under the trade name "SKEENA PRIME" by Skeena Cellulose Co.), which had a degree of fiber roughness of 0.18 mg/m and a degree of fiber roundness of 0.32 and which served as the hydrophilic fine fibers, and 3 parts by weight of polyvinyl alcohol fibers (supplied under the trade name "Fibri Bond" by Sansho K.K.), which had a diameter of 1 denier and a length of 3 mm and which served as the thermally fusible bonding fibers, were respectively dispersed and mixed together in water. A paper layer of the diffusing absorbent paper was then formed from the resulting mixture on a wire by using a second paper machine.

The two paper layers were taken up from the respective wires, overlaid one upon the other, pressed, dehydrated, and dried. In this manner, the composite absorbent paper having the structure shown in FIG. 5 was obtained. The total basis weight of the composite absorbent paper was 80 g/m$^2$. The basis weight of the permeable absorbent paper and the basis weight of the diffusing absorbent paper were respectively equal to 40 g/m$^2$.

The permeable absorbent paper and the diffusing absorbent paper in this composite absorbent paper had the absorption heights by Klemm's Method and the permeation rates with respect to an aqueous glycerol solution respectively shown in Tables 3 and 4.

EXAMPLE 21

Preparation of Absorbent Paper

As an absorbent sheet, a composite absorbent paper comprising a permeable absorbent paper, which had been obtained in the same manner as that in Example 7, a diffusing absorbent paper, which had been obtained in the same manner as that in Example 10, and a polymer dispersing paper was prepared.

Specifically, for the formation of the permeable absorbent paper, 95 parts by weight of the cellulose fibers (A) and 5 parts by weight of polyvinyl alcohol fibers (supplied under the trade name "Fibri Bond" by Sansho K.K.), which had a diameter of 1 denier and a length of 3 mm and which served as the thermally fusible bonding fibers, were respectively dispersed and mixed together in water. A paper layer of the permeable absorbent paper was then formed from the resulting mixture on a wire by using a first paper machine.

Also, in an independent operation, for the formation of the diffusing absorbent paper, 70 parts by weight of the cellulose fibers (A) and 30 parts by weight of softwood kraft pulp NBKP (supplied under the trade name "SKEENA PRIME" by Skeena Cellulose Co.), which had a degree of fiber roughness of 0.18 mg/m and a degree of fiber roundness of 0.32 and which served as the hydrophilic fine fibers, were respectively dispersed and mixed together in water. A paper layer of the diffusing absorbent paper was then formed from the resulting mixture on a wire by using a second paper machine.

Further, in an independent operation, for the formation of the polymer dispersing paper, 98 parts by weight of the cellulose fibers (A) and 2 parts by weight of polyvinyl alcohol fibers (supplied under the trade name "Fibri Bond" by Sansho K.K.), which had a diameter of 1 denier and a length of 3 mm and which served as the thermally fusible bonding fibers, were respectively dispersed and mixed together in water. A paper layer of the polymer dispersing paper was then formed from the resulting mixture on a wire by using a third paper machine.

The three paper layers were taken up from the respective wires, overlaid one upon another in the order of the permeable absorbent paper, the diffusing absorbent paper, and the polymer dispersing paper. Thereafter, the resulting combination of the paper layers was pressed, dehydrated, and dried. In this manner, the composite absorbent paper having the structure shown in FIG. 7 was obtained. The total basis weight of the composite absorbent paper was 100 g/m$^2$. The basis weight of the permeable absorbent paper and the basis weight of the diffusing absorbent paper were respectively equal to 40 g/m$^2$. The basis weight of the polymer dispersing paper was 20 g/m$^2$.

The permeable absorbent paper and the diffusing absorbent paper in this composite absorbent paper had the absorption heights by Klemm's Method and the permeation rates with respect to an aqueous glycerol solution respectively shown in Tables 3 and 4.

EXAMPLE 22

Preparation of Absorbent Paper

In water, 95 parts by weight of the cellulose fibers (A) and 5 parts by weight of polyvinyl alcohol fibers (supplied under the trade name "Fibri Bond" by Sansho K.K.), which had a diameter of 1 denier and a length of 3 mm and which served as the thermally fusible bonding fibers, were respectively dispersed and mixed together. A paper layer of a permeable absorbent paper was then formed from the resulting mixture on a wire by using a first paper machine.

Also, in an independent operation, 70 parts by weight of the cellulose fibers (A) and 30 parts by weight of softwood kraft pulp NBKP (supplied under the trade name "TYEE KRAFT" by Weyerhaeuser Canada, Ltd.), which had a degree of fiber roughness of 0.16 mg/m and a degree of fiber roundness of 0.31 and which served as the hydrophilic fine fibers, were respectively dispersed and mixed together in water. A paper layer of a diffusing absorbent paper was then formed from the resulting mixture on a wire by using a second paper machine.

Further, in an independent operation, 98 parts by weight of the cellulose fibers (A) and 2 parts by weight of polyvinyl alcohol fibers (supplied under the trade name "Fibri Bond" by Sansho K.K.), which served as the thermally fusible bonding fibers, were respectively dispersed and mixed together in water. A paper layer of a polymer dispersing paper was then formed from the resulting mixture on a wire by using a third paper machine.

The three paper layers were taken up from the respective wires, overlaid one upon another in the order of the permeable absorbent paper, the diffusing absorbent paper, and the polymer dispersing paper. Thereafter, the resulting combination of the paper layers was pressed, dehydrated, and dried. In this manner, the composite absorbent paper having the structure shown in FIG. 7 was obtained. The total basis weight of the composite absorbent paper was 100 g/m$^2$. The basis weight of the permeable absorbent paper and the basis weight of the diffusing absorbent paper were respectively equal to 40 g/m$^2$. The basis weight of the polymer dispersing paper was 20 g/m$^2$.

COMPARATIVE EXAMPLE 17

Preparation of Absorbent Paper

As an absorbent sheet, a composite absorbent paper comprising an absorbent paper, which had been obtained in the same manner as that in Comparative Example 7, and an absorbent paper, which had been obtained in the same manner as that in Comparative Example 13, was prepared.

Specifically, for the formation of the absorbent paper according to Comparative Example 7, 100 parts by weight of the cellulose fibers (F) were dispersed in water. A paper layer of the first absorbent paper was then formed from the resulting dispersion on a wire by using a first paper machine.

Also, in an independent operation, for the formation of the absorbent paper according to Comparative Example 13, 60 parts by weight of the cellulose fibers (F) and 40 parts by weight of softwood kraft pulp NBKP (supplied under the trade name "SKEENA PRIME" by Skeena Cellulose Co.), which had a degree of fiber roughness of 0.18 mg/m and a degree of fiber roundness of 0.32 and which served as the hydrophilic fine fibers, were respectively dispersed and mixed together in water. A paper layer of the second absorbent paper was then formed from the resulting mixture on a wire by using a second paper machine.

The two paper layers were taken up from the respective wires, overlaid one upon the other, pressed, dehydrated, and dried. In this manner, the composite absorbent paper having the structure shown in FIG. 5 was obtained. The total basis weight of the composite absorbent paper was 80 g/m². The basis weight of the first absorbent paper, which had been obtained in the same manner as that in Comparative Example 7, and the basis weight of the second absorbent paper, which had been obtained in the same manner as that in Comparative Example 13, were respectively equal to 40 g/m².

In this composite absorbent paper, the first absorbent paper, which had been obtained in the same manner as that in Comparative Example 7, and the second absorbent paper, which had been obtained in the same manner as that in Comparative Example 13, had the absorption heights by Klemm's Method and the permeation rates with respect to an aqueous glycerol solution respectively shown in Tables 3 and 4.

COMPARATIVE EXAMPLE 18

Preparation of Absorbent Paper

As an absorbent sheet, a composite absorbent paper comprising an absorbent paper, which had been obtained in the same manner as that in Comparative Example 8, and an absorbent paper, which had been obtained in the same manner as that in Comparative Example 11, was prepared.

Specifically, for the formation of the absorbent paper according to Comparative Example 8, 100 parts by weight of softwood kraft pulp NBKP (supplied under the trade name "INDORAYON" by PT Inti Indorayon Utama), which had a degree of fiber roughness of 0.35 mg/m and a degree of fiber roundness of 0.28, was dispersed in water. A paper layer of the first absorbent paper was then formed from the resulting dispersion on a wire by using a first paper machine.

Also, in an independent operation., for the formation of the absorbent paper according to comparative Example 11, 100 parts by weight of softwood kraft pulp NBKP (supplied under the trade name "SKEENA PRIME" by Skeena Cellulose Co.), which had a degree of fiber roughness of 0.18 mg/m and a degree of fiber roundness of 0.32, were dispersed in water. A paper layer of the second absorbent paper was then formed from the resulting dispersion on a wire by using a second paper machine.

The two paper layers were taken up from the respective wires, overlaid one upon the other, pressed, dehydrated, and dried. In this manner, the composite absorbent paper having the structure shown in FIG. 5 was obtained. The total basis weight of the composite absorbent paper was 80 g/m². The basis weight of the first absorbent paper, which had been obtained in the same manner as that in Comparative Example 8, and the basis weight of the second absorbent paper, which had been obtained in the same manner as that in Comparative Example 11, were respectively equal to 40 g/m².

In this composite absorbent paper, the first absorbent paper, which had been obtained in the same manner as that in Comparative Example 8, and the second absorbent paper, which had been obtained in the same manner as that in Comparative Example 11, had the absorption heights by Klemm's Method and the permeation rates with respect to an aqueous glycerol solution respectively shown in Tables 3 and 4.

COMPARATIVE EXAMPLE 19

Preparation of Absorbent Paper

As an absorbent sheet, a composite absorbent paper comprising an absorbent paper, which had been obtained in the same manner as that in Comparative Example 7, an absorbent paper, which had been obtained in the same manner as that in Comparative Example 13, and a polymer dispersing paper was prepared.

Specifically, for the formation of the absorbent paper according to Comparative Example 7, 100 parts by weight of the cellulose fibers (F) were dispersed in water. A paper layer of the first absorbent paper was then formed from the resulting dispersion on a wire by using a first paper machine.

Also, in an independent operation, for the formation of the absorbent paper according to Comparative Example 13, 60 parts by weight of the cellulose fibers (F) and 40 parts by weight of softwood kraft pulp NBKP (supplied under the trade name "SKEENA PRIME" by Skeena Cellulose Co.), which had a degree of fiber roughness of 0.18 mg/m and a degree of fiber roundness of 0.32 and which served as the hydrophilic fine fibers, were respectively dispersed and mixed together in water. A paper layer of the second absorbent paper was then formed from the resulting mixture on a wire by using a second paper machine.

Further, in an independent operation, for the formation of the polymer dispersing paper, 100 parts by weight of the cellulose fibers (F) were dispersed in water. A paper layer of the polymer dispersing paper was then formed from the resulting dispersion on a wire by using a third paper machine.

The three paper layers were taken up from the respective wires, overlaid one upon another in the order of the first absorbent paper, the second absorbent paper, and the polymer dispersing paper. Thereafter, the resulting combination of the paper layers was pressed, dehydrated, and dried. In this manner, the composite absorbent paper having the structure shown in FIG. 7 was obtained. The total basis weight of the composite absorbent paper was 100 g/m2. The basis weight of the first absorbent paper, which had been obtained in the same manner as that in Comparative Example 7, and the basis weight of the second absorbent paper, which had been obtained in the same manner as that in Comparative Example 13, were respectively equal to 40 g/m². The basis weight of the polymer dispersing paper was 20 g/m².

In this composite absorbent paper, the first absorbent paper, which had been obtained in the same manner as that in Comparative Example 7, and the second absorbent paper, which had been obtained in the same manner as that in Comparative Example 13, had the absorption heights by Klemm's Method and the permeation rates with respect to an aqueous glycerol solution respectively shown in Tables 3 and 4.

EXAMPLE 23

Preparation of Absorbent Article

As the cellulose fibers $2a$, the cellulose fibers (A), which had been adjusted so as to have a basis weight of 150 g/m² and a size of a length of 175 mm and a width of 73 mm, were used. As the absorbent polymer $2b$, 0.5 g of the absorbent polymer (A) was spread to the cellulose fibers (A) such that the basis weight might become equal to 39 g/m². The absorbent polymer (A) was thus dispersed and mixed with the cellulose fibers (A). The resulting mixture was adjusted so as to have a thickness of 1 mm and was included and covered with the permeable absorbent paper 2c. As the permeable absorbent paper 2c, the permeable absorbent paper obtained in Example 7 was cut to a length of 175 mm and a width of 160 mm, and the thus cut paper was used. In this manner, the absorbent member 2 having the configuration shown in FIG. 1 was obtained.

The obtained absorbent member 2 was wrapped up in a polyethylene-laminated waterproof paper, which served as the back sheet 3 and had a length of 205 mm and a width of 95 mm. The absorbent member 2, which had been wrapped up in the back sheet 3, was then included in the liquid-permeable topsheet 1 having a length of 205 mm and a width of 172 mm. The absorbent member 2 was secured by using a thermally fusible bonding as the joints 6, 6, . . . Further, as the adhesive parts 4, 4, 4, a thermally fusible bonding was applied along three lines with a basis weight of 30 g/m², a width of 10 mm and a length of 115 mm. In this manner, a sanitary napkin having the configuration shown in FIG. 1 was obtained.

The liquid-permeable topsheet 1 described above was prepared in the manner described below.

Figure 21:
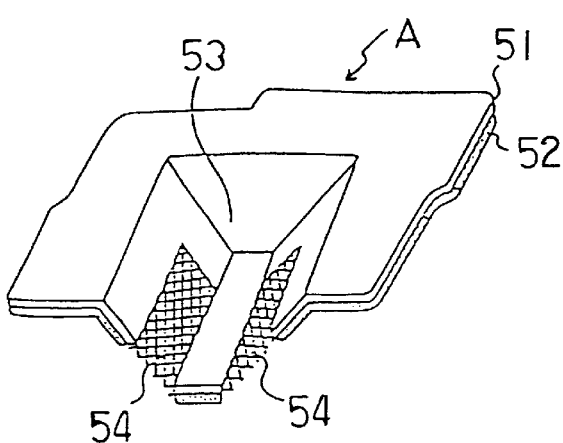
FIG. 21 is an enlarged sectional view showing part of a topsheet.

Specifically, as illustrated in FIG. 21, a nonwoven fabric 52 having a basis weight of 25 g/m² was prepared with a dry hot gluing method from polyethylene/polypropylene composite fibers (supplied by Chisso Corp.), to which 0.34% by weight of a mixed surfactant of an alkyl phosphate and a sorbitan fatty acid ester had been adhered. A low-density polyethylene film 51 having a thickness of 25 μm (supplied by Mitsui Petro-chemical Industries, Ltd.) was then laminated with the nonwoven fabric 52.

The topsheet 1 had a wall portion 53. The wall portion 53 was provided with openings 54, which had a size of 0.1 to 2 mm², at a density of 52 openings/cm². The topsheet 1 had a hydrophobic surface constituted of the low-density polyethylene film 51 and a hydrophilic surface constituted of the nonwoven fabric 52. Methods for producing the topsheet are described in, for example, Japanese Patent Laid-open Application 64-34365 and 1-258953, which are incorporated herein by reference.

EXAMPLE 24

Preparation of Absorbent Article

As the cellulose fibers 2a, the cellulose fibers (B), which had been adjusted so as to have a basis weight of 150 g/m² and a size of a length of 175 mm and a width of 73 mm, were used. As the absorbent polymer 2b, 0.5 g of the absorbent polymer (B) was spread to the cellulose fibers (B) such that the basis weight might become equal to 39 g/m². The resulting mixture was adjusted so as to have a thickness of 1 mm and was included and covered with the permeable absorbent paper 2c. As the permeable absorbent paper 2c, the permeable absorbent paper obtained in Example 8 was cut to a length of 175 mm and a width of 160 mm, and the thus cut paper was used. In this manner, an absorbent member 2 having the configuration shown in FIG. 1 was obtained.

The other procedures were carried out in the same manner as that in Example 23, and a sanitary napkin having the configuration shown in FIG. 1 was obtained.

EXAMPLE 25

Preparation of absorbent article

As the diffusing absorbent paper 2d for including and covering an absorbent polymer, the diffusing absorbent paper, which had been obtained in Example 10 and had a length of 175 mm and a width of 190 mm, was used. A thermally fusible bonding was spread in a spiral pattern in a proportion of approximately 10 g/m² on the diffusing absorbent paper. Thereafter, as the absorbent polymer 2b, 0.5 g of the absorbent polymer (A) was spread approximately uniformly (at a basis weight of approximately 39 g/m²) over an area of a length of 175 mm and a width of 73 mm on the diffusing absorbent paper. The two ends of the diffusing absorbent paper were then turned up in order to include and cover the absorbent polymer (A) such that the absorbent polymer (A) might not fall from the diffusing absorbent paper. In this manner, the diffusing absorbent paper and the absorbent polymer (A) were combined with each other into a unitary body having a width of 73 mm. The integral body thus obtained was then included and covered with the permeable absorbent paper 2c. As the permeable absorbent paper 2c, the permeable absorbent paper obtained in Example 7 was cut to a length of 175 mm and a width of 130 mm, and the thus cut paper was used. In this manner, an absorbent member 2 having the configuration shown in FIG. 2 was obtained.

The other procedures were carried out in the same manner as that in Example 23, and a sanitary napkin having the configuration shown in FIG. 2 was obtained.

EXAMPLE 26

Preparation of Absorbent Article

An absorbent member 2 having the configuration shown in FIG. 2 was obtained in the same manner as that in Example 25, except that the diffusing absorbent paper obtained in Example 11 was used in lieu of the diffusing absorbent paper used in Example 25 (which was obtained in Example 10), and the absorbent polymer (C) was used in lieu of the absorbent polymer (A).

The other procedures were carried out in the same manner as that in Example 23, and a sanitary napkin having the configuration shown in FIG. 2 was obtained.

EXAMPLE 27

Preparation of Absorbent Article

As the composite absorbent paper 2f, the composite absorbent paper, which had been obtained in Example 17, was cut to a length of 175 mm and a width of 150 mm, and the cut paper thus obtained was used. A thermally fusible bonding was spread in a spiral pattern in a proportion of approximately 10 g/m² on the side of the diffusing absorbent paper of the composite absorbent paper. Thereafter, as the absorbent polymer 2b, 0.5 g of the absorbent polymer (A) was spread approximately uniformly (at a basis weight of approximately 39 g/m²) over an area of a length of 175 mm and a width of 73 mm on the composite absorbent paper. The two ends of the composite absorbent paper along its longitudinal direction were then turned up such that a unitary body having a width of 73 mm might be obtained. In this manner, an absorbent member 2 having the configuration shown in FIG. 4 was obtained.

The other procedures were carried out in the same manner as that in Example 23, and a sanitary napkin having the configuration shown in FIG. 4 was obtained.

EXAMPLES 28, 29, and 30

Preparation of Absorbent Article

A sanitary napkin was obtained in the same manner as that in Example 27, except that the composite absorbent paper obtained in each of Examples 18, 19, and 20 was used as the composite absorbent paper 2f used in Example 27, and 1.5 g of the absorbent polymer was spread.

COMPARATIVE EXAMPLE 20

Preparation of Absorbent Article

A sanitary napkin having the configuration shown in FIG. 1 was obtained in the same manner as that in Example 23, except that the cellulose fibers (D) were used in lieu of the cellulose fibers (A), the absorbent polymer (D) was used in lieu of the absorbent polymer (A), and the absorbent paper obtained in Comparative Example 6 was used in lieu of the permeable absorbent paper obtained in Example 7.

COMPARATIVE EXAMPLE 21

Preparation of Absorbent Article

A sanitary napkin having the configuration shown in FIG. 1 was obtained in the same manner as that in Example 23, except that the cellulose fibers (F) were used in lieu of the cellulose fibers (A), the absorbent polymer (E) was used in lieu of the absorbent polymer (A), and the absorbent paper obtained in Comparative Example 10 was used in lieu of the permeable absorbent paper obtained in Example 7.

COMPARATIVE EXAMPLE 22

Preparation of Absorbent Article

A sanitary napkin having the configuration shown in FIG. 1 was obtained in the same manner as that in Example 23, except that the cellulose fibers (D) were used in lieu of the cellulose fibers (A.), the absorbent polymer (C) was used in lieu of the absorbent polymer (A), and the absorbent paper obtained in Comparative Example 6 was used in lieu of the permeable absorbent paper obtained in Example 7.

COMPARATIVE EXAMPLE 23

Preparation of Absorbent Article

A sanitary napkin having the configuration shown in FIG. 2 was obtained in the same manner as that in Example 25, except that the absorbent paper obtained in Comparative Example 16 was used in lieu of the diffusing absorbent paper obtained in Example 10, the absorbent polymer (C) was used in lieu of the absorbent polymer (A), and the absorbent paper obtained in Comparative Example 6 was used in lieu of the permeable absorbent paper obtained in Example 7.

As for the sanitary napkins obtained in Examples 23 through 30 and Comparative Examples 20, 21, 22, and 23, the tests for the absorption time, the dynamic quantity of reflow, and leakage were carried out with the methods described below. The results shown in Table 5 were obtained.

<Measurement of Absorption Time (5 g), Reabsorption Time (10 g), and Dynamic Quantity of Reflow>

Figure 22:
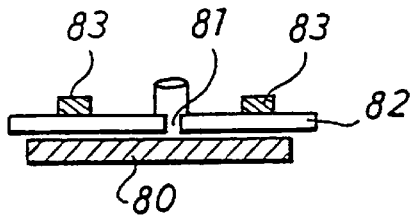
FIG. 22 is a schematic view showing how the blood absorption time is measured.

As illustrated in FIG. 22, a sanitary napkin 80 obtained in each of Examples 23 through 30 and Comparative Examples 20, 21, 22, and 23 was horizontally placed. An acrylic plate 82 having an inlet 81 having a diameter of 10 mm was placed on the sanitary napkin 80. Weights 83, 83 were then placed on the acrylic plate 82 such that a load of 5 g/cm$^2$ might be applied to the sanitary napkin 80.

Thereafter, 5 g of defibrinated equine blood (supplied by Nippon Biotest Laboratories) was poured from the inlet 81, and the absorption time (in seconds) taken for the liquid to be absorbed completely was measured. Also, after the liquid had been absorbed completely, the sanitary napkin 80 was left to stand for 20 minutes. Thereafter, 5 g of defibrinated equine blood was again poured, the reabsorption time (for 10 g) was measured. The sanitary napkin 80 was then left to stand for 20 minutes.

Figure 24:
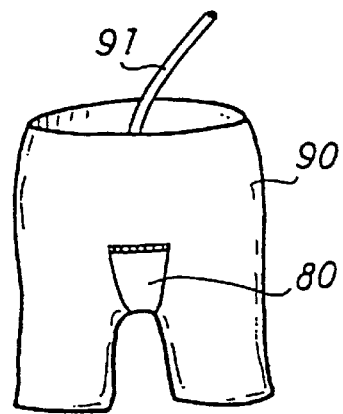
FIG. 24 is a schematic view showing how a sanitary napkin is put on the crotch of the movable model of the hip of a woman shown in FIG. 23.
Figure 23:
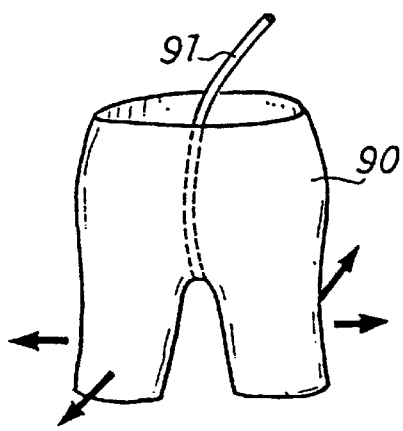
FIG. 23 is a schematic view showing a movable model of the hip of a woman.

Thereafter, ten absorbent elements composed of softwood pulp, which had a width of 75 mm and a length of 195 mm, and a basis weight of 30 g/cm$^2$, were placed on the upper surface of the sanitary napkin 80 (i.e., on the side in contact with the user's skin). As illustrated in FIG. 24, shorts, to which the sanitary napkin 80 having the absorbent elements placed thereon had been fitted, were then put on a movable female hip model 90 shown in FIG. 23. Thereafter, the model 90 was caused to walk at a walking speed of 100 steps/minute (i.e, 50 m/minute) for 1 minute.

After the walking had been finished, the sanitary napkin 80 and the 10 absorbent elements were taken out, and the weight of the defibrinated equine blood absorbed by the absorbent elements was measured and taken as the dynamic quantity of reflow (in g).

The measurements described above were respectively carried out for five samples of each sanitary napkin, and the mean value of the five measured values was calculated and taken as each of the absorption time, the reabsorption time, and the dynamic quantity of reflow.

<Leakage Test (Number of Occurrence of Leakage)>

As illustrated in FIG. 24, a sanitary napkin 80 obtained in each of Examples 23 through 30 and Comparative Examples 20, 21, 22, and 23 was fitted to the movable female hip model 90. Shorts were then put on the model 90, and the model 90 was caused to walk at a walking speed of 100 steps/minute (i.e., 50 m/minute) for 10 minutes.

Thereafter, while the model 90 was walking, 5 g of defibrinated equine blood was injected through a tube 91 into the sanitary napkin 80. The model 90 was then caused to continue to walk at the same walking speed for 20 minutes. At this time, the number of the samples, which exhibited leakage, among 10 samples of each sanitary napkin, was counted. Thereafter, 5 g of defibrinated equine blood was again injected through the tube 91 into the sanitary napkin 80, and the model 90 was then caused to continue to walk at the same walking speed for 20 minutes. At this time, the number of the samples, which exhibited leakage, among 10 samples of each sanitary napkin, was again counted.

TABLE 5

| | Blood absorption time (seconds) | | Dynamic quantity of reflow | Number of occurrence of leakage | |
|---|---|---|---|---|---|
| | 5 g | 10 g (reabsorption) | (g) | 5 g | 10 g |
| Examples | | | | | |
| 23 | 13 | 22 | 0.3 | 0 | 1 |
| 24 | 17 | 28 | 0.4 | 0 | 3 |
| 25 | 10 | 21 | 0.2 | 0 | 1 |
| 26 | 15 | 25 | 0.3 | 0 | 2 |
| 27 | 18 | 22 | 0.1 | 0 | 0 |
| 28 | 14 | 20 | 0.3 | 0 | 0 |
| 29 | 15 | 22 | 0.3 | 0 | 0 |
| 30 | 17 | 24 | 0.3 | 0 | 0 |
| Comp. Examples | | | | | |
| 20 | 42 | 92 | 0.9 | 0 | 7 |

TABLE 5-continued

|  | Blood absorption time (seconds) | | Dynamic quantity of reflow | Number of occurrence of leakage | |
|---|---|---|---|---|---|
|  | 5 g | 10 g (reabsorption) | (g) | 5 g | 10 g |
| 21 | 25 | 55 | 1.2 | 0 | 6 |
| 22 | 35 | 53 | 0.6 | 0 | 5 |
| 23 | 25 | 47 | 1.0 | 0 | 6 |

When the results of the blood absorption time and the dynamic quantity of reflow shown in Table 5 are studied, it can be found that, with the sanitary napkins in accordance with the present invention, the blood absorption time falls within the range of 10 to 18 seconds, the blood reabsorption time falls within the range of 20 to 28 seconds, and the dynamic quantity of reflow falls within the range of 0.1 to 0.4 g. Thus, with the sanitary napkins in accordance with the present invention, good results are obtained with respect to both the blood absorption time and the dynamic quantity of reflow. However, with the sanitary napkins obtained in Comparative Examples, the blood reabsorption time is as long as 47 to 100 seconds, and the dynamic quantity of reflow is as large as 0.6 to 1.2 g. Thus, the sanitary napkins obtained in Comparative Examples cannot satisfy the requirement with respect to the blood absorption time, nor can it satisfy the requirement with respect to the dynamic quantity of reflow.

Also, with the sanitary napkins in accordance with the present invention, the number of occurrence of leakage at the time of 10 g of absorption is as small as 0 to 3. Thus the sanitary napkins in accordance with the present invention exhibit good inhibition of leakage. On the other hand, with the sanitary napkins obtained in Comparative Examples, the number of occurrence of leakage at the time of 10-g absorption is as large as 5 to 7.

Specifically, the absorbent article in accordance with the present invention, which is provided with the absorbent member constituted of a combination of the absorbent polymer having a high liquid retentive capacity and a high permeation rate and the crosslinked cellulose fibers, exhibits good absorption characteristics.

On the other hand, the absorbent article, which comprises only the crosslinked cellulose fibers or only the absorbent polymer having a high retentive capacity and a high permeability as in Comparative Example 22 or 23, cannot exhibit good effects and has insufficient absorption characteristics.

Also, the absorbent article in accordance with the present invention can exhibits its effects to the largest extent as a large excretion amount type of absorbent article, which is to be used for night or for long-time use. Even if a large amount of the absorbent polymer is used, the gel blocking phenomenon will not occur with the absorbent article in accordance with the present invention. Further, even under the conditions of large amounts of body fluid excretion, the absorbent article in accordance with the present invention exhibits little reflow of the body fluid from the absorbent member to the surface and exhibits little leakage.

EXAMPLES 31 and 32

Preparation of Absorbent Article

As illustrated in FIG. 2, a hot melt (supplied under the trade name "Topko P-618B" by Toyo Petrolite Co., Ltd.) was spread in a spiral pattern on the diffusing absorbent paper 2d having a length of 175 mm and a width of 190 mm at an amount of 10 g per 1 m² diffusing absorbent paper. Thereafter, 0.5 g of the absorbent polymer 2b was spread approximately uniformly (at an amount of approximately 38 g per 1 m² absorbent paper) over an area of a width of 75 mm on the diffusing absorbent paper 2d. The absorbent polymer 2b was then included in and combined with the diffusing absorbent paper 2d into a unitary body. The integral body thus obtained was then included and covered with the permeable absorbent paper 2c. As the permeable absorbent paper 2c, each of the permeable absorbent paper obtained in Example 7 and the permeable absorbent paper obtained in Example 8 was cut to a length of 175 mm and a width of 130 mm, and each of the thus cut paper sheets was used. In this manner, an absorbent member 2 having the configuration shown in FIG. 2 was obtained.

The diffusing absorbent paper 2d was prepared in the manner described below. Specifically, 60 parts by weight of the mercerized pulp fibers (supplied under the trade name "POROSANIER-J" by ITT Rayonier Inc.), which had a degree of fiber roughness of 0.36 mg/m and a degree of fiber roundness of 0.80, and 40 parts by weight of softwood kraft pulp NBKP (supplied under the trade name "SKEENA PRIME" by Skeena Cellulose Co.), which had a degree of fiber roughness of 0.18 mg/m and a degree of fiber roundness of 0.32, were respectively dispersed and mixed together in water. A paper was then prepared from the resulting mixture by using a paper machine and dried. In this manner, the diffusing absorbent paper 2d having a basis weight of 40 g/m² was obtained.

The other procedures were carried out in the same manner as that in Example 23, and a sanitary napkin having the configuration shown in FIG. 2 was obtained.

COMPARATIVE EXAMPLES 24 to 28

Preparation of Absorbent Article

A sanitary napkin having the configuration shown in FIG. 2 were obtained in the same manner as that in Example 31, except that the absorbent paper obtain in each of Comparative Examples 6 through 10 was used in lieu of the permeable absorbent paper 2c used in Examples 31 and 32.

As for the sanitary napkins obtained in Examples 31 and 32 and Comparative Examples 24 through 28, the blood absorption time, the dynamic quantity of reflow, and the number of occurrence of leakage were measure. The results shown in Table 6 were obtained.

TABLE 6

|  | Blood absorption time (seconds) | | Dynamic quantity of reflow | Number of occurrence of leakage | |
|---|---|---|---|---|---|
|  | 5 g | 10 g (reabsorption) | (g) | 5 g | 10 g |
| Examples |  |  |  |  |  |
| 31 | 18 | 27 | 0.3 | 0 | 1 |
| 32 | 22 | 31 | 0.4 | 0 | 2 |
| Comp. Examples |  |  |  |  |  |
| 24 | 50 | 95 | 1.2 | 0 | 8 |
| 25 | 35 | 65 | 0.8 | 0 | 6 |
| 26 | 45 | 80 | 1.0 | 0 | 5 |

TABLE 6-continued

|  | Blood absorption time (seconds) | | Dynamic quantity of reflow | Number of occurrence of leakage | |
|---|---|---|---|---|---|
|  | 5 g | 10 g (reabsorption) | (g) | 5 g | 10 g |
| 27 | 45 | 85 | 0.9 | 0 | 6 |
| 28 | 40 | 70 | 0.8 | 0 | 5 |

EXAMPLES 33, 34, 35, and 36

Preparation of Absorbent Article

As illustrated in FIG. 2, as the diffusing absorbent paper 2d having a length of 175 mm and a width of 190 mm, the diffusing absorbent paper obtained in each of Examples 10, 12, 13, and 16 was used. A hot melt (supplied under the trade name "Topko P-618B" by Toyo Petrolite Co., Ltd.) was spread in a spiral pattern with a basis weight of 10 g/m$^2$ on the diffusing absorbent paper 2d. Thereafter, 0.5 g of the absorbent polymer 2b was spread approximately uniformly ) over an area of a width of 75 mm on the diffusing absorbent paper 2d at an amount of approximately 38 g per 1 m$^2$ diffusing absorbent paper. The absorbent polymer 2b was then included in and combined with the diffusing absorbent paper 2d into a unitary body. The integral body thus obtained was then included and covered with the permeable absorbent paper 2c having been cut to a length of 175 mm and a width of 130 mm. In this manner, an absorbent member 2 having the configuration shown in FIG. 2 was obtained.

The permeable absorbent paper 2c was prepared in the manner described below. Specifically, 95 parts by weight of the mercerized pulp fibers (supplied under the trade name "POROSANIER-J" by ITT Rayonier Inc.), which had a degree of fiber roughness of 0.36 mg/m and a degree of fiber roundness of 0.80, and 5 parts by weight of polyvinyl alcohol fibers (supplied under the trade name "Fibri Bond" by Sansho K.K.), which had a diameter of 1 denier and a length of 3 mm, were respectively dispersed and mixed together in water. A paper was then prepared from the resulting mixture by using a paper machine and dried. In this manner, the permeable absorbent paper 2c having a basis weight of 40 g/m$^2$ was obtained.

The other procedures were carried out in the same manner as that in Example 23, and a sanitary napkin having the configuration shown in FIG. 2 was obtained.

COMPARATIVE EXAMPLES 29 to 33

Preparation of Absorbent Article

A sanitary napkin having the configuration shown in FIG. 2 were obtained in the same manner as that in Example 33, except that the absorbent paper obtained in each of Comparative Examples 11 through 15 was used in lieu of the diffusing absorbent paper 2d used in Examples 33, 34, 35, and 36.

As for the sanitary napkins obtained in Examples 33, 34, 35, and 36 and Comparative Examples 29 through 33, the blood absorption time, the dynamic quantity of reflow, and the number of occurrence of leakage were measured. The results shown in Table 7 were obtained.

TABLE 7

|  | Blood absorption time (seconds) | | Dynamic quantity of reflow | Number of occurrence of leakage | |
|---|---|---|---|---|---|
|  | 5 g | 10 g (reabsorption) | (g) | 5 g | 10 g |
| Examples | | | | | |
| 33 | 25 | 35 | 0.2 | 0 | 1 |
| 34 | 22 | 31 | 0.4 | 0 | 2 |
| 35 | 28 | 38 | 0.4 | 0 | 2 |
| 36 | 26 | 36 | 0.2 | 0 | 2 |
| Comp. Examples | | | | | |
| 29 | 50 | 85 | 1.0 | 0 | 7 |
| 30 | 45 | 78 | 0.8 | 0 | 5 |
| 31 | 40 | 73 | 0.7 | 0 | 5 |
| 32 | 50 | 82 | 1.0 | 0 | 6 |
| 33 | 40 | 70 | 0.7 | 0 | 5 |

Effects of the absorbent article in accordance with the present invention, which corresponds to a large excretion amount type of absorbent article, which is to be used for person having a large amount of excretion, for night, for long-time use, or the like, will be verified hereinbelow.

EXAMPLE 37

Preparation of Absorbent Article

A sanitary napkin having the configuration shown in FIG. 1 was obtained in the same manner as that in Example 23, except that the amount of the absorbent polymer (A) spread was increased from 0.5 g/sheet (a basis weight of approximately 39 g/m$^2$) to 1.5 g/sheet (a basis weight of approximately 117 g/m$^2$).

EXAMPLE 38

Preparation of Absorbent Article

A sanitary napkin having the configuration shown in FIG. 2 was obtained in the same manner as that in Example 25, except that the absorbent polymer (B) was used in lieu of the absorbent polymer (A), the amount of the absorbent polymer spread was increased from 0.5 g/sheet (a basis weight of approximately 39 g/m$^2$) to 1.5 g/sheet (a basis weight of approximately 117 g/m$^2$).

EXAMPLE 39

Preparation of Absorbent Article

As the composite absorbent paper 2g, the composite absorbent paper, which had been obtained in Example 22, was cut to a length of 175 mm and a width of 150 mm, and the cut paper thus obtained was used. A thermally fusible bonding was spread in a spiral pattern in a proportion of approximately 10 g/m$^2$ on the side of the polymer dispersing paper of the composite absorbent paper. Thereafter, as the absorbent polymer 2b, 1.5 g of the absorbent polymer (A) was spread approximately uniformly (at a basis weight of approximately 117 g/m$^2$) over an area of a length of 175 mm and a width of 73 mm on the composite absorbent paper. The two ends of the composite absorbent paper along its longitudinal direction were then turned up such that a unitary body having a width of 73 mm might be obtained. In this manner, an absorbent member 2 having the configuration shown in FIG. 6 was obtained.

The other procedures were carried out in the same manner as that in Example 23, and a sanitary napkin having the configuration shown in FIG. 6 was obtained.

EXAMPLE 40

Preparation of Absorbent Article

A sanitary napkin having the configuration shown in FIG. 6 was obtained in the same manner as that in Example 39, except that the composite absorbent paper obtained in Example 21 was used in lieu of the composite absorbent paper 2g (i.e., the composite absorbent paper obtained in Example 22) used in Example 39.

COMPARATIVE EXAMPLE 34

Preparation of Absorbent Article

As the cellulose fibers 2a, the cellulose fibers (D), which had been adjusted so as to have a basis weight of 150 g/m$^2$ and a size of a length of 175 mm and a width of 73 mm, were used. As the absorbent polymer 2b, 1.5 g (a basis weight of 117 g/m$^2$) of the absorbent polymer (D) was spread approximately uniformly to the cellulose fibers (D). The resulting mixture was adjusted so as to have a thickness of 1 mm and was included in the absorbent paper, which had been obtained in Comparative Example 6 and cut to a length of 175 mm and a width of 160 mm. In this manner, an absorbent member 2 having the configuration shown in FIG. 1 was obtained.

The other procedures were carried out in the same manner as that in Example 23, and a sanitary napkin having the configuration shown in FIG. 1 was obtained.

COMPARATIVE EXAMPLE 35

Preparation of Absorbent Article

The absorbent paper, which had been obtained in Comparative Example 15, was cut to a length of 175 mm and a width of 190 mm. A thermally fusible bonding was spread in a spiral pattern in a proportion of approximately 10 g/m$^2$ on absorbent paper. Thereafter, as the absorbent polymer 2b, 1.5 g of the absorbent polymer (E) was spread approximately uniformly (at a basis weight of approximately 117 g/m$^2$) over an area of a length of 175 mm and a width of 73 mm on the absorbent paper. The two ends of the absorbent paper were then turned up in order to include the absorbent polymer such that a unitary body having a width of 73 mm might be obtained. The integral body thus obtained was then included and covered with the absorbent paper, which had been obtained in Comparative Example 10 and cut to a length of 175 mm and a width of 130 mm. In this manner, an absorbent member 2 having the configuration shown in FIG. 2 was obtained.

The other procedures were carried out in the same manner as that in Example 23, and a sanitary napkin having the configuration shown in FIG. 2 was obtained.

COMPARATIVE EXAMPLES 36 and 37

Preparation of Absorbent Article

A sanitary napkin was obtained in the same manner as that in Example 27, except that the composite absorbent paper obtained in each of Comparative Examples 17 and 18 was used as the composite absorbent paper 2f used in Example 27, and 1.5 g of the absorbent polymer was spread.

COMPARATIVE EXAMPLE 38

Preparation of Absorbent Article

A sanitary napkin having the configuration shown in FIG. 6 was obtained in the same manner as that in Example 39, except that the composite absorbent paper obtained in Comparative Example 19 was used as the composite absorbent paper 2g in lieu of the composite absorbent paper obtained in Example 22.

As for the sanitary napkins obtained in Examples 37, 38, 39, and 40 and Comparative Examples 34 through 38, in order to investigate mainly the absorption performance with respect to the absorption of a large amount of body fluid under the conditions of high excretion amounts and long-time use, the tests for the absorption time, the dynamic quantity of reflow, and leakage under the conditions of large amounts of absorption were carried out with the methods described below. The results shown in Table 8 were obtained.

<Measurement of Absorption Time (5 g), Reabsorption Time (10 g), Threefold Absorption Time (15 g), and Dynamic Quantity of Reflow>

The blood absorption time and the reabsorption time were measured in the same manner as that described above. As for the threefold blood absorption time, after the reabsorption time was measured, 5 g of defibrinated equine blood was further poured, and the absorption time taken for the liquid to be absorbed completely was measured.

As for the dynamic quantity of reflow, after the threefold blood absorption time had been measured, the sanitary napkin was left to stand for 20 minutes. The sanitary napkin was then put on a movable female hip model 90 in the same manner as that described above. Thereafter, the model 90 was caused to walk at a walking speed of 100 steps/minute (i.e, 50 m/minute) for 1 minute. The quantity of reflow of the defibrinated equine blood (in g) was then measured.

<Leakage Test (Number of Occurrence of Leakage)>

After 5 g of defibrinated equine blood was injected twice and the number of occurrence of leakage was measured twice in the leakage test described above, 5 g of defibrinated equine blood was further injected, and the model 90 was then caused to continue to walk for 20 minutes. At this time, the number occurrence of leakage was again counted.

TABLE 8

| | Blood absorption time (seconds) | | | Dynamic quantity of reflow (g) | Number of occurrence of leakage | | |
|---|---|---|---|---|---|---|---|
| | 5 g | 10 g (reabsorption) | 15 g (threefold absorption) | | 5 g | 10 g | 15 g |
| Examples | | | | | | | |
| 37 | 12 | 21 | 43 | 0.3 | 0 | 0 | 3 |
| 38 | 10 | 18 | 28 | 0.2 | 0 | 0 | 1 |
| 39 | 10 | 16 | 25 | 0.1 | 0 | 0 | 0 |
| 40 | 10 | 18 | 28 | 0.2 | 0 | 0 | 1 |
| Comp. Examples | | | | | | | |
| 34 | 43 | 195 | 352 | 1.5 | 0 | 7 | 10 |
| 35 | 20 | 45 | 182 | 2.1 | 0 | 3 | 10 |
| 36 | 60 | 100 | 180 | 0.9 | 0 | 7 | 10 |
| 37 | 45 | 80 | 130 | 0.9 | 0 | 7 | 10 |
| 38 | 50 | 95 | 145 | 0.8 | 0 | 5 | 10 |

As is clear from the results shown in Table 8, it can be found that, with the sanitary napkins in accordance with the present invention, which contain the crosslinked cellulose fibers and a large amount of the absorbent polymer having a high retentive capacity and a high permeability, the three-fold absorption time for 15 g with respect to the conditions of long-time use and large excretion amounts is as short as 25 to 43 seconds. Also, the quantity of reflow is as small as 0.1 to 0.3 g. Thus the sanitary napkins in accordance with the present invention are markedly better than the articles for comparison, which contain a similar large amount of the absorbent polymer.

Also, with the sanitary napkins in accordance with the present invention, the number of occurrence of leakage at the time of 15 g of absorption is as small as 0 to 3. Thus the sanitary napkins in accordance with the present invention exhibit good inhibition of leakage. On the other hand, with the sanitary napkins for comparison, all of the 10 samples of each sanitary napkin tested exhibited the liquid leakage.

Further, it can be found that, with the combination of the composite absorbent paper comprising the crosslinked cellulose fibers having a high liquid permeability and a high diffusing capacity and the polymer having a high retentivity and a high permeability, the absorbent article can be obtained, in which the respective absorbent materials do not separate from one another and the flow of the body fluid to the absorbent polymer is idealized markedly, and which has a very simple configuration, a high absorbency, and a very thin thickness. Such effects could not be obtained with the conventional absorbent article constituted of a combination of many absorbent materials.

EXAMPLE 41

Preparation of Absorbent Article

As illustrated in FIG. 9, as the diffusing absorbent paper 2d having a length of 175 mm and a width of 190 mm, the diffusing absorbent paper obtained in Example 14 was used. A hot melt (supplied under the trade name "Topko P-618B" by Toyo Petrolite Co., Ltd.) was spread in a spiral pattern with a basis weight of 10 g/m$^2$ on the diffusing absorbent paper 2d. Thereafter, as the absorbent polymer 2b, 1.5 g of the absorbent polymer (A) was spread approximately uniformly ) over an area of a width of 75 mm on the diffusing absorbent paper 2d at an amount of approximately 114 g per 1 m$^2$. The absorbent polymer 2b was then included in and combined with the diffusing absorbent paper 2d into a unitary body, which was taken as a polymer sheet. The polymer sheet was then included and covered with the permeable absorbent paper 2c. As the permeable absorbent paper 2c, the permeable absorbent paper obtained in Example 9 was cut to a length of 175 mm and a width of 130 mm, and the thus cut paper was used. In this manner, the absorbent member 2 was obtained. The obtained absorbent member 2 was wrapped up in a polyethylene-laminated waterproof paper, which served as the back sheet 3 and had a length of 205 mm and a width of 95 mm.

The other procedures were carried out in the same manner as that in Example 23, and a sanitary napkin was thereby obtained.

EXAMPLE 42

Preparation of Absorbent Article

As illustrated in FIG. 11, as the diffusing absorbent paper 2d having a length of 175 mm and a width of 75 mm, the diffusing absorbent paper obtained in Example 15 was used. A hot melt was spread in a spiral pattern among the three sheets of the diffusing absorbent paper 2d at an amount of 10 g per 1 m$^2$ diffusing absorbent paper. Thereafter, as the absorbent polymer 2b, 1 g of the absorbent polymer (A) was spread approximately uniformly in each of the two regions formed by the three sheets of the diffusing absorbent paper 2d. Thus, a total of 2 g of the absorbent polymer (A) was spread at a total amount of approximately 152 g per 1 m$^2$ diffusing absorbent paper. The absorbent polymer 2b was then included in and combined with the diffusing absorbent paper 2d into a unitary body, which was taken as a polymer sheet. The polymer sheet was then included and covered with the permeable absorbent paper 2c. As the permeable absorbent paper 2c, the permeable absorbent paper obtained in Example 7 was cut to a length of 175 mm and a width of 130 mm, and the thus cut paper was used. In this manner, the absorbent member 2 having the configuration shown in FIG. 11 was obtained.

The other procedures were carried out in the same manner as that in Example 23, and a sanitary napkin was thereby obtained.

EXAMPLE 43

Preparation of Absorbent Article

An absorbent member 2 was prepared in the same manner as that in Example 42, except that the absorbent polymer (B) was used in lieu of the absorbent polymer (A) used in Example 42. In this manner, a sanitary napkin having the configuration shown in FIG. 11 was obtained.

EXAMPLE 44

Preparation of Absorbent Article

An absorbent member 2 was prepared in the same manner as that in Example 42, except that the absorbent polymer (C) was used in lieu of the absorbent polymer (A) used in Example 42. In this manner, a sanitary napkin having the configuration shown in FIG. 11 was obtained.

EXAMPLE 45

Preparation of Absorbent Article

As illustrated in FIG. 13, 2 g (a basis weight of approximately 152 g/m$^2$) of the cellulose fibers (A), which served as the fluff pulp 2h, and 2 g (a basis weight of approximately 152 g/m$^2$) of the absorbent polymer (B), which served as the absorbent polymer 2b, were mixed together and formed into a sheet. Also, the sheet thus formed was then included in and combined with the permeable absorbent paper 2c into a unitary body. As the permeable absorbent paper 2c, the permeable absorbent paper obtained in Example 7 was cut to a length of 175 mm and a width of 130 mm, and the thus cut paper was used. In this manner, the absorbent member 2 was obtained.

The other procedures were carried out in the same manner as that in Example 23, and a sanitary napkin having the configuration shown in FIG. 13 was thereby obtained.

COMPARATIVE EXAMPLE 39

Preparation of Absorbent Article

A sanitary napkin having the configuration shown in FIG. 9 was obtained in the same manner as that in Example 41, except that the absorbent paper obtained in Comparative Example 11 was used in lieu of the diffusing absorbent paper, which had been obtained in Example 14 and used as the diffusing absorbent paper 2d in Example 23, the absorbent paper obtained in Comparative Example 11 was used in lieu of the permeable absorbent paper, which had been obtained in Example 9 and used as the permeable absorbent paper 2c, and the absorbent polymer (D) was used as the absorbent polymer 2b in lieu of the absorbent polymer (A).

COMPARATIVE EXAMPLE 40

Preparation of Absorbent Article

A sanitary napkin having the configuration shown in FIG. 11 was obtained in the same manner as that in Example 42, except that the absorbent paper obtained in Comparative Example 16 was used in lieu of the diffusing absorbent paper, which had been obtained in Example 15 and used as the diffusing absorbent paper 2d in Example 42, the absorbent paper obtained in Comparative Example 16 was used in lieu of the permeable absorbent paper, which had been obtained in Example 7 and used as the permeable absorbent paper 2c, and 0.7 g of the absorbent polymer (E) was used as the absorbent polymer 2b in lieu of the absorbent polymer (A).

COMPARATIVE EXAMPLE 41

Preparation of Absorbent Article

A sanitary napkin having the configuration shown in FIG. 13 was obtained in the same manner as that in Example 45, except that softwood pulp (supplied under the trade name "NB-420" by Weyerhauser Paper) was used in lieu of the cellulose fibers (A), which was used as the fluff pulp 2h in Example 45, the absorbent paper obtained in Comparative Example 10 was used in lieu of the permeable absorbent paper, which had been obtained in Example 7 and used as the permeable absorbent paper 2c, and the absorbent polymer (D) was used as the absorbent polymer 2b in lieu of the absorbent polymer (B).

COMPARATIVE EXAMPLE 42

Preparation of Absorbent Article

A sanitary napkin having the configuration shown in FIG. 13 was obtained in the same manner as that in Example 45, except that softwood pulp (supplied under the trade name "NB-420" by Weyerhauser Paper) was used in lieu of the cellulose fibers (A), which was used as the fluff pulp 2h in Example 45, the absorbent paper obtained in Comparative Example 11 was used in lieu of the permeable absorbent paper, which had been obtained in Example 7 and used as the permeable absorbent paper 2c, and 0.5 g (a basis weight of approximately 38 g/m$^2$) of the absorbent polymer (C) was used as the absorbent polymer 2b in lieu of 2 g of the absorbent polymer (B).

COMPARATIVE EXAMPLE 43

Preparation of Absorbent Article

A sanitary napkin was obtained in the same manner as that in Example 23, except that an absorbent member used in a commercially available sanitary napkin (supplied under the trade name "FREE DAY" by Kao Corp.) was taken out from the sanitary napkin and used as the absorbent member.

COMPARATIVE EXAMPLE 44

Preparation of Absorbent Article

A sanitary napkin was obtained in the same manner as that in Example 23, except that an absorbent member used in a commercially available, super-thin type of sanitary napkin (supplied under the trade name "FREE DAY Safety Slim Regular" by Kao Corp.) was taken out from the sanitary napkin and used as the absorbent member.

As for the absorbent members used in Examples 41 through 45 and Comparative Examples 39 through 44, he centrifugal retentive capacity with respect to pseudo-blood, which was measured after equilibrium absorption swelling with the pseudo-blood, and the permeation rate with respect to pseudo-blood were measured with the methods described below. The results shown in Table 9 were obtained.

<Measurement of Centrifugal Retentive Capacity of the Absorbent Member of Pseudo-blood After Equilibrium Absorption Swelling>

The absorbent member was included in a bag formed with paper and nonwoven fabric such that the polymer may not fall from the bag. The bag comprising the absorbent member was placed in a vat comprising 1,000 ml of pseudo-blood and left to stand for 30 minutes. The bag comprising the absorbent member was then put in a centrifugal separator (Model H-130C supplied by Kokusan Enshinki K.K.) and subjected to rotation at a rotation speed of 2,000 rpm (at a centrifugal acceleration of 895 G) for 10 minutes. Thereafter, the weight of the absorbent member was measured, and the centrifugal retentive capacity was calculated with the formula shown below.

Centrifugal retentive capacity (g)=[weight of the absorbent member after centrifugal separation (g)]−[original weight of the absorbent member (g)]

<Measurement of the Permeation Rate of the Absorbent Member With Respect to Pseudo-blood>

Figure 25:
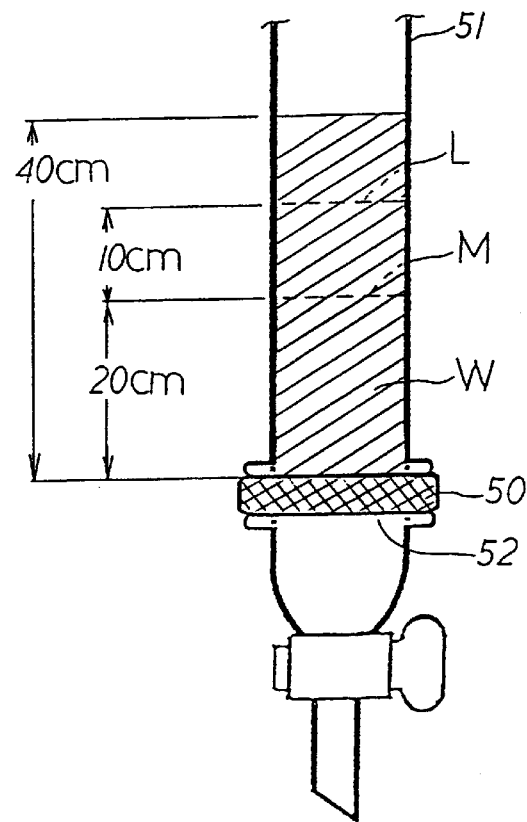
FIG. 25 is a schematic view showing a device for measuring a permeation rate of an absorbent member with respect to pseudo-blood.

As illustrated in FIG. 25, a device 51 (a buret comprising glass cylinders having a cross-sectional area of 10 cm$^2$, an inner diameter of 35.8 mm, and a length of a cylindrical portion of 500 mm) was used, wherein 80-mesh wire gauze was applied between the glass cylinders such that an absorbent member might not fall. A center portion of the absorbent member was cut to a circular shape having a diameter of 60 mm, and an absorbent member 50 having a thickness of 0.5 to 5 mm was thereby obtained. The absorbent member 50 was sandwiched between the glass cylinders and was swollen with an excess of pseudo-blood until the swelling reached equilibrium. (The absorbent member 50 was left to stand for approximately 30 minutes.) The level of the pseudo-blood W was matched to the position of 400 mm, and the cock was closed. The cock was then opened, and the time taken for the pseudo-blood W to pass between gauge L indicating the height of 300 mm and gauge M indicating the height of 200 mm (liquid amount: 100 ml) was measure. The permeation rate was then calculated with the formula shown below.

Permeation rate of the absorbent member of blood (ml blood per minute)=[100 ml]/[time taken for pseudo-blood

TABLE 9

| | Centrifugal retentive capacity (g) | Permeation rate (ml/min) |
|---|---|---|
| Examples | | |
| 41 | 58.2 | 68.5 |
| 42 | 69.5 | 72.6 |

TABLE 9-continued

|    | Centrifugal retentive capacity (g) | Permeation rate (ml/min) |
|----|------|-------|
| 43 | 62.0 | 105 |
| 44 | 46.8 | 62.3 |
| 45 | 62.2 | 73.2 |
| Comp. Examples | | |
| 39 | 49.7 | 5.7 |
| 40 | 23.5 | 35.2 |
| 41 | 66.1 | 7.2 |
| 42 | 14.3 | 82.3 |
| 43 | 10.5 | 153 |
| 44 | 15.3 | 95.1 |

As for the sanitary napkins obtained in Examples 41 through 45 and Comparative Examples 39 through 44, the test for the blood absorption time, the dynamic quantity of reflow, and leakage were carried out. The results shown in Table 10 were obtained.

TABLE 10

| | Blood absorption time (seconds) | | | Dynamic quantity of reflow (g) | Number of occurrence of leakage | | |
|---|---|---|---|---|---|---|---|
| | 5 g | 10 g (reabsorption) | 15 g (threefold absorption) | | 5 g | 10 g | 15 g |
| Examples | | | | | | | |
| 41 | 12 | 22 | 28 | 0.3 | 0 | 0 | 3 |
| 42 | 10 | 18 | 23 | 0.1 | 0 | 0 | 0 |
| 43 | 9 | 15 | 18 | 0.1 | 0 | 0 | 0 |
| 44 | 13 | 21 | 25 | 0.2 | 0 | 0 | 2 |
| 45 | 8 | 16 | 21 | 0.1 | 0 | 0 | 2 |
| Comp. Examples | | | | | | | |
| 39 | 18 | 112 | 432 | 0.9 | 0 | 10 | 10 |
| 40 | 12 | 35 | 72 | 1.8 | 0 | 5 | 10 |
| 41 | 25 | 142 | 353 | 0.8 | 1 | 4 | 10 |
| 42 | 10 | 21 | 28 | 3.0 | 0 | 2 | 10 |
| 43 | 8 | 12 | 21 | 2.8 | 0 | 1 | 10 |
| 44 | 12 | 18 | 43 | 0.8 | 0 | 0 | 10 |

When the results of the blood absorption time and the dynamic quantity of reflow shown in Table 10 are studied, it can be found that, with the sanitary napkins in accordance with the present invention, the blood absorption time, the blood reabsorption time, and the threefold blood absorption time fall within the range of 8 to 28 seconds, and the dynamic quantity of reflow falls within the range of 0.1 to 0.3 g. Thus, with the sanitary napkins in accordance with the present invention, good results are obtained with respect to both the blood absorption time and the dynamic quantity of reflow. However, with the sanitary napkins obtained in Comparative Examples, though some of them have the threefold absorption time of as short as 21 seconds and 28 seconds, their dynamic quantities of reflow are as large as 2.8 g and 3.0 g. Thus, the sanitary napkins obtained in Comparative Examples cannot satisfy both of the requirements with respect to the blood absorption time and the dynamic quantity of reflow.

Also, with the sanitary napkins in accordance with the present invention, the number of occurrence of leakage at the time of 15 g of absorption with respect to the conditions of long-time use and large excretion amounts is as small as 0 to 3. Thus the sanitary napkins in accordance with the present invention exhibit good inhibition of leakage. On the other hand, with the sanitary napkins obtained in Comparative Examples, all of the 10 samples of each sanitary napkin tested exhibited the leakage.

Specifically, the sanitary napkin in accordance with the present invention, which comprises the absorbent member having both the high blood retentive capacity and the high permeation rate, exhibits a high reabsorption rate, undergoes little liquid reflow and little leakage even under the conditions of high excretion amounts, and has a high absorbency.

EXAMPLE 46

Preparation of Liquid-permeable Topsheet

Figure 26A:
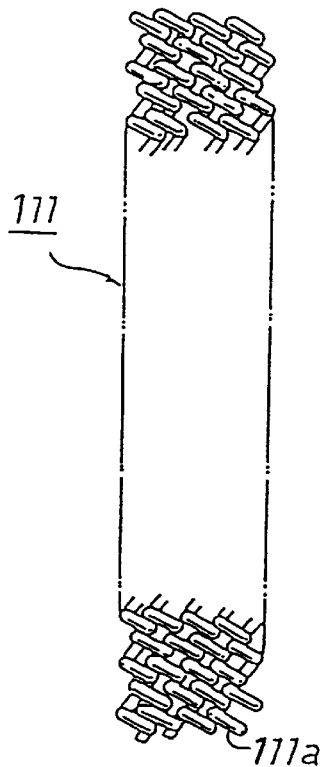
FIG. 26(A) is a plan view showing part of a wire net, which is used in producing a topsheet utilized preferably in the present invention.
Figure 26B:
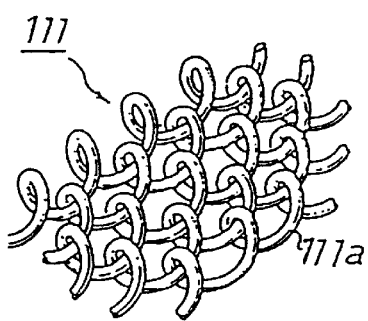
FIG. 26(B) is an enlarged perspective view showing part of the wire net shown in FIG. 26A.
Figure 27A:
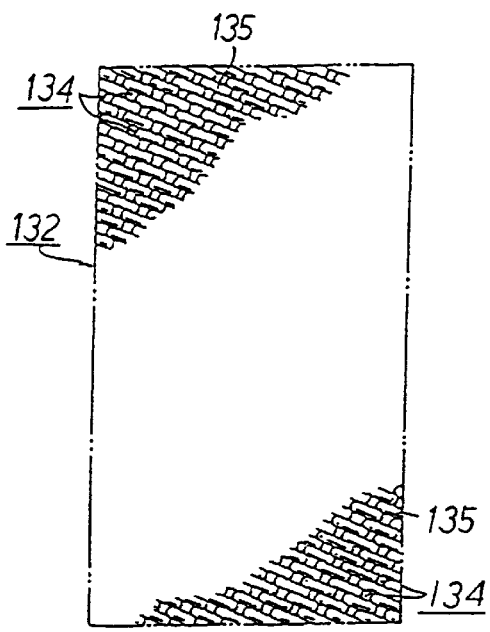
FIG. 27(A) is a plan view showing an example of the topsheet utilized preferably in the present invention.
Figure 27B:
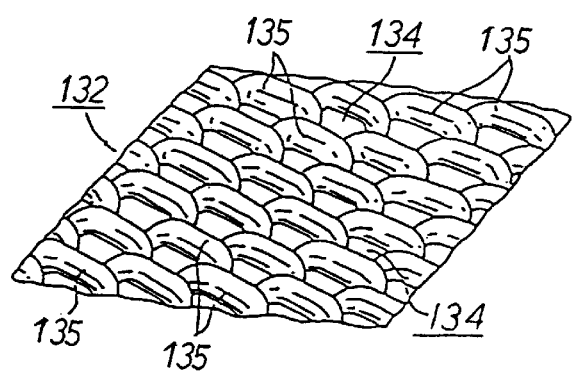
FIG. 27(B) is an enlarged perspective view showing part of the topsheet shown in FIG. 27A.

A molten resin of a low-density polyethylene (supplied by Mitsui Petrochemical Industries, Ltd.) was extruded from a T-die onto a spiral knitted wire net 111 composed of wire rods 111a shown in FIGS. 26(A) and 26B. The extruded molten resin was subjected to hot-air processing under vacuum suction. In this manner, a polyethylene porous film 132 shown in FIGS. 27(A) and 27(B) was obtained. The polyethylene porous film 132 had a shape corresponding to the surface shape of the wire net 111 and had hole portions at the positions corresponding to the spaces between the wire rods 111a of the wire net 111. (The polyethylene porous film 132 had a large number of top portions 135 composed of convex curved surfaces, the back sides of which were constituted of spaces, and a large number of hole portions 134.)

Also, in an independent operation, 100 g of mercerized pulp (supplied under the trade name "POROSANIER-J" by ITT Rayonier Inc.), which had a degree of fiber roughness of 0.36 mg/m and a degree of fiber roundness of 0.80, was dispersed in 1,000 g of an aqueous crosslinking agent solution, which contained 5% of dimethyloldihydroxyethyleneurea (supplied under the trade name "Sumitex Resin NS-19" by Sumitomo Chemical Co., Ltd.) serving as a crosslinking agent and 3% of a metal salt catalyst (supplied under the trade name "Sumitex Accelerator X-110" by Sumitomo Chemical Co., Ltd.). In this manner, the mercerized pulp was impregnated with the aqueous crosslinking agent solution.

Thereafter, the excess aqueous crosslinking agent solution was removed from the mercerized pulp until the proportion of the aqueous crosslinking agent solution with respect to the mercerized pulp became 100% (i.e. until the content of the aqueous crosslinking agent solution in the mercerized pulp became equal to 100 g). The mercerized pulp was then heated in an electric dryer at 135° C. for 10 minutes. The cellulose in the pulp was thus crosslinked, and mercerized crosslinked pulp fibers, which were the bulky cellulose fibers, were thereby obtained.

In water, 95 parts by weight of the mercerized crosslinked pulp fibers, which had thus been obtained, and 5 parts by weight of polyvinyl alcohol (PVA) fibers (supplied under the trade name "Fibri Bond" by Sansho K.K.), which had a thickness of 1 denier and a length of 3 mm and which served as the thermally fusible bonding fibers, were respectively dispersed and mixed together. A paper was then prepared from the resulting mixture and dried. In this manner, an absorbent sheet having a basis weight of 40 g/m$^2$ was obtained.

An embossing roll, which had two 2 mm-diameter circular patterns per cm$^2$, was heated to a temperature of 110° C., and the polyethylene porous film and the absorbent sheet were overlaid and combined with each other into a unitary body by the embossing operation. In this manner, a liquid-permeable topsheet (A) having the configuration shown in FIG. 15 was obtained.

EXAMPLE 47

Preparation of Liquid-permeable Topsheet

A nonwoven fabric having a basis weight of 25 g/m$^2$ was prepared with a dry hot gluing method from polyethylene/polypropylene composite fibers (supplied by Chisso Corp.), which had a diameter of 2 denier and a length of 38 mm.

Thereafter, in the same manner as that for the liquid-permeable topsheet (A), the nonwoven fabric having been prepared with the dry hot gluing method and the absorbent sheet, which was used for the liquid-permeable topsheet (A), were overlaid one upon the other and combined into a unitary body by the embossing roll. In this manner, a liquid-permeable topsheet (B) having the configuration shown in FIG. 15 was obtained.

EXAMPLE 48

Preparation of Liquid-permeable Topsheet

Softwood kraft pulp (supplied under the trade name "INDORAYON" by PT Inti Indorayon Utama), which had a degree of fiber roughness of 0.35 mg/m and a degree of fiber roundness of 0.28, was dispersed in an aqueous crosslinking agent solution, which contained 5% of dimethyloldihydroxyethyleneurea (supplied under the trade name "Sumitex Resin NS-19" by Sumitomo Chemical Co., Ltd.) serving as a crosslinking agent and 5% of a metal salt catalyst (supplied under the trade name "Sumitex Accelerator X-110" by Sumitomo Chemical Co., Ltd.). In this manner, the softwood kraft pulp was impregnated with the aqueous crosslinking agent solution.

Thereafter, the excess aqueous crosslianking agent solution was removed from the softwood kraft pulp until the proportion of the aqueous crosslinking agent solution with respect to the kraft pulp became 100%. The kraft pulp was then heated in an electric dryer at 135° C. for 10 minutes. The cellulose in the pulp fibers was thus crosslinked, and bulky cellulose fibers (crosslinked pulp fibers) were thereby obtained.

Also, 90 parts by weight of the bulky cellulose fibers, which had thus been obtained, and 10 parts by weight of PET fibers (supplied under the trade name "TMOTNSB" by Teijin Ltd.), which had a diameter of 1.1 denier and a length of 5 mm and which served as the thermally fusible bonding fibers, were respectively dispersed and mixed together in water. Thereafter, a wet-process absorbent paper having a basis weight of 40 g/m$^2$ was prepared from the resulting mixture.

Further, a nonwoven fabric having a basis weight of 25 g/m$^2$ was prepared with a dry hot gluing method from polyethylene/polypropylene composite fibers (supplied by Chisso Corp.), which had a thickness of 2 denier and a length of 38 mm. The nonwoven fabric having been prepared with the dry hot gluing method and the wet-process absorbent paper, which had been prepared in the manner described above, were overlaid one upon the other prior to the drying step in the paper machine. The resulting combination was passed through a dryer and combined into a unitary body by thermal fusion. In t his manner, a liquid-permeable topsheet (C) having the configuration shown in FIG. 15 was obtained.

EXAMPLE 49

Preparation of Liquid-permeable Topsheet

For the formation of a nonwoven fabric layer of synthetic fibers, 35 parts by weight of polyester fibers (supplied under the trade name "TM04N" by Teijin Ltd.), which had a diameter of 0.5 denier and a length of 5 mm, 45 parts by weight of polyester fibers (supplied under the trade name "N-790" by Kuraray Co., Ltd.), which had a diameter of 2.5 denier and a length of 5 mm, and 20 parts by weight of polypropylene (core)—vinyl acetate (sheath) composite fibers (supplied under the trade name "EA" by Chisso Corp.), which had a diameter of 1.5 denier and a length of 5 mm, were respectively dispersed in water. A nonwoven fabric having a basis weight of 25 g/m$^2$ was then prepared from the resulting dispersion by using a first paper machine.

Thereafter, in a second paper machine, 90 parts by weight of the bulky cellulose fibers (mercerized crosslinked pulp fibers), which were used for the liquid-permeable topsheet (A), and 10 parts by weight of a low melting point type of polyester fibers (supplied under the trade name "TMOTNSB" by Teijin Ltd.), which had a diameter of 1.1 denier and a length of 5 mm and which served as the thermally fusible bonding fibers, were respectively dispersed in water. Thereafter, an absorbent sheet having a basis weight of 40 g/m$^2$ was prepared from the resulting dispersion in the second paper machine. The absorbent sheet thus prepared and the nonwoven fabric obtained in the first paper machine were overlaid one upon the other. The resulting combination was combined into a unitary body through thermal fusion in the drying step in the paper machine. In this manner, a liquid-permeable topsheet (D) having the configuration shown in FIG. 15 was obtained

EXAMPLE 50

Preparation of Liquid-permeable Topsheet

For the formation of a nonwoven fabric layer of synthetic fibers, the same constituents and the same proportions as those for the nonwoven fabric layer of the liquid-permeable topsheet (D) were employed. In this manner, a nonwoven fabric having a basis weight of 25 g/m$^2$ was prepared by using a first paper machine.

Thereafter, in a second paper machine, 90 parts by weight of crosslinked pulp having a torsion structure (supplied under the trade name "High Bulk Additive" by Weyerhauser Paper), which served as the bulky cellulose fibers, and 10 parts by weight of a low melting point type of polyester fibers (supplied under the trade name "TMOTNSB" by Teijin Ltd.), which had a diameter of 1.1 denier and a length of 5 mm and which served as the thermally fusible bonding fibers, were respectively dispersed in water. Thereafter, an absorbent sheet having a basis weight of 40 g/m$^2$ was prepared from the resulting dispersion in the second paper machine.

Thereafter, in a third paper machine, 30 parts by weight of crosslinked pulp having a torsion structure (supplied under the trade name "High Bulk Additive" by Weyerhauser Paper), which served as the bulky cellulose fibers, and 70 parts by weight of softwood kraft pulp NBKP (supplied under the trade name "SKEENA PRIME" by Skeena Cellulose Co.), which had a degree of fiber roughness of 0.18 mg/m and a degree of fiber roundness of 0.32, were respectively dispersed in water. Thereafter, an absorbent paper having a basis weight of 20 g/m$^2$ was prepared from the resulting dispersion in the third paper machine. The nonwoven fabric of synthetic fibers obtained in the first paper machine, the absorbent sheet obtained in the second paper machine, and the absorbent paper obtained in the third paper machine were successively overlaid one upon another. The resulting combination was combined into a unitary body in the drying step in the paper machine. In this manner, a topsheet (E) having the configuration shown in FIG. 17 was obtained.

COMPARATIVE EXAMPLE 45

Preparation of Liquid-permeable Topsheet

In water, 100 parts by weight of softwood kraft pulp NBKP (supplied under the trade name "SKEENA PRIME" by Skeena Cellulose Co.), which had a degree of fiber roughness of 0.18 mg/m and a degree of fiber roundness of 0.32, was dispersed. Thereafter, an absorbent sheet having a basis weight of 40 g/m$^2$ was prepared from the resulting dispersion. The absorbent sheet thus obtained and the polyethylene porous film, which was employed for the liquid-permeable topsheet (A), were merely overlaid one upon the other without being combined with each other into a unitary body. In this manner, a liquid-permeable topsheet (F) was obtained. In this topsheet, an absorbent sheet comprising bulky cellulose fibers was not used, and the absorbent sheet and the polyethylene porous film were not combined with each other into a unitary body.

COMPARATIVE EXAMPLE 46

Preparation of Liquid-permeable Topsheet

A nonwoven fabric having a basis weight of 25 g/m$^2$ was prepared with a dry hot gluing method from polyethylene/polypropylene composite fibers (supplied by Chisso Corp.), which had a diameter of 2 denier and a length of 38 mm.

Thereafter, 100 parts by weight of softwood kraft pulp NBKP (supplied under the trade name "SKEENA PRIME" by Skeena Cellulose Co.), which had a degree of fiber roughness of 0.18 mg/m and a degree of fiber roundness of 0.32, was dispersed in water. An absorbent sheet having a basis weight of 40 g/m$^2$ was then prepared from the resulting dispersion. In the same manner as that for the liquid-permeable topsheet (A), the nonwoven fabric having been prepared with the dry hot gluing method and the absorbent sheet, which had thus been prepared, were overlaid and combined with each other into a unitary body by the embossing roll. In this manner, a liquid-permeable topsheet (G) was obtained. In this topsheet, an absorbent sheet comprising bulky cellulose fibers was not used.

COMPARATIVE EXAMPLE 47

Preparation of Liquid-permeable Topsheet

A nonwoven fabric having a basis weight of 25 g/m$^2$ was prepared with a dry hot gluing method from polyethylene/polypropylene composite fibers (supplied by Chisso Corp.), which had a thickness of 2 denier and a length of 38 mm.

Thereafter, 95 parts by weight of rayon fibers (supplied by Daiwabo Rayon K.K.), which had a degree of fiber roughness of 0.077 mg/m and a length of 11 mm, and 5 parts by weight of polyvinyl alcohol fibers (supplied under the trade name "Fibri Bond" by Sansho K.K.), which had a diameter of 1 denier and a length of 3 mm and which served as the thermally fusible bonding fibers, were respectively dispersed in water. A rayon wet-process nonwoven fabric having a basis weight of 40 g/m$^2$ was the prepared from the resulting dispersion. Thereafter, the nonwoven fabric having been prepared with the dry hot gluing method and the rayon nonwoven fabric having thus been prepared were overlaid and combined with each other into a unitary body by using a spiral hot melt at a basis weight of 10 g. In this manner, a liquid-permeable topsheet (H) was obtained. In this topsheet, an absorbent sheet comprising bulky cellulose fibers was not used.

Thereafter, as for the liquid-permeable surface materials (A) through (H) obtained in the manner described above, the absorbency and the liquid permeability of the absorbent sheet 102b were evaluated. For the evaluation of the absorbency, the absorption height by Klemm's Method, which represented the force for drawing the liquid from the porous film or the nonwoven fabric, and the permeation time with respect to an aqueous glycerol solution, which represented the capacity for transmitting the liquid to the absorbent member, were measured. The results shown in Table 11 were obtained.

The measurements were carried out for the absorbent sheet 102b alone before it was overlaid upon and combined with the porous film or the nonwoven fabric, as or the absorbent paper 102c. As for the surface materials (C), (D), and (F), each of which was formed into a unitary body during the wet process, only the absorbent sheet 102b to be combined with the layer in contact with the user's skin was prepared and subjected to the evaluation. As for the topsheet (E), which was composed of the three layers combined into a unitary body as shown in FIG. 17, the physical properties of the absorbent sheet 102b to be combined with the layer in contact with the user's skin are important. Therefore, as for the topsheet (E), the physical properties of the absorbent sheet 102b prepared in the second paper machine were evaluated.

TABLE 11

|  |  | Liquid permeable surface sheet | Surface sheet in contact with skin | Composition of absorbent sheet not in contact with skin | Parts by weight | Combining means | Absorption height by Klemm's Method (mm) | | Permeation time for an 85% by weight aqueous glycerol solution (seconds) |
|---|---|---|---|---|---|---|---|---|---|
|  |  |  |  |  |  |  | After 1 minute ($h_1$) | After 10 minutes ($h_{10}$) |  |
| Examples | 46 | (A) | *1 | *4 *5 | 95 5 | *9 | 35 | 60 | 8 |
|  | 47 | (B) | *2 | *4 *5 | 95 5 | *9 | 35 | 60 | 8 |

TABLE 11-continued

| | | Liquid permeable surface sheet | Surface sheet in contact with skin | Composition of absorbent sheet not in contact with skin | Parts by weight | Combining means | Absorption height by Klemm's Method (mm) | | Permeation time for an 85% by weight aqueous glycerol solution (seconds) |
|---|---|---|---|---|---|---|---|---|---|
| | | | | | | | After 1 minute ($h_1$) | After 10 minutes ($h_{10}$) | |
| | 48 | (C) | *2 | *4 | 90 | *10 | 42 | 75 | 12 |
| | | | | *6 | 10 | | | | |
| | 49 | (D) | *3 | *4 | 90 | *10 | 40 | 72 | 10 |
| | | | | *6 | 10 | | | | |
| | 50 | (E) | *3 | *4 | 90 | *10 | 51 | 85 | 20 |
| | | | | *6 | 10 | | | | |
| Comp. | 45 | (F) | *1 | *7 | 100 | *11 | 31 | 70 | 430 |
| Examples | 46 | (G) | *2 | *7 | 100 | *9 | 31 | 70 | 430 |
| | 47 | (H) | *2 | *8 | 100 | *12 | 88 | 167 | 205 |

*1; Porous film
*2; Nonwoven fabric prepared by hot gluing method
*3; Wet-process nonwoven fabric
*4; Bulky cellulose fibers
*5; Thermally fusible bonding fibers (PVA)
*6; Thermally fusible bonding fibers (PET)
*7; Softwood Kraft pulp
*8; Rayon wet-process nonwoven fabric
*9; Combining by embossing into a unitary body
*10; Overlaying in a paper preparing step and combining by drying and thermal fusion into a unitary body
*11; No combining into a unitary body
*12; Combining by sparal melt into a unitary body Thereafter, in Examples 51 through 55 described below, the sanitary napkins as the absorbent articles in accordance with the present invention were prepared by using the surface materials (A) through (E). Also, in Comparative Examples 48, 49, and 50, sanitary napkins for comparison were prepared by using the surface materials (F), (G), and (H).

EXAMPLE 51

Preparation of Absorbent Article

As illustrated in FIG. 14, 0.5 g of an absorbent polymer 103b (supplied under the trade name "Aqualic CA-W4S" by Nippon Shokubai Co., Ltd.) was spread with a basis weight of 39 g/m² on fluff pulp 103a, which had been adjusted to a basis weight of 150 g/m² a density of 0.15 g/cm³, a thickness of 1 mm, a length of 175 mm, and a width of 73 mm. A wet-process absorbent paper 103c, which had been prepared from softwood kraft pulp and had a basis weight of 18 g/m², was then overlaid upon the resulting mixture of the absorbent polymer 103b and the fluff pulp 103a. In this manner, an absorbent member 103 having the configuration shown in FIG. 14, which had a length of 175 mm and a width of 73 mm, was obtained.

The absorbent member 103 thus obtained was then included in the liquid-permeable topsheet (A) having been cut to a length of 205 mm and a width of 130 mm. Further, a polyethylene back sheet 104 having a basis weight of 30 g/m², a length of 205 mm, and a width of 95 mm, was overlaid upon the liquid-permeable topsheet (A). These members were secured to one another by using a thermally fusible bonding as the fixing members 105, 105, . . . Also, two slipping-off preventing members 106, 106 were formed on the back surface side of the polyethylene-backed sheet 104 by applying a thermally fusible bonding at a basis weight of 40 g/m² and with a width of 20 mm and a length of 115 mm. In this manner, a sanitary napkin having the configuration shown in FIG. 14 was obtained. In FIG. 14, reference numeral 107 represents the release paper for covering the slipping-off preventing members 106, 106.

EXAMPLE 52

Preparation of Absorbent Article

A sanitary napkin having the configuration shown in FIG. 14 was obtained in the same manner as that in Example 51, except that the liquid-permeable topsheet (B) was used in lieu of the liquid-permeable topsheet (A) used in Example 51.

EXAMPLE 53

Preparation of Absorbent Article

A sanitary napkin having the configuration shown in FIG. 14 was obtained in the same manner as that in Example 51, except that the liquid-permeable topsheet (C) was used in lieu of the liquid-permeable topsheet (A) used in Example 51.

EXAMPLE 54

Preparation of Absorbent Article

A sanitary napkin having the configuration shown in FIG. 14 was obtained in the same manner as that in Example 51, except that the liquid-permeable topsheet (D) was used in lieu of the liquid-permeable topsheet (A) used in Example 51.

EXAMPLE 55

Preparation of Absorbent Article

As illustrated in FIG. 16, a spiral hot melt was applied with a basis weight of 10 g/m² and a width of 80 mm to the liquid-permeable topsheet (E) having a length of 205 mm and a width of 150 mm. Thereafter, 0.5 g of an absorbent polymer 103b (supplied under the trade name "Aqualic CA-W4S" by Nippon Shokubai Co., Ltd.) was approximately uniformly spread over a range of a width of approximately 73 mm and a length of 175 mm on the liquid-permeable topsheet (E). The liquid-permeable topsheet (E) was then folded in order to include the polymer and was thus combined with the polymer into a unitary body such that the width might become equal to 75 mm. Further, a polyethylene back sheet 104 having a basis weight of 30 g/m$^2$, a length of 205 mm, and a width of 95 mm, was overlaid upon the liquid-permeable topsheet (E). These members were secured to each other by using a thermally fusible bonding as the fixing members 105, 105. Also, two slipping-off preventing members 106, 106 were formed on the back surface side of the polyethylene back sheet 104 by applying a thermally fusible bonding at a basis weight of 40 g/m$^2$ and with a width of 20 mm and a length of 115 mm. In this manner, a sanitary napkin having the configuration shown in FIG. 16 was obtained. In FIG. 16, reference numeral 107 represents the release paper for covering the slipping-off preventing members 106, 106.

COMPARATIVE EXAMPLE 48

Preparation of Absorbent Article

A sanitary napkin having the configuration shown in FIG. 14 was obtained in the same manner as that in Example 51, except that the liquid-permeable topsheet (F) was used in lieu of the liquid-permeable topsheet (A) used in Example 51.

COMPARATIVE EXAMPLE 49

Preparation of Absorbent Article

A sanitary napkin having the configuration shown in FIG. 14 was obtained in the same manner as that in Example 51, except that the liquid-permeable topsheet (G) was used in lieu of the liquid-permeable topsheet (A) used in Example 51.

COMPARATIVE EXAMPLE 50

Preparation of Absorbent Article

A sanitary napkin having the configuration shown in FIG. 14 was obtained in the same manner as that in Example 51, except that the liquid-permeable topsheet (H) was used in lieu of the liquid-permeable topsheet (A) used in Example 51.

As for the sanitary napkins obtained in Examples 51 through 55 and Comparative Examples 48, 49, and 50, tests for the blood absorption time, the dry feeling of the surface, and the number of occurrence of leakage were carried out. The results shown in Table 12 were obtained. The blood absorption time was measured with the method described above. The dry feeling of the surface and the number of occurrence of leakage were measured with the methods described below.
<Evaluation of Dry Feeling of the Surface>
As illustrated in FIG. 24, a sanitary napkin 80 obtained in each of Examples 51 through 55 and Comparative Examples 48, 49, and 50 was fitted to the movable female hip model 90. Shorts were then put on the model 90 and the model 90 was caused to walk at a walking speed of 100 steps/minute (i.e., 50 m/minute) for 10 minutes.

Thereafter, while the model 90 was walking, 3 g of defibrinated equine blood was injected through the tube 91 into the sanitary napkin 80. The model 90 was then caused to continue to walk at the same walking speed for 20 minutes. At this time, the sample of the sanitary napkin was taken out from the model 90 As for the sample which had thus been taken out, a functional evaluation for the dry feeling of the surface was carried out. The dry feeling of the surface was rated on the scale shown below.

○: Little retention of the liquid was observed on the topsheet, and the surface had the dry feeling.

Δ: Slight retention of the liquid was observed on the topsheet.

Figure 28:
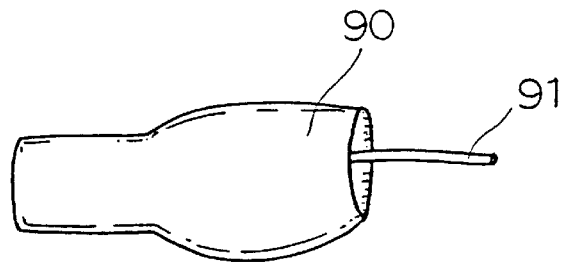
FIG. 28 is a schematic view showing how a sanitary napkin is put on the crotch of a movable model of the hip of a woman, and the movable model is caused to lie down.

×: Much retention of the liquid was observed on the topsheet, and the surface had the sticky feeling.
<Measurement of the Number of Occurrence of Leakage>
As illustrated in FIG. 24, a sanitary napkin 80 obtained in each of Examples 51 through 55 and Comparative Examples 48, 49, and 50 was fitted to the female hip model 90 Shorts were then put on the model 90 and the model 90 was caused to lie down as shown in FIG. 28.

Thereafter, 5 g of defibrinated equine blood was injected at a rate of 1 g/minute through the tube 91 into the sanitary napkin 80. The model 90 was then left to stand for 20 minutes. At this time, the number of the samples, which exhibited leakage, among 10 samples of each sanitary napkin, was counted. Thereafter, 5 g of defibrinated equine blood was again injected at the same rate through the tube 91 into the sanitary napkin 80, and the model 90 was again left to stand for 20 minutes. At this time, the number of the samples, which exhibited leakage, among 10 samples of each sanitary napkin, was again counted.

TABLE 12

|  |  | Blood absorption time | Dry feeling of | Number of occurrence of leakage | |
| --- | --- | --- | --- | --- | --- |
|  |  | (seconds) | surface | 5 g | 10 g |
| Examples | 51 | 18 | ○ | 0 | 1 |
|  | 52 | 23 | Δ ~ ○ | 0 | 2 |
|  | 53 | 20 | Δ ~ ○ | 0 | 0 |
|  | 54 | 16 | ○ | 0 | 0 |
|  | 55 | 14 | ○ | 0 | 0 |
| Comp. Examples | 48 | 75 | Δ | 10 | 10 |
|  | 49 | 92 | × | 5 | 10 |
|  | 50 | 78 | × ~ Δ | 4 | 9 |

In the sanitary napkins obtained in Examples 51 through 55, the topsheet comprises the liquid-permeable sheet constituted of the layer in contact with the user's skin and the layer not in contact with the user's skin, which layers are overlaid and combined with each other into a unitary body. The layer in contact with the user's skin comprises the porous film or the nonwoven fabric of synthetic fibers. The layer not in contact with the user's skin comprises the absorbent sheet, which at least comprises the bulky cellulose fibers and which has a high absorbency and a high permeability. Thereafter, as is clear from the results shown in Table 12, with the sanitary napkins obtained in Examples 51 through 55, the absorption time can be kept short, and the body fluid can be quickly guided to the absorbent member. Accordingly, little liquid remains on the surface, and a very dry feeling can be obtained. Also, as is clear from the results of the leakage test in the lying orientation, with the sanitary napkins obtained in Examples 51 through 55, blood can be smoothly guided to the absorbent member without flowing along the surface and without leaking.

On the other hand, with the sanitary napkin obtained in Comparative Example 48, wherein the sheet in contact with the user's skin and the absorbent sheet for absorbing blood are not combined into a unitary body, blood floats and flows on the topsheet and leaks. Also, with the sanitary napkins obtained in Comparative Examples 49 and 50, wherein the nonwoven fabric of synthetic fibers and the absorbent sheet, wherein the permeable absorbent paper having a high absorbency is overlaid and combined integrally with the sheet, which comprises the combination of the porous film or the nonwoven fabric and the absorbent sheet comprising the bulky cellulose fibers, the absorbent article can be constituted only of the liquid-permeable sheet, the absorbent polymer, and the back sheet. Therefore, the absorbent article, which has a very simple configuration, a very thin thickness, and good performance, can be obtained.

Many other variations and modifications of the invention will be apparent to those skilled in the art without departing from the spirit and scope of the invention. The above-described embodiments are, therefore, intended to be merely exemplary, and all such variations and modifications are intended to be included within the scope of the invention as defined in the appended claims.

What is claimed is:

1. An absorbent article comprising a liquid permeable topsheet, a liquid impermeable back sheet and a liquid retentive absorbent member interposed between said topsheet and said back sheet, wherein:

said absorbent member comprises an absorbent polymer and cellulose fibers;

said absorbent polymer has a centrifugal retentive capacity for physiological saline, which is measured after equilibrium absorption swelling with the physiological saline, of 30 g/g or more, and a permeation rate of physiological saline of 10 ml/minute or more, said permeation rate being measured by introducing 0.05 g of said absorbent polymer into a cylinder having a cross-sectional area of 0.785 $cm^2$ (inner diameter: 10 mm), allowing said absorbent polymer to absorb and swell with physiological saline until the swelling reaches equilibrium, and thereafter causing physiological saline to permeate through said absorbent polymer; and said cellulose fibers are crosslinked cellulose fibers obtainable by an intramolecular, intermolecular, or intramolecular and intermolecular crosslinking of said cellulose fibers.

2. The absorbent article as defined in claim 1, wherein said cellulose fibers are pulp fibers.

3. The absorbent article as defined in claim 1, wherein a degree of fiber roundness of said cellulose fibers in cross section is 0.5 or more.

4. The absorbent article as defined in claim 3, wherein said crosslinked cellulose fibers have a residual strain after compression in a wet state of less than 40%.

5. The absorbent article as defined in claim 1, wherein said crosslinked cellulose fibers are mercerized crosslinked pulp fibers obtainable by mercerizing pulp fibers and thereafter crosslinking the mercerized pulp fibers.

6. The absorbent article as defined in claim 1, wherein said absorbent member further comprises an absorbent paper comprising said crosslinked cellulose fibers.

7. The absorbent article as defined in claim 1, wherein said absorbent polymer is in the form of particles having an aspherical shape and having a degree of shape irregularity of 1.2 or more.

8. The absorbent article as defined in claim 1, wherein said absorbent polymer is used in a proportion falling within the range of 20 to 80% by weight, based on the total weight of said absorbent member, and spread over said absorbent member at an amount falling within the range of 20 to 500 g per 1 $m^2$ absorbent member.

9. The absorbent article as defined in claim 8, wherein said absorbent polymer is used in a proportion falling within the range of 30 to 60% by weight, based on the total weight of said absorbent member, and spread over said absorbent member at an amount falling within the range of 100 to 300 g per 1 $m^2$ absorbent member.

10. The absorbent article as defined in claim 1, wherein said absorbent article is a sanitary napkin and said absorbent polymer is used in an amount falling within the range of 1 to 3 g.

11. The absorbent article as defined in claim 1, wherein said absorbent member further comprises a permeable absorbent paper located at the outermost part of said absorbent member, and the permeable absorbent paper comprises 50 to 98 parts by weight of said crosslinked cellulose fibers and 2 to 30 parts by weight of thermally fusible bonding fibers, and has a basis weight of 20 to 60 $g/m^2$ and a permeation time for 10 g of an 85% by weight aqueous glycerol solution of 50 seconds or less.

12. The absorbent article as defined in claim 1, wherein said absorbent member further comprises a diffusing absorbent paper, and the diffusing absorbent paper comprises 20 to 80 parts by weight of said crosslinked cellulose fibers, 80 to 20 parts by weight of hydrophilic fine fibers, and 0 to 30 parts by weight of thermally fusible bonding fibers, and has a basis weight of 20 to 60 $g/m^2$, an absorption height after 1 minute absorption of physiological saline by Klemm's Method of 50 mm or more, an absorption height after 10 minutes absorption of physiological saline by Klemm's Method of 100 mm or more, and a permeation time for 10 g of an 85% by weight aqueous glycerol solution of 100 seconds or less.

13. The absorbent article as defined in claim 1, wherein said absorbent member further comprises a composite absorbent paper comprising a permeable absorbent paper and a diffusing absorbent paper, which are combined with each other into a unitary body, the permeable absorbent paper comprises 50 to 98 parts by weight of said crosslinked cellulose fibers, and 2 to 30 parts by weight of thermally fusible bonding fibers, and has a basis weight of 20 to 60 $g/m^2$, and the diffusing absorbent paper comprises 20 to 80 parts by weight of said crosslinked cellulose fibers, 80 to 20 parts by weight of hydrophilic fine fibers, and 0 to 30 parts by weight of thermally fusible bonding fibers, and has a basis weight of 20 to 60 $g/m^2$.

14. The absorbent article as defined in claim 13, wherein said composite absorbent paper further comprises a polymer dispersing paper, which comprises 70 to 100 parts by weight of said crosslinked cellulose fibers and 0 to 30 parts by weight of thermally fusible bonding fibers and which has a basis weight of 10 to 50 $g/m^2$, and the permeable absorbent paper, the diffusing absorbent paper, and the polymer dispersing paper are combined, in this order, with one another into a unitary body.

15. The absorbent article according to claim 1 wherein said degree of fiber roughness if from 0.3 to 2 mg/m.

16. A sanitary napkin comprising a liquid permeable topsheet, a liquid impermeable back sheet, and a liquid retentive absorbent member interposed between said topsheet and said back sheet, said sanitary napkin being characterized in that:

the absorbent member has a centrifugal retentive capacity for pseudo-blood, which is measured after equilibrium absorption swelling with the pseudo-blood, of 30 g/g or more, and a permeation rate of pseudo-blood of 50 ml/minute or more, said permeation rate being measured by securing the absorbent member having a thickness of 0.5 to 5 mm to an end of a cylinder having a cross-sectional area of 10 $cm^2$ (inner diameter: 35.8 mm), allowing the absorbent member to absorb and swell with pseudo-blood until the swelling reaches equilibrium, and thereafter causing pseudo-blood to permeate through the absorbent member.

17. The sanitary napkin as defined in claim 16, wherein said absorbent member comprises an absorbent polymer, and the absorbent polymer has a centrifugal retentive capacity for pseudo-blood, which is measured after equilibrium absorption swelling with the pseudo-blood, of 20 g/g or more; and a permeation rate of pseudo-blood of 1 ml/minute or more, said permeation rate being measured by introducing 0.05 g of the absorbent polymer into a cylinder having a cross-sectional area of 0.785 $cm^2$ (inner diameter: 10 mm), allowing said absorbent polymer to absorb and swell with pseudo-blood until the swelling reaches equilibrium, and thereafter causing pseudo-blood to permeate through the absorbent polymer.

18. The sanitary napkin as defined in claim 17, wherein said absorbent polymer is in the form of particles having an aspherical shape and having a degree of shape irregularity of 1.2 or more.

19. The sanitary napkin as defined in claim 17, wherein said absorbent polymer is used in a proportion falling within the range of 20 to 80% by weight, based on the total weight of said absorbent member, and spread over said absorbent member at an amount falling within the range of 100 to 500 g per 1 $m^2$.

20. The sanitary napkin as defined in claim 16, wherein said absorbent member comprises bulky cellulose fibers and an absorbent polymer, and the bulky cellulose fibers are selected from bulky cellulose fibers having a fiber cross-sectional area of $3.0 \times 10^{-6}$ $cm^2$ or more and a degree of fiber roundness of 0.5 or more, bulky cellulose fibers having a fiber cross-sectional area of $5.0 \times 10^{-6}$ $cm^2$ or more, or bulky cellulose fibers having a three-dimensional fiber shape.

21. The sanitary napkin as defined in claim 16, wherein said absorbent member further comprises a permeable absorbent paper located at the outermost part of said absorbent member, and the permeable absorbent paper comprises 50 to 98 parts by weight of said bulky cellulose fibers and 2 to 30 parts by weight of thermally fusible bonding fibers, an absorption height after 1 minute absorption of physiological saline by Klemm's Method falling within the range of 20 to 80 mm, an absorption height after 10 minutes absorption of physiological saline by Klemm's Method falling within the range of 30 to 100 mm, and a permeation time for 10 g of an 85% by weight aqueous glycerol solution of 50 seconds or less.

22. The sanitary napkin as defined in claim 21, wherein said absorbent member further comprises a diffusing absorbent paper located inside of the permeable absorbent paper, the diffusing absorbent paper comprises 20 to 80 parts by weight of said bulky cellulose fibers, 80 to 20 parts by weight of hydrophilic fine fibers, and 0 to 30 parts by weight of thermally fusible bonding fibers, and absorption height after 1 minute absorption of physiological saline by Klemm's Method of 50 mm or more, an absorption height after 10 minutes absorption of physiological saline by Klemm's Method of 100 mm or more, and a permeation time for 10 g of an 85% by weight aqueous glycerol solution of 100 seconds or less.

23. The sanitary napkin as defined in claim 20, wherein said bulky cellulose fibers are obtained by crosslinking mercerized pulp fibers, which have a fiber cross-sectional area of $3.0 \times 10^{-6}$ $cm^2$ or more and a degree of fiber roundness of 0.5 or more.

24. A composite absorbent paper comprising a permeable absorbent paper and a diffusing absorbent paper, wherein the permeable absorbent paper comprises 50 to 98 parts by weight of bulky crosslinked cellulose fibers obtainable by an intramolecular, intermolecular, or intramolecular and intermolecular crosslinking of cellulose fibers having a degree of fiber roughness of 0.3 mg/m or more, and 2 to 50 parts by weight of thermally fusible bonding fibers, the permeable absorbent paper having a basis weight of 20 to 60 $g/m^2$;

the diffusing absorbent paper comprises 20 to 80 parts by weight of bulky crosslinked cellulose fibers obtainable by an intramolecular, intermolecular, or intramolecular and intermolecular crosslinking of cellulose fibers having a degree of fiber roughness of 0.3 mg/m or more, 80 to 20 parts by weight of hydrophilic fine fibers, and 0 to 30 parts by weight of thermally fusible bonding fibers, the diffusing absorbent paper having a basis weight of 20 to 60 $g/m^2$; and the permeable absorbent paper and the diffusing absorbent paper are combined with each other into a unitary body.

25. The composite absorbent paper as defined in claim 24, wherein said permeable absorbent paper has a permeation time for 10 g of an 85% by weight aqueous glycerol solution of 50 seconds or less.

26. The composite absorbent paper as defined in claim 24, wherein said diffusing absorbent paper has an absorption height after 1 minute absorption of physiological saline by Klemm's Method of 50 mm or more and an absorption height after 10 minutes absorption of physiological saline by Klemm's Method of 100 mm or more, and a permeation time for 10 g of an 85% by weight aqueous glycerol solution of 100 seconds or less.

27. The composite absorbent paper as defined in any of claims 24, 25, and 26, wherein said composite absorbent paper further comprises a polymer dispersing paper comprising 70 to 100 parts by weight of bulky crosslinked cellulose fibers obtainable by an intramolecular, intermolecular, or intramolecular and intermolecular crosslinking of cellulose fibers having a degree of fiber roughness of 0.3 mg/m or more, and 0 to 30 parts by weight of thermally fusible bonding fibers, and has a basis weight of 10 to 50 $g/m^2$, and the permeable absorbent paper, the diffusing absorbent paper and the polymer dispersing paper are combined, in this order, with one another into a unitary body.

28. A diffusing absorbent paper comprising 20 to 80 parts by weight of bulky crosslinked cellulose fibers obtainable by an intramolecular, intermolecular, or intramolecular and intermolecular crosslinking of cellulose fibers having a degree of fiber roughness of 0.3 mg/m or more, 80 to 20 parts by weight of hydrophilic fine fibers, and 0 to 30 parts by weight of thermally fusible bonding fibers, wherein the diffusing absorbent paper has a basis weight of 20 to 60 $g/m^2$, a thickness under a load of 2.5 $g/m^2$ of 0.2 to 0.8 mm, an absorption height after 1 minute absorption of physiological saline by Klemm's Method of 50 mm or more, and an absorption height after 10 minutes absorption of physiological saline by Klemm's Method of 100 mm or more.

29. The diffusing absorbent paper as defined in claim 28, wherein said diffusing absorbent paper has a permeation time for 10 g of an 85% by weight aqueous glycerol solution of 100 seconds or less.

30. A permeable absorbent paper comprising 50 to 98 parts by weight of bulky crosslinked cellulose fibers obtainable by an intramolecular, intermolecular, or intramolecular and intermolecular crosslinking of cellulose fibers having a degree of fiber roughness of 0.3 mg/m or more, and 2 to 50 parts by weight of thermally fusible bonding fibers, wherein the permeable absorbent paper has a basis weight of 20 to 60 $g/m^2$.

31. The permeable absorbent paper as defined in claim 30, wherein said permeable absorbent paper has a permeation time for 10 g of an 85% by weight aqueous glycerol solution of 50 seconds or less.

32. Bulky crosslinked cellulose fibers obtainable by an intramolecular, intermolecular, or intramolecular and intermolecular crosslinking of cellulose fibers having a degree of fiber roughness of 0.3 mg/m or more.

33. The bulky crosslinked cellulose fibers as defined in claim 32, wherein a degree of fiber roundness of said cellulose fibers in cross section is 0.5 or more.

34. The bulky crosslinked cellulose fibers as defined in claim 32, wherein said bulky crosslinked cellulose fibers have a residual strain after compression in a wet state of less than 40%.

35. The bulky crosslinked cellulose fibers as defined in claim 32, wherein said bulky crosslinked cellulose fibers are obtained by mercerizing said cellulose fibers and thereafter crosslinking the mercerized cellulose fibers.

* * * * *